(12) United States Patent
Botstein et al.

(10) Patent No.: US 7,101,984 B2
(45) Date of Patent: Sep. 5, 2006

(54) SECRETED AND TRANSMEMBRANE POLYPEPTIDES AND NUCLEIC ACIDS ENCODING THE SAME

(75) Inventors: David Botstein, Belmont, CA (US); Luc Desnoyers, San Francisco, CA (US); Napoleone Ferrara, San Francisco, CA (US); Sherman Fong, Alameda, CA (US); Wei-Qiang Gao, Foster City, CA (US); Audrey Goddard, San Francisco, CA (US); Austin L. Gurney, Belmont, CA (US); James Pan, Belmont, CA (US); Margaret Ann Roy, San Francisco, CA (US); Timothy A. Stewart, San Francisco, CA (US); Daniel Tumas, Orinda, CA (US); Colin K. Watanabe, Moraga, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 27 days.

(21) Appl. No.: 10/033,167

(22) Filed: Dec. 27, 2001

(65) Prior Publication Data

US 2002/0182618 A1 Dec. 5, 2002

Related U.S. Application Data

(63) Continuation of application No. 09/866,034, filed on May 25, 2001, which is a continuation of application No. PCT/US99/28634, filed on Dec. 1, 1999.

(60) Provisional application No. 60/119,965, filed on Feb. 12, 1999.

(51) Int. Cl.
*C07H 21/02* (2006.01)
*C07H 21/04* (2006.01)
*C12Q 1/68* (2006.01)

(52) U.S. Cl. .................. 536/23.1; 435/6; 435/91.2; 536/24.3; 536/24.31; 536/24.33

(58) Field of Classification Search .................. 435/6, 435/91.2; 536/23.1, 24.3, 24.31, 24.33
See application file for complete search history.

(56) References Cited

U.S. PATENT DOCUMENTS

| | | | |
|---|---|---|---|
| 5,536,637 A | 7/1996 | Jacobs | |
| 5,831,058 A | 11/1998 | Fujiwara et al. | |
| 6,025,156 A | 2/2000 | Gwynn et al. | |
| 6,124,433 A | 9/2000 | Falb et al. | |
| 6,156,500 A | 12/2000 | Falb | |
| 6,162,604 A | 12/2000 | Jacob | |
| 6,228,582 B1 | 5/2001 | Rodier et al. | |
| 6,395,306 B1 | 5/2002 | Cui et al. | |
| 6,414,117 B1 | 7/2002 | Levinson | |
| 6,465,185 B1 | 10/2002 | Goldfine et al. | |
| 6,498,235 B1 | 12/2002 | Sheppard et al. | |
| 6,562,343 B1 | 5/2003 | Levinson | |
| 6,645,499 B1 | 11/2003 | Lal et al. | |
| 6,730,502 B1 | 5/2004 | Van Hijum et al. | |
| 6,737,522 B1 | 5/2004 | Sundick et al. | |

FOREIGN PATENT DOCUMENTS

| | | |
|---|---|---|
| DE | 198 18 620 | 10/1999 |
| WO | WO 97/38085 | 10/1997 |
| WO | WO 98 45437 | 10/1998 |
| WO | WO 00/04135 | 1/2000 |
| WO | WO 00/04140 | 1/2000 |
| WO | WO 00 58472 | 10/2000 |
| WO | WO 01 02568 | 1/2001 |
| WO | WO 01/29221 | 4/2001 |

OTHER PUBLICATIONS

Hillier et al, Genbank Accession No. AI366107.*
Rost, B, "Enzyme function less conserved than anticipated." J. Mol. Biol. (2002) 318(2):595–608.*
Aldimaru et al. (1997) Drosophila CBP is a co-activator of *cubitus interruptus* in hedgehog signalling. Nature. 386:735–738.
Alcedo et al. (1996) The drosophila smoothened gene encodes a seven-pass membrane protein, a pulative receptor for the hedgehog signal. Cell, 86:221–232.
Alexandre et al. (1996) Transcriptional activation of hedgehog target genes in drosophila is mediated directly by the *cubitus interruptus* protein, a member of the GLI family of zinc finger DNA–binding proteins. Genes & Development. 10:2003–2013.
Apelqvist et al. (1997) Sonic hedgehog directs specialized mesoderm differentiation in the Intestine and pancreas. Current Biology. 7:801–804.
Bellusci et al. (1997) Involvement of sonic hedgehog (Shh) in mouse embryonic lung growth and morphogenesis. Development. 124:53–63.
Bigood et al. (1996) Sertoll cell signaling by desert hedgehog regulates the male germline. Current Biology. 6(3):298–304.
Busson et al. (1988) Genetic analysis of viable and lethal fused mutants of drosophila melanogaster. Roux's Arch. Dev. Biol. 197:221–230.
Chen et al. (1996) Dual roles for patched in sequestering and transducing hedgehog. Cell. 87:553–563.

(Continued)

*Primary Examiner*—Jeffrey Fredman
(74) *Attorney, Agent, or Firm*—Elizabeth M. Barnes; Mark T. Kresnak; Knobbe Martens Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

5 Claims, 18 Drawing Sheets

OTHER PUBLICATIONS

Chiang et al. (1996) Cyclopia and defective axial patterning in mice lacking sonic hedgehog gene function. Nature. 383:407–413.

Chidambaram et al. (1996) Mutations in the human homologue of the Drosophila patched gene in Caucasian and African–American nevoid basal cell carcinoma syndrome patients. Cancer Research. 58:4599–4601.

Dominguez et al. (1996) Sending and receiving the hedgehog signal: control by the drosophila Gli protein *cubitus interruptus*. Science. 272:1621–1625.

Echeland et al. (1993) Sonic hedgehog, a member of a family of putative signaling molecules, is implicated in the regulation of CNS polarity. Cell. 75:1417–1430.

Ericson et al. (1995) Sonic hedgehog induces the differentiation of ventral forebrain neurons: a common signal for ventral patterning within the neural tube. Cell. 81:747–758.

Fan and Tessler–Lavigne (1994) Patterning of mammalian somites by surface ectoderm and notochord: evidence for sciarolome induction by a hedgehog homolog. Cell. 79:1176–1186.

Gailani et al. (1996) The role of the human homologue of drosophila patched in sporadic basal cell carcinomas. Nature Genetics, 14:78–81.

Greu and Simpson (1987) The segment polarity gene costal–2 in drosophila. Developmental Biology. 122:186–200.

Hahn et al. (1996) Mutations of the human homolog of drosophila patched in the nevoid basal cell carcinoma syndrome. Cell. 85:841–851.

Hooper and Scott (1989) The drosophila patched gene encodes a putative membrane protein required for segmental patterning. Cell. 59:751–765.

Hynes et al. (1995) Induction of midbrain dopaminergic neurons by sonic hedgehog. Neuron. 15:35–44.

Hynes et al. (1997) Control of cell pattern in the neural tube by the zinc finger transcription factor and oncogene Gli–1, Neuron. 19:15–26.

Ingham (1995) Signalling by hedgehog family proteins in drosophila and vertebrate development. Current Opinion in Genetics and Development. 5:492–496.

Jiang and Struhl (1996) Regulation of the hedgehog and wingless signalling pathways by the F–box/WD40–repeat protein Slimb. Nature. 391:493–496.

Johnson et al. (1994) Ectopic expression of sonic hedgehog alters dorsal–ventral patterning of somites. Cell. 79:1165–1173.

Johnson et al. (1996) Human homolog of patched, a candidate gene for the basal cell nevus syndrome. Science. 272:1668–1671.

Klein et al. (1996) Selection for genes encoding secreted proteins and receptors. Proc. Natl. Acad. Sci. USA. 93:7106–7113.

Krauss et al. (1993) A functionally conserved homolog of the drosophila segment polarity gene hh is expressed in tissues with polarizing activity in zebrafish embryos. Cell. 75:1431–1444.

Krishman et al. (1997) Mediation of sonic hedgehog–induced expression of COUP–TFII by a protein phosphatase. Science. 278:1947–1950.

Laufer et al. (1994) Sonic hedgehog and Fgl–4 act through a signaling cascade and feedback loop to integrate growth and patterning of the developing limb bud. Cell. 79:993–1003.

Lee et al. (1997) Gli1 is a target of sonic hedgehog that induces ventral neural tube development. Development. 124:2537–2552.

Mango et al. (1996) Biochemical evidence that patched is the hedgehog receptor. Nature. 364:176–179.

Marti et al. (1995) Requirement of 19K form of sonic hedgehog for induction of distinct ventral cell types in CNS explants. Nature. 375:322–325.

Nakano et al. (1989) A protein with several possible membrane–spanning domains encoded by the drosophila segment polarity gene patched. Nature. 341:508–513.

Nüsslein–Volhard et al. (1984) Mutations affecting the pattern of the larval cuticle in drosophila melanogaster. Roux's Arch. Dev. Biol. 193:267–282.

Orenic et al. (1990) Cloning and characterization of the segment polarity gene *cubilus–interruptus* dominant of drosophila. Genes & Development. 4:1053–1067.

Oro et al. (1997) Basal cell carcinomas in mice overexpressing sonic hedgehog. Science. 276:817–821.

Perrimon (1995) Hedgehog and beyond. Cell. 80:617–620.

Pham et al. (1995) The suppressor of fused gene encodes a novel PEST protein involved in drosophila segment polarity establishment. Genetics. 140:587–596.

Préat et al. (1990) A putative serine/threonine protein kinase encoded by the segment–polarity fused gene of drosophila. Nature. 347:87–89.

Préat (1992) Characterization of suppressor of fused, a complete suppressor of the fused segment polarity gene of drosophila melanogaster. Genetics. 132:725–736.

Préat et al. (1993) Segmental polarity in drosophila melanogaster: genetic dissection of fused in suppressor of fused background reveals interaction with costal–2. Genetics. 135:1047–1062.

Riddle et al. (1993) Sonic hedgehog mediates the polarizing activity of the ZPA. Cell. 75:1401–1416.

Roberts et al. (1995) Sonic hedgehog is an endodermal signal inducing Bmp–4 and Hox genes during induction and regionalization of the chick hindgut. Development. 121:3163–3174.

Robbins et al. (1997) Hedgehog elicits signal transduction by means of a large complex containing the kinasin–related protein costal2. Cell. 90:225–234.

Roelink et al. (1995) Floor plate and motor neuron induction by different concentrations of the amino–terminal cleavage product of sonic hedgehog autoproteolysis. Cell. 81:445–455.

Simpson and Grau (1987) The segment polarity gene costal–2 in drosophila. Developmental Biology. 122:201–209.

Sisson et al. (1997) Costal2, a novel kinesin–related protein in the hedgehog signaling pathway. Cell. 90:235–245.

Stone et al. (1996) The tumour–suppressor gene patched encodes a candidate receptor for sonic hedgehog. Nature. 364:129–134.

Thérond et al. (1996) Functional domains of fused, a serine–threonine kinase required for signaling in drosophila. Genetics. 142:1181–1198.

Thérond et al. (1996) Phosphorylation of the fused protein kinase in response to signaling from hedgehog. Proc. Natl. Acad. Sci. USA. 93:4224–4226.

Undan et al. (1996) Mutations in the human homologue of drosophila patched (PTCH) in basal cell carcinomas and the gorlin syndrome: different in vivo mechanisms of PTCH inactivation. Cancer Research. 56:4562–4565.

Van den Hauvel and Ingham (1996) Smoothened encodes a receptor–like serpentine protein required for hedgehog signaling. Nature. 382:547–551.

Wicking et al. (1997) Most germ–like mutations in the novoid basal cell carcinoma syndrome lead to a premature termination of the PATCHED protein, and no genotype–phenotype correlations are evident. Am. J. Hum. Genet. 80:21–26.

Xie et al. (1998) Activating smoothened mutations in sporadic basal–cell carcinoma. Nature. 391:90–92.

Database search, Locus list: hum (349,801 seqs, 86, 964, 548.22), Mon Jan 7 16:12.49 2002 [BLASTP 2.2.1 [Jul–12–2001], NCBI]2 pp.

Database search, Locus list: hum—est(1, 803, 435 seqs, 6, 559, 376. 376. 613 bp). Tue Jan 8 09:15:52 2002 [BLASTN 2.2.1 [Jul–12–2001], NCBI]8 pp.

Database EMBL 'Online! (Oct. 31, 1997) Strausberg, R.: np74e04. s1 NCI_CGAP_Br2 Homo sapiens cDNA clone IMAGE: 1132062 3' Database accession No. AA 632131.

Fransen, et al., Identification of peroxisomal proteins by using M13 phage protein VI phage display: molecular evidence that mammalian peroxisomes contain at 2,4–dionoyl–CoA reductase, Biochem. J. 348:561–568 (1999).

Comparison between Accession No. AAY87109 and SEQ ID NO: 23.

Comparison between Accession No. AAY87196 and SEQ ID NO: 23.

Comparison between Accession No. AA025266 and SEQ ID NO: 8.

Comparison between Accession No. AA024389 and SEQ ID NO: 8.

Comparison between Accession No. AX118905 and SEQ ID NO: 8.

Comparison between Accession No. CAC38526.1 and SEQ ID NO: 8.

Comparison between Accession No. AX070106 and SEQ ID NO: 6.

Comparison between Accession No. AAB40784 and SEQ ID NO: 6.

Comparison between Accession No. AAC74993 and SEQ ID NO: 6.

Comparison between Accession No. AI373244 and SEQ ID NO: 6.

Comparison between Accession No. AI366107 and SEQ ID NO: 6.

Comparison between Accession No. AR052531 and SEQ ID NO: 12.

Comparison between Accession No. W63967 and SEQ ID NO: 12.

Comparison between Accession No. AAZ98060 and SEQ ID NO: 23.

Comparison between Accession No. AI08845 and SEQ ID NO: 23.

Comparison between Accession No. AAV88653 and SEQ ID NO: 23.

Database EMBL 'Online ! Entry HSA24389, Aug. 14, 1996, Hillier, L. et al., "ze74b01.r1 Soares$_{13}$ fetal_heart_NbHH19W Homo sapiens cDNA clone IMAGE: 364681 5', mRNA sequence." Database accession No. AA024389 XP002230500.

Database EMBL 'Online! Entry HSA25266, Aug. 14, 1996, Hillier, L. et al. "ze74b01.s1 Soares_fetal_heart_NbHH19W Homo sapiens cDNA cline IMAGE:364681 3', mRNA sequence." Database accession No. AA025266 XP002230501.

Database EMBL [Online] md78c02.r1 Soares mouse embryo NbME1cDNA clone (Jun. 22, 1996) Marra et al., "The WashU–HHMI Mouse EST Protect" Database accession No. MM96732 XP002232923.

Database EBI 'Online! (Aug. 19, 1998) Strausberg R. "qa12e07.x1 NCI_CGAP_Brn23 Homo sapiens cDNA clone Image:1686564 3' similar to contains TAR1.b2 MSR1 repetitive element;, mRNA sequence." Database accession No. AI088845 XP002226252.

Database EMBL [Online] (Jan. 11, 1999) Hillier, L. et al. "ao87d07.x1 Schiller meningoma Homo sapiens cDNA clone IMAGE:1952845 3 similar to contains element TAR1 repetitive element;, mRNA sequence." Database accession No. AI366107 XP002230801.

Database EMBL [Online] (Jan. 13, 1999) Strausberg R. "qz48e01.x1 NCI–CGAP–Kid11 Homo sapiens cDNA clone IMAGE:2030136 3, mRNA sequence." Database accession No. AI373244 XP002230802.

Klein, et al. Selection for genes encoding secreted proteins and receptors, Proc. Natl. Acad. Sci. USA 93:7108–7113 (1996).

Tashiro, et al., Signal sequence trap: a cloning strategy for secreted proteins and type 1 membrane proteins, Science 261:600–603 (1993).

Oligonucleotide properties calculator (http://www.basic.nwu.edu/biotools/oligocalc.html).*

Genbank Accession No. AC004089 (Jan. 30, 1998).*

Genbank Accession Number XM_218828 (2003).*

Allman, et al. 1996. *Blood*, vol. 87, No. 12, pp. 5257–5288.

Alberts, et al. 1994. *Molecular Biology of the Cell, 3rd Edition*, pp. 403–404, 453. New York: Garland Publishing.

Alberts, et al. 2002. *Molecular Biology of the Cell 4th Edition*, pp. 302, 363–364, 379, 435. New York; Garland Publishing.

Alitalo 1984. Amplification of cellular oncogenes in cancer cells. *Med. Biol.*, 62:304–317.

Banhassy, et al. 2004. Cyclin A and cyclin Dl as significant prognostic markers in colorectal cancer patients. *BMC Gastroenterology*, 4:22–34.

Bieche, et al. 1998. Novel Approach to Quantitative Polymerase Chain Reaction Using Real–Time Detection: Application to the Detection of Gene Amplification in Breast Cancer, *Int. J. Cancer*. 78:661–666.

Blancato, et al. 2004. Correlation of amplification and overexpression of the c–*myc* oncogene in high–grade breast cancer: FISH, *in situ* hybridization and immunohistochemical analyses. *British Journal of Cancer*, 90(8), 1612–1619.

Chen, et al. 2002. Discordant Protein and mRNA Expression in Lung Adenocarcinomas. *Molecular & Cellular Proteomics 1.4*, 304–313.

Fu, et al. 1996. Translational regulation of human p53 gene expression. *The EMBO Journal*, vol. 15, No. 16, pp. 4392–4401.

Gökmen–Polar, et al., Feb. 2001, Elevated Protein Kinase C βII is an Early Promotive Event in Colon Carcinogenesis, *Cancer Research*, vol. 61, pp. 1375–1381.

Grimaldi, et al. 1989. The t(5;14) chromosomal translocation in a case of acute lymphocytic leukemia joins the interleukin–3 gene to the immunoglobulin heavy chain gene. *Blood*, 73(8):2081–2085.

Gygi, et al. Mar. 1999. Correlation between Protein and mRNA Abundance in Yeast. *Molecular and Cellular Biology*, 1720–1730.

Hancock, W. S. 2004. Do we have enough biomarkers? *Journal of Proteome Research*, 3(4):685.

Hanna, et al. Aug. 1999. HER–2/neu breast cancer predictive testing. *Pathology Associates Medical Laboratories*.

Haynes, et al., 1988, Proteome analysis: Biological assay of data archieve? *Electrophoresis*, vol. 19, pp. 1862–1871.

Heid, et al. 1996. Real Time Quantitative PCR. Genome Res. 6:986–994.

Higuchi, et al. Apr. 1992. Simultaneous Amplification and Detection of Specific DNA Sequences. *Biotechnology*, 10:413–417

Hu, et al. 2003. Analysis of Genomic and Proteomic Data Using Advanced Literature Mining. *Journal of Proteome Research*, vol. 2, pp. 405–412.

Hyman et al. Nov. 2002. Impact of DNA Amplification of Gene Expression Patterns. *Cancer Research*, 62:6240–6245.

Jang A. Hill RP, Sep. 1997. An examination of the effects of hypoxia, acidosis, and glucose starvation on the expression of metastatsis–associated genes in murine tumor cells. *Clin. Exp. Metastatsis 15(5)*: pp. 469–483.

Konopka, et al. Jun. 1986. Variable Expression of the Translocated c–abl Oncogene in Philadelphia–Chromosome–Positive B–Lymphoid Cell Lines from Chronic Myelogeneous Leukemia Patients, *National Academy of Sciences of the United States of America*, vol. 83, No. 11, pp. 4049–4052.

Lewin, B. 1994. Oncogenes: Gene Expression and Cancer, Chap. 39, pp. 1196–1201. *Genes V*. New York: Oxford University Press.

Lewin, B. 1997. Regulation of Transaction, Chap. 29, pp. 847–848. *Genes VI*. New York: Oxford University Press.

Livak, et al. 1995. Oligonucleotides with Fluerescen Dyes at Opposite Ends Provide a Quenced Probe Statem Useful for Detectin PCR Product and Nucleic Acid Hybridization. *PCR Methods Appl* 4:357–362.

Meeker, et al. 1990. Activation of the interleukin–3 gene by chromosome translocation in acute lymphocytic leukemia with eosinophilia. *Blood*, 76(2):285–289.

Meric, et al. 2002. Translation initiation in cancer: A novel target for therapy. *Molecular Cancer Therapeutics*, 1:971–979.

Merlino, et al. 1985. Elevated Epidermal Growth Factor Receptor Gene Copy Number and Expression in a Squamous Carcinoma Cell Line. *J. Clin. Invest.*, 75:1077–1079.

Ohara, et al. 2001. Directional cDNA library construction assisted by the in vitro recombination reaction. *Nucleic Acids Research*, vol. 29, No. e22, pp. 1–8.

Ørntoft, et al. 2002. Genome–wide study of gene copy numbers, transcripts, and protein levels in pairs of non–invasive and invasive human transitional cell carcinomas. *Molecular & Cellular Proteomics*, 1:37–45.

Pennica, et al. 1998. WISP genes are members of the connective tissue growth factor family that are up–regulated in Wnt–1 transformed cells and aberrantly expressed in human colon tumors. *Proc. Natl. Acad. Sci. USA*. 95(25):14717–14722.

Pitti, et al., 1998. Genomic amplification of a decoy receptor for Fas ligand in lung and colon cancer. *Nature*. 396(6712):699–703.

Pollock, et al. 2002. Microarray analysis reveals a major direct role of DNA copy number alteration in the transcriptional program of human breast tumors. *PNAS*, 99(20):12963–12968.

Powell, et al. Oct. 1998. Expression of cytochrome P4502E1 in human liver: assessment by mRNA, genotype and phenotype. *Pharmaceogenetics*, vol. 5: pp. 411–421.

Singleton, et al. 1992. Clinical and pathologic significance of the c–erb–B–2 (*HER–2/neu*) oncogene. Pathol. Annu, 1(27):165–190.

Vallejo, et al. Dec. 2000. Evidence of tissue–specific, post–transcriptional regulation of NRF–2 expression. *Biochimie* 82(12): 1129–33.

Wang, et al. 1996. mRNA differential display: Application in the discovery of novel pharmacological targets, *TIPS*, 17:276–279.

Zhigang, et al. 2004. Prostate stem cell antigen (PSCA) expression in human prostate cancer tissues and its potential role in prostate carcinogenesis and progression of prostate cancer. *World Journal of Surgical Oncology*, 2:13.

\* cited by examiner

FIGURE 1

CGGACGCGTGGGACCCATACTTGCTGGTCTGATCCATGCACAAGGCGGGGCTGCTAGGCCTC
TGTGCCCGGGCTTGGAATTCGGTGCGGATGGCCAGCTCCGGGATGACCCGCCGGGACCCGCT
CGCAAATAAGGTGGCCCTGGTAACGGCCTCCACCGACGGGATCGGCTTCGCCATCGCCCGGC
GTTTGGCCCAGGACGGGGCCCATGTGGTCGTCAGCAGCCGGAAGCAGCAGAATGTGGACCAG
GCGGTGGCCACGCTGCAGGGGAGGGGCTGAGCGTGACGGGCACCGTGTGCCATGTGGGGAA
GGCGGAGGACCGGGAGCGGCTGGTGGCCACGGCTGTGAAGCTTCATGGAGGTATCGATATCC
TAGTCTCCAATGCTGCTGTCAACCCTTTCTTTGGAAGCATAATGGATGTCACTGAGGAGGTG
TGGGACAAGACTCTGGACATTAATGTGAAGGCCCCAGCCCTGATGACAAAGGCAGTGGTGCC
AGAAATGGAGAAACGAGGAGGCGGCTCAGTGGTGATCGTGTCTTCCATAGCAGCCTTCAGTC
CATCTCCTGGCTTCAGTCCTTACAATGTCAGTAAAACAGCCTTGCTGGGCCTGACCAAGACC
CTGGCCATAGAGCTGGCCCCAAGGAACATTAGGGTGAACTGCCTAGCACCTGGACTTATCAA
GACTAGCTTCAGCAGGATGCTCTGGATGGACAAGGAAAAGAGGAAAGCATGAAAGAAACCC
TGCGGATAAGAAGGTTAGGCGAGCCAGAGGATTGTGCTGGCATCGTGTCTTTCCTGTGCTCT
GAAGATGCCAGCTACATCACTGGGGAAACAGTGGTGGTGGGTGGAGGAACCCCGTCCCGCCT
CTGAGGACCGGGAGACAGCCCACAGGCCAGAGTTGGGCTCTAGCTCCTGGTGCTGTTCCTGC
ATTCACCCACTGGCCTTTCCCACCTCTGCTCACCTTACTGTTCACCTCATCAAATCAGTTCT
GCCCTGTGAAAAGATCCAGCCTTCCCTGCCGTCAAGGTGGCGTCTTACTCGGGATTCCTGCT
GTTGTTGTGGCCTTGGGTAAAGGCCTCCCCTGAGAACACAGGACAGGCCTGCTGACAAGGCT
GAGTCTACCTTGGCAAAGACCAAGATATTTTTTCCTGGGCCACTGGTGAATCTGAGGGGTGA
TGGGAGAGAAGGAACCTGGAGTGGAAGGAGCAGAGTTGCAAATTAACAGCTTGCAAATGAGG
TGCAAATAAAATGCAGATGATTGCGCGGCTTTGAAAAAAAAAA

FIGURE 2

```
></usr/seqdb2/sst/DNA/Dnaseqs.min/ss.DNA35672
><subunit 1 of 1, 278 aa, 1 stop
><MW: 29537, pI: 8.97, NX(S/T): 1
MHKAGLLGLCARAWNSVRMASSGMTRRDPLANKVALVTASTDGIGFAIARRLAQDGAHVVVS
SRKQQNVDQAVATLQGEGLSVTGTVCHVGKAEDRERLVATAVKLHGGIDILVSNAAVNPFFG
SIMDVTEEVWDKTLDINVKAPALMTKAVVPEMEKRGGGSVVIVSSIAAFSPSPGFSPYNVSK
TALLGLTKTLAIELAPRNIRVNCLAPGLIKTSFSRMLWMDKEKEESMKETLRIRRLGEPEDC
AGIVSFLCSEDASYITGETVVVGGGTPSRL
```

Important features of the protein:
Signal peptide:
amino acids 1-15

N-glycosylation site.
amino acids 183-186

N-myristoylation sites.
amino acids 43-48, 80-85, 191-196, 213-218, 272-277

Microbodies C-terminal targeting signal.
amino acids 276-278

FIGURE 3

```
GCGCCCTGAGCTCCGCCTCCGGGCCCGATAGCGGCATCGAGAGCGCCTCCGTCGAGGACCAGGCGGCG
CAGGGGGCCGGCGGGCGAAAGGAGGATGAGGGGGCGCAGCAGCTGCTGACCCTGCAGAACCAGGTGGC
GCGGCTGGAGGAGGAGAACCGAGACTTTCTGGCTGCGCTGGAGGACGCCATGGAGCAGTACAAACTGC
AGAGCGACCGGCTGCGTGAGCAGCAGGAGGAGATGGTGGAACTGCGGCTGCGGTTAGAGCTGGTGCGG
CCAGGCTGGGGGGGCCTGCGGCTCCTGAATGGCCTGCCTCCCGGGTCCTTTGTGCCTCGACCTCATAC
AGCCCCCCTGGGGGGTGCCCACGCCCATGTGCTGGGCATGGTGCCGCCTGCCTGCCTCCCTGGAGATG
AAGTTGGCTCTGAGCAGAGGGGAGAGCAGGTGACAAATGGCAGGGAGGCTGGAGCTGAGTTGCTGACT
GAGGTGAACAGGCTGGGAAGTGGCTCTTCAGCTGCTTCAGAGGAGGAAGAGGAGGAGGAGGAGCCGCC
CAGGCGGACCTTACACCTGCGCAGAAATAGGATCAGCAACTGCAGTCAGAGGGCGGGGCACGCCCAG
GGAGTCTGCCAGAGAGGAAGGGCCCAGAGCTTTGCCTTGAGGAGTTGGATGCAGCCATTCCAGGGTCC
AGAGCAGTTGGTGGGAGCAAGGCCCGAGTTCAGGCCCGCCAGGTCCCCCTGCCACAGCCTCAGAGTG
GCGGCTGGCCCAGGCCCAGCAGAAGATCCGGGAGCTGGCTATCAACATCCGCATGAAGGAGGAGCTTA
TTGGCGAGCTGGTCCGCACAGGAAAGGCAGCTCAGGCCCTGAACCGCCAGCACAGCCAGCGTATCCGG
GAGCTGGAGCAGGAGGCAGAGCAGGTGCGGGCCGAGCTGAGTGAAGGCCAGAGGCAGCTGCGGGAGCT
CGAGGGCAAGGAGCTCCAGGATGCTGGCGAGCGGTCTCGGCTCCAGGAGTTCCGCAGGAGGGTCGCTG
CGGCCCAGAGCCAGGTGCAGGTGCTGAAGGAGAAGAAGCAGGCTACGGAGCGGCTGGTGTCACTGTCG
GCCCAGAGTGAGAAGCGACTGCAGGAGCTCGAGCGGAACGTGCAGCTCATGCGGCAGCAGCAGGGACA
GCTGCAGAGGCGGCTTCGCGAGGAGACGGAGCAGAAGCGGCGCCTGGAGGCAGAAATGAGCAAGCGGC
AGCACCGCGTCAAGGAGCTGGAGCTGAAGCATGAGCAACAGCAGAAGATCCTGAAGATTAAGACGGAA
GAGATCGCGGCCTTCCAGAGGAAGAGGCGCAGTGGCAGCAACGGCTCTGTGGTCAGCCTGGAACAGCA
GCAGAAGATTGAGGAGCAGAAGAAGTGGCTGGACCAGGAGATGGAGAAGGTGCTACAGCAGCGGCGGG
CGCTGGAGGAGCTGGGGGAGGAGCTCCACAAGCGGGAGGCCATCCTGGCCAAGAAGGAGCCCTGATG
CAGGAGAAGACGGGGCTGGAGAGCAAGCGCCTGAGATCCAGCCAGGCCCTCAACGAGGACATCGTGCG
AGTGTCCAGCCGGCTGGAGCACCTGGAGAAGGAGCTGTCCGAGAAGAGCGGGCAGCTGCGGCAGGGCA
GCGCCCAGAGCCAGCAGCAGATCCGCGGGGAGATCGACAGCCTGCGCCAGGAGAAGGACTCGCTGCTC
AAGCAGCGCCTGGAGATCGACGGCAAGCTGAGGCAGGGGAGTCTGCTGTCCCCGAGGAGGAGCGGAC
GCTGTTCCAGTTGGATGAGGCCATCGAGGCCCTGGATGCTGCCATTGAGTATAAGAATGAGGCCATCA
CATGCCGCCAGCGGGTGCTTCGGGCCTCAGCCTCGTTGCTGTCCCAGTGCGAGATGAACCTCATGGCC
AAGCTCAGCTACCTCTCATCCTCAGAGACCAGAGCCCTCCTCTGCAAGTATTTTGACAAGGTGGTGAC
GCTCCGAGAGGAGCAGCACCAGCAGCAGATTGCCTTCTCGGAACTGGAGATGCAGCTGGAGGAGCAGC
AGAGGCTGGTGTACTGGCTGGAGGTGGCCCTGGAGCGGCAGCGCCTGGAGATGGACCGCCAGCTGACC
CTGCAGCAGAAGGAGCACGAGCAGAACATGCAGCTGCTCCTGCAGCAGAGTCGAGACCACCTCGGTGA
AGGGTTAGCAGACAGCAGGAGGCAGTATGAGGCCCGGATTCAAGCTCTGGAGAAGGAACTGGGCCGTT
ACATGTGGATAAACCAGGAACTGAAACAGAAGCTCGGCGGTGTGAACGCTGTAGGCCACAGCAGGGGT
GGGGAGAAGAGGAGCCTGTGCTCGGAGGGCAGACAGGCTCCTGGAAATGAAGATGAGCTCCACCTGGC
ACCCGAGCTTCTCTGGCTGTCCCCCCTCACTGAGGGGGCCCCCGCACCCGGGAGGAGACGCGGGACT
TGGTCCACGCTCCGTTACCCTTGACCTGGAAACGCTCGAGCCTGTGTGGTGAGGAGCAGGGGTCCCCC
GAGGAACTGAGGCAGCGGGAGGCGGCTGAGCCCCTGGTGGGGCGGGTGCTTCCTGTGGGTGAGGCAGG
CCTGCCCTGGAACTTTGGGCCTTTGTCCAAGCCCCGGCGGGAACTGCGACGAGCCAGCCCGGGGATGA
TTGATGTCCGGAAAAACCCCCTGTAAGCCCTCGGGGCAGACCCTGCCTTGGAGGGAGACTCCGAGCCT
GCTGAAAGGGCAGCTGCCTGTTTTGCTTCTGTGAAGGGCAGTCCTTACCGCACACCCTAAATCCAGG
CCCTCATCTGTACCCTCACTGGGATCAACAAATTTGGGCCATGGCCCAAAAGAACTGGACCCTCATTT
AACAAAATAATATGCAAATTCCCACCACTTACTTCCATGAAGCTGTGGTACCCAATTGCCGCCTTGTG
TCTTGCTCGAATCTCAGGACAATTCTGGTTTCAGGCGTAAATGGATGTGCTTGTAGTTCAGGGGTTTG
GCCAAGAATCATCACGAAAGGGTCGGTGGCAACCAGGTTGTGGTTTAAATGGTCTTATGTATATAGGG
GAAACTGGGAGACTTTAGGATCTTAAAAAACCATTTAATAAAAAAAAATCTTTGAAGGGAC
```

FIGURE 4

```
</usr/seqdb2/sst/DNA/Dnaseqs.min/ss.DNA47465
<subunit 1 of 1, 830 aa, 1 stop
<MW: 95029, pI: 8.26, NX(S/T): 2
MEQYKLQSDRLREQQEEMVELRLRLELVRPGWGGLRLLNGLPPGSFVPRPHTAPLGGAHAHV
LGMVPPACLPGDEVGSEQRGEQVTNGREAGAELLTEVNRLGSGSSAASEEEEEEEPPRRTL
HLRRNRISNCSQRAGARPGSLPERKGPELCLEELDAAIPGSRAVGGSKARVQARQVPPATAS
EWRLAQAQQKIRELAINIRMKEELIGELVRTGKAAQALNRQHSQRIRELEQEAEQVRAELSE
GQRQLRELEGKELQDAGERSRLQEFRRRVAAAQSQVQVLKEKKQATERLVSLSAQSEKRLQE
LERNVQLMRQQQGQLQRRLREETEQKRRLEAEMSKRQHRVKELELKHEQQQKILKIKTEEIA
AFQRKRRSGSNGSVVSLEQQQKIEEQKKWLDQEMEKVLQQRRALEELGEELHKREAILAKKE
ALMQEKTGLESKRLRSSQALNEDIVRVSSRLEHLEKELSEKSGQLRQGSAQSQQQIRGEIDS
LRQEKDSLLKQRLEIDGKLRQGSLLSPEEERTLFQLDEAIEALDAAIEYKNEAITCRQRVLR
ASASLLSQCEMNLMAKLSYLSSSETRALLCKYFDKVVTLREEQHQQQIAFSELEMQLEEQQR
LVYWLEVALERQRLEMDRQLTLQQKEHEQNMQLLLQQSRDHLGEGLADSRRQYEARIQALEK
ELGRYMWINQELKQKLGGVNAVGHSRGGEKRSLCSEGRQAPGNEDELHLAPELLWLSPLTEG
APRTREETRDLVHAPLPLTWKRSSLCGEEQGSPEELRQREAAEPLVGRVLPVGEAGLPWNFG
PLSKPRRELRRASPGMIDVRKNPL Important features:
Leucine zipper pattern.
amino acids 557-579, 794-815

N-glycosylation sites.
amino acids 133-136, 383-386

Kinesin related protein Kif-4 Coiled-coil domain:
amino acids 231-672
```

FIGURE 5

ATTCTCCTAGAGCATCTTTGGAAGCATGAGGCCACGATGCTGCATCTTGGCTCTTGTCTGCT
GGATAACAGTCTTCCTCCTCCAGTGTTCAAAAGGAACTACAGACGCTCCTGTTGGCTCAGGA
CTGTGGCTGTGCCAGCCGACACCCAGGTGTGGGAACAAGATCTACAACCCTTCAGAGCAGTG
CTGTTATGATGATGCCATCTTATCCTTAAAGGAGACCCGCCGCTGTGGCTCCACCTGCACCT
TCTGGCCCTGCTTTGAGCTCTGCTGTCCCGAGTCTTTTGGCCCCCAGCAGAAGTTTCTTGTG
AAGTTGAGGGTTCTGGGTATGAAGTCTCAGTGTCACTTATCTCCCATCTCCCGGAGCTGTAC
CAGGAACAGGAGGCACGTCCTGTACCCATAAAACCCCAGGCTCCACTGGCAGACGGCAGAC
AAGGGGAGAAGAGACGAAGCAGCTGGACATCGGAGACTACAGTTGAACTTCGGAGAGAAGCA
ACTTGACTTCAGAGGGATGGCTCAATGACATAGCTTTGGAGAGGAGCCCAGCTGGGGATGGC
CAGACTTCAGGGGAAGAATGCCTTCCTGCTTCATCCCCTTTCCAGCTCCCCTTCCCGCTGAG
AGCCACTTTCATCGGCAATAAAATCCCCCACATTTACCATCT

FIGURE 6

></usr/seqdb2/sst/DNA/Dnaseqs.full/ss.DNA57700
><subunit 1 of 1, 125 aa, 1 stop
><MW: 14198, pI: 9.01, NX(S/T): 1

MRPRCCILALVCWITVFLLQCSKGTTDAPVGSGLWLCQPTPRCGNKIYNPSEQCCYDDAILS
LKETRRCGSTCTFWPCFELCCPESFGPQQKFLVKLRVLGMKSQCHLSPISRSCTRNRRHVLYP

Important features:
Signal sequence
amino acids 1-21

N-myristoylation sites.
amino acids 33-39, 70-76

FIGURE 7

CCCACGCGTCCGCCCACGCGTCCGGGTGCCACTCGCGCGCCGGCCGCGCTCCGGGCTTCTCT
TTTCCCTCCGACGCGCCACGGCTGCCCAGACATTCCGGCTGCCGGGTCTGGAGAGCTCCCCG
AACCCCTCCGCGGAGAGGAGCGAGGCGGCGCCAGGGTGGCCCCCGGGGCGCGCTTGGTCTCG
GAGAAGCGGGGACGAGGCCGGAGGATGAGCGACTGAGGGCGACGCGGGCACTGACGCGAGTT
GGGGCCGCGACTACCGGCAGCTGACAGCGCGATGAGCGACTCCCCAGAGACGCCCTAGCCCG
GTGTGCGCGCCAGGCGGAGCGCGCAGGTGGGGCTGGGCTGTTAGTGGTCCGCCCCACGCGGG
TCGCCGGCCGGCCCAGGATGGGCGCTGGCAACCCGGGCCCGCGCCCGCCGCTGCTACCCCTG
CGCCCGCTGCGAGCCCGGCGTCCGGCCCGCGCCCTGCGCTCATGGACGGCGGCTCCCGGCTG
GCGGCGGCGCGCCCCGGGCTGTGAATGCGACTCGCCCCTCGGCCGCGCTCCCCGCCCGCCC
GCCCGCCGGGACGTGGTAGGGGATGCCCAGCTCCACTGCGATGGCAGTTGGCGCGCTCTCCA
GTTCCCTCCTGGTCACCTGCTGCCTGATGGTGGCTCTGTGCAGTCCGAGCATCCCGCTGGAG
AAGCTGGCCCAGGCACCAGAGCAGCCGGGCCAGGAGAAGCGTGAGCACGCCACTCGGGACGG
CCCGGGGCGGGTGAACGAGCTCGGGCGCCCGGCGAGGGACGAGGGCGGCAGCGGCCGGGACT
GGAAGAGCAAGAGCGGCCGTGGGCTCGCCGGCCGTGAGCCGTGGAGCAAGCTGAAGCAGGCC
TGGGTCTCCCAGGGCGGGGGCGCCAAGGCCGGGGATCTGCAGGTCCGGCCCCGCGGGGACAC
CCCGCAGGCGGAAGCCCTGGCCGCAGCCGCCCAGGACGCGATTGGCCCGGAACTCGCGCCCA
CGCCCGAGCCACCCGAGGAGTACGTGTACCCGGACTACGTGGCAAGGGCTGCGTGGACGAG
AGCGGCTTCGTGTACGCGATCGGGGAGAAGTTCGCGCCGGGCCCCTCGGCCTGCCCGTGCCT
GTGCACCGAGGAGGGGCCGCTGTGCGCGCAGCCCGAGTGCCCGAGGCTGCACCCGCGCTGCA
TCCACGTCGACACGAGCCAGTGCTGCCCGCAGTGCAAGGAGAGGAAGAACTACTGCGAGTTC
CGGGGCAAGACCTATCAGACTTTGGAGGAGTTCGTGGTGTCTCCATGCGAGAGGTGTCGCTG
TGAAGCCAACGGTGAGGTGCTATGCACAGTGTCAGCGTGTCCCCAGACGGAGTGTGTGGACC
CTGTGTACGAGCCTGATCAGTGCTGTCCCATCTGCAAAAATGGTCCAAACTGCTTTGCAGAA
ACCGCGGTGATCCCTGCTGGCAGAGAAGTGAAGACTGACGAGTGCACCATATGCCACTGTAC
TTATGAGGAAGGCACATGGAGAATCGAGCGGCAGGCCATGTGCACGAGACATGAATGCAGGC
AAATGTAGACGCTTCCCAGAACACAAACTCTGACTTTTTCTAGAACATTTTACTGATGTGAA
CATTCTAGATGACTCTGGGAACTATCAGTCAAAGAAGACTTTTGATGAGGAATAATGGAAAA
TTGTTGGTACTTTTCCTTTTCTTGATAACAGTTACTACAACAGAAGGAAATGGATATATTTC
AAAACATCAACAAGAACTTTGGGCATAAAATCCTTCTCTAAATAAATGTGCTATTTTCACAG
TAAGTACACAAAAGTACACTATTATATATCAAATGTATTTCTATAATCCCTCCATTAGAGAG
CTTATATAAGTGTTTTCTATAGATGCAGATTAAAAATGCTGTGTTGTCAACCGTCAAAAAAA
AAAAAAAAAAAAAAAAAAA

FIGURE 8

></usr/seqdb2/sst/DNA/Dnaseqs.min/ss.DNA68818
><subunit 1 of 1, 325 aa, 1 stop
><MW: 35296, pI: 5.37, NX(S/T): 0
MPSSTAMAVGALSSSLLVTCCLMVALCSPSIPLEKLAQAPEQPGQEKREHATRDGPGRVNEL
GRPARDEGGSGRDWKSKSGRGLAGREPWSKLKQAWVSQGGGAKAGDLQVRPRGDTPQAEALA
AAAQDAIGPELAPTPEPPEEYVYPDYRGKGCVDESGFVYAIGEKFAPGPSACPCLCTEEGPL
CAQPECPRLHPRCIHVDTSQCCPQCKERKNYCEFRGKTYQTLEEFVVSPCERCRCEANGEVL
CTVSACPQTECVDPVYEPDQCCPICKNGPNCFAETAVIPAGREVKTDECTICHCTYEEGTWR
IERQAMCTRHECRQM Important features of the protein:
Signal peptide:
amino acids 1-27

Transmembrane domain:
amino acids 11-30

Glycosaminoglycan attachment site.
amino acids 80-83

N-myristoylation sites.
amino acids 10-15, 102-107, 103-108

Cell attachment sequence.
amino acids 114-117

EGF-like domain cysteine pattern signature.
amino acids 176-187

FIGURE 9

CAGCCACAGACGGGTCATGAGCGCGGTATTACTGCTGGCCCTCCTGGGGTTCATCCTCCCAC
TGCCAGGAGTGCAGGCGCTGCTCTGCCAGTTTGGGACAGTTCAGCATGTGTGGAAGGTGTCC
GACCTACCCCGGCAATGGACCCCTAAGAACACCAGCTGCGACAGCGGCTTGGGGTGCCAGGA
CACGTTGATGCTCATTGAGAGCGGACCCCAAGTGAGCCTGGTGCTCTCCAAGGGCTGCACGG
AGGCCAAGGACCAGGAGCCCCGCGTCACTGAGCACCGGATGGGCCCCGGCCTCTCCCTGATC
TCCTACACCTTCGTGTGCCGCCAGGAGGACTTCTGCAACAACCTCGTTAACTCCCTCCCGCT
TTGGGCCCCACAGCCCCCAGCAGACCCAGGATCCTTGAGGTGCCCAGTCTGCTTGTCTATGG
AAGGCTGTCTGGAGGGGACAACAGAAGAGATCTGCCCCAAGGGGACCACACACTGTTATGAT
GGCCTCCTCAGGCTCAGGGGAGGAGGCATCTTCTCCAATCTGAGAGTCCAGGGATGCATGCC
CCAGCCAGGTTGCAACCTGCTCAATGGGACACAGGAAATTGGGCCCGTGGGTATGACTGAGA
ACTGCAATAGGAAAGATTTTCTGACCTGTCATCGGGGACCACCATTATGACACACGGAAAC
TTGGCTCAAGAACCCACTGATTGGACCACATCGAATACCGAGATGTGCGAGGTGGGCAGGT
GTGTCAGGAGACGCTGCTGCTCATAGATGTAGGACTCACATCAACCCTGGTGGGGACAAAAG
GCTGCAGCACTGTTGGGGCTCAAAATTCCCAGAAGACCACCATCCACTCAGCCCCTCCTGGG
GTGCTTGTGGCCTCCTATACCCACTTCTGCTCCTCGGACCTGTGCAATAGTGCCAGCAGCAG
CAGCGTTCTGCTGAACTCCCTCCCTCCTCAAGCTGCCCCTGTCCCAGGAGACCGGCAGTGTC
CTACCTGTGTGCAGCCCCTTGGAACCTGTTCAAGTGGCTCCCCCCGAATGACCTGCCCCAGG
GGCGCCACTCATTGTTATGATGGGTACATTCATCTCTCAGGAGGTGGGCTGTCCACCAAAAT
GAGCATTCAGGGCTGCGTGGCCCAACCTTCCAGCTTCTTGTTGAACCACACCAGACAAATCG
GGATCTTCTCTGCGCGTGAGAAGCGTGATGTGCAGCCTCCTGCCTCTCAGCATGAGGGAGGT
GGGGCTGAGGGCCTGGAGTCTCTCACTTGGGGGTGGGCTGGCACTGGCCCCAGCGCTGTG
GTGGGGAGTGGTTTGCCCTTCCTGCTAACTCTATTACCCCACGATTCTTCACCGCTGCTGA
CCACCCACACTCAACCTCCCTCTGACCTCATAACCTAATGGCCTTGGACACCAGATTCTTTC
CCATTCTGTCCATGAATCATCTTCCCCACACACAATCATTCATATCTACTCACCTAACAGCA
ACACTGGGGAGAGCCTGGAGCATCCGGACTTGCCCTATGGGAGAGGGGACGCTGGAGGAGTG
GCTGCATGTATCTGATAATACAGACCCTGTCCTTTCA

FIGURE 10

></usr/seqdb2/sst/DNA/Dnaseqs.min/ss.DNA59847
><subunit 1 of 1, 437 aa, 1 stop
><MW: 46363, pI: 6.22, NX(S/T): 3

MSAVLLLALLGFILPLPGVQALLCQFGTVQHVWKVSDLPRQWTPKNTSCDSGLGCQDTLMLI
ESGPQVSLVLSKGCTEAKDQEPRVTEHRMGPGLSLISYTFVCRQEDFCNNLVNSLPLWAPQP
PADPGSLRCPVCLSMEGCLEGTTEEICPKGTTHCYDGLLRLRGGGIFSNLRVQGCMPQPGCN
LLNGTQEIGPVGMTENCNRKDFLTCHRGTTIMTHGNLAQEPTDWTTSNTEMCEVGQVCQETL
LLIDVGLTSTLVGTKGCSTVGAQNSQKTTIHSAPPGVLVASYTHFCSSDLCNSASSSSVLLN
SLPPQAAPVPGDRQCPTCVQPLGTCSSGSPRMTCPRGATHCYDGYIHLSGGGLSTKMSIQGC
VAQPSSFLLNHTRQIGIFSAREKRDVQPPASQHEGGGAEGLESLTWGVGLALAPALWWGVVCPSC

Important features of the protein:
Signal peptide:
amino acids 1-15

Transmembrane domain:
amino acids 243-260

N-glycosylation sites.
amino acids 46-49, 189-192, 382-385

Glycosaminoglycan attachment sites.
amino acids 51-54, 359-362

N-myristoylation sites.
amino acids 54-59, 75-80, 141-146, 154-159, 168-173, 169-174,
198-203, 254-259, 261-266, 269-274, 284-289, 333-338, 347-352,
360-365, 361-366, 388-393, 408-413, 419-424

FIGURE 11

```
CGACGATGCTACGCGCGCCCGGCTGCCTCCTCCGGACCTCCGTAGCGCCTGCCGCGGCCCTG
GCTGCGGCGCTGCTCTCGTCGCTTGCGCGCTGCTCTCTTCTAGAGCCGAGGGACCCGGTGGC
CTCGTCGCTCAGCCCCTATTTCGGCACCAAGACTCGCTACGAGGATGTCAACCCCGTGCTAT
TGTCGGCCCCGAGGCTCCGTGGCGGGACCCTGAGCTGCTGGAGGGGACCTGCACCCCGGTG
CAGCTGGTCGCCCTCATTCGCCACGGCACCCGCTACCCCACGGTCAAACAGATCCGCAAGCT
GAGGCAGCTGCACGGGTTGCTGCAGGCCCGCGGGTCCAGGGATGGCGGGGCTAGTAGTACCG
GCAGCCGCGACCTGGGTGCAGCGCTGGCCGACTGGCCTTTGTGGTACGCGGACTGGATGGAC
GGGCAGCTAGTAGAGAAGGGACGGCAGGATATGCGACAGCTGGCGCTGCGTCTGGCCTCGCT
CTTCCCGGCCCTTTTCAGCCGTGAGAACTACGGCCGCCTGCGGCTCATCACCAGTTCCAAGC
ACCGCTGCATGGATAGCAGCGCCGCCTTCCTGCAGGGGCTGTGGCAGCACTACCACCCTGGC
TTGCCGCCGCCGGACGTCGCAGATATGGAGTTTGGACCTCCAACAGTTAATGATAAACTAAT
GAGATTTTTTGATCACTGTGAGAAGTTTTTAACTGAAGTAGAAAAAAATGCTACAGCTCTTT
ATCACGTGGAAGCCTTCAAAACTGGACCAGAAATGCAGAACATTTTAAAAAAAGTTGCAGCT
ACTTTGCAAGTGCCAGTAAATGATTTAAATGCAGATTTAATTCAAGTAGCCTTTTTCACCTG
TTCATTTGACCTGGCAATTAAAGGTGTTAAATCTCCTTGGTGTGATGTTTTTGACATAGATG
ATGCAAAGGTATTAGAATATTTAAATGATCTGAAACAATATTGGAAAAGAGGATATGGGTAT
ACTATTAACAGTCGATCCAGCTGCACCTTGTTTCAGGATATCTTTCAGCACTTGGACAAAGC
AGTTGAACAGAAACAAAGGTCTCAGCCAATTTCTTCTCCAGTCATCCTCCAGTTTGGTCATG
CAGAGACTCTTCTTCCACTGCTTTCTCTCATGGGCTACTTCAAAGACAAGGAACCCCTAACA
GCGTACAATTACAAAAAACAAATGCATCGGAAGTTCCGAAGTGGTCTCATTGTACCTTATGC
CTCGAACCTGATATTTGTGCTTTACCACTGTGAAAATGCTAAGACTCCTAAAGAACAATTCC
GAGTGCAGATGTTATTAAATGAAAAGGTGTTACCTTTGGCTTACTCACAAGAAACTGTTTCA
TTTTATGAAGATCTGAAGAACCACTACAAGGACATCCTTCAGAGTTGTCAAACCAGTGAAGA
ATGTGAATTAGCAAGGGCTAACAGTACATCTGATGAACTATGAGTAACTGAAGAACATTTTT
AATTCTTTAGGAATCTGCAATGAGTGATTACATGCTTGTAATAGGTAGGCAATTCCTTGATT
ACAGGAAGCTTTTATATTACTTGAGTATTTCTGTCTTTTCACAGAAAAACATTGGGTTTCTC
TCTGGGTTTGGACATGAAATGTAAGAAAAGATTTTTCACTGGAGCAGCTCTCTTAAGGAGAA
ACAAATCTATTTAGAGAAACAGCTGGCCCTGCAAATGTTTACAGAAATGAAATTCTTCCTAC
TTATATAAGAAATCTCACACTGAGATAGAATTGTGATTTCATAATAACACTTGAAAAGTGCT
GGAGTAACAAAATATCTCAGTTGGACCATCCTTAACTTGATTGAACTGTCTAGGAACTTTAC
AGATTGTTCTGCAGTTCTCTCTTCTTTTCCTCAGGTAGGACAGCTCTAGCATTTTCTTAATC
AGGAATATTGTGGTAAGCTGGGAGTATCACTCTGGAAGAAAGTAACATCTCCAGATGAGAAT
TTGAAACAAGAAACAGAGTGTTGTAAAAGGACACCTTCACTGAAGCAAGTCGGAAAGTACAA
TGAAAATAAATATTTTTGGTATTTATTTATGAAATATTTGAACATTTTTTCAATAATTCCTT
TTTACTTCTAGGAAGTCTCAAAAGACCATCTTAAATTATTATATGTTTGGACAATTAGCAAC
AAGTCAGATAGTTAGAATCGAAGTTTTTCAAATCCATTGCTTAGCTAACTTTTTCATTCTGT
CACTTGGCTTCGATTTTTATATTTTCCTATTATATGAAATGTATCTTTTGGTTGTTTGATTT
TTCTTTCTTTCTTTGTAAATAGTTCTGAGTTCTGTCAAATGCCGTGAAAGTATTTGCTATAA
TAAAGAAAATTCTTGTGACTTTAAAAAAAA
```

FIGURE 12

></usr/seqdb2/sst/DNA/Dnaseqs.min/ss.DNA76400
><subunit 1 of 1, 487 aa, 1 stop
><MW: 55051, pI: 8.14, NX(S/T): 2

MLRAPGCLLRTSVAPAAALAAALLSSLARCSLLEPRDPVASSLSPYFGTKTRYEDVNPVLLS
GPEAPWRDPELLEGTCTPVQLVALIRHGTRYPTVKQIRKLRQLHGLLQARGSRDGGASSTGS
RDLGAALADWPLWYADWMDGQLVEKGRQDMRQLALRLASLFPALFSRENYGRLRLITSSKHR
CMDSSAAFLQGLWQHYHPGLPPPDVADMEFGPPTVNDKLMRFFDHCEKFLTEVEKNATALYH
VEAFKTGPEMQNILKKVAATLQVPVNDLNADLIQVAFFTCSFDLAIKGVKSPWCDVFDIDDA
KVLEYLNDLKQYWKRGYGYTINSRSSCTLFQDIFQHLDKAVEQKQRSQPISSPVILQFGHAE
TLLPLLSLMGYFKDKEPLTAYNYKKQMHRKFRSGLIVPYASNLIFVLYHCENAKTPKEQFRV
QMLLNEKVLPLAYSQETVSFYEDLKNHYKDILQSCQTSEECELARANSTSDEL

Important features:
Signal sequence
amino acids 1-30

N-glycosylation sites.
amino acids 242-246, 481-485

N-myristoylation sites.
amino acids 107-113, 113-119, 117-123, 118-124, 128-134

Endoplasmic reticulum targeting sequence.
amino acids 484-489

FIGURE 13

```
GGGACTACAAGCCGCGCCGCGCTGCCGCTGGCCCCTCAGCAACCCTCGACATGGCGCTGAGGCGGCCACCGCGAC
TCCGGCTCTGCGCTCGGCTGCCTGACTTCTTCCTGCTGCTGCTTTTCAGGGGCTGCCTGATAGGGCTGTAAATC
TCAAATCCAGCAATCGAACCCCAGTGGTACAGGAATTTGAAAGTGTGGAACTGTCTTGCATCATTACGGATTCGC
AGACAAGTGACCCCAGGATCGAGTGGAAGAAAATTCAAGATGAACAAACCACATATGTGTTTTTGACAACAAAA
TTCAGGGAGACTTGGCGGGTCGTGCAGAAATACTGGGGAAGACATCCCTGAAGATCTGGAATGTGACACGGAGAG
ACTCAGCCCTTTATCGCTGTGAGGTCGTTGCTCGAAATGACCGCAAGGAAATTGATGAGATTGTGATCGAGTTAA
CTGTGCAAGTGAAGCCAGTGACCCCTGTCTGTAGAGTGCCGAAGGCTGTACCAGTAGGCAAGATGGCAACACTGC
ACTGCCAGGAGAGTGAGGGCCACCCCGGCCTCACTACAGCTGGTATCGCAATGATGTACCACTGCCCACGGATT
CCAGAGCCAATCCCAGATTTCGCAATTCTTCTTTCCACTTAAACTCTGAAACAGGCACTTTGGTGTTCACTGCTG
TTCACAAGGACGACTCTGGGCAGTACTACTGCATTGCTTCCAATGACGCAGGCTCAGCCAGGTGTGAGGAGCAGG
AGATGGAAGTCTATGACCTGAACATTGGCGGAATTATTGGGGGGGTTCTGGTTGTCCTTGCTGTACTGGCCCTGA
TCACGTTGGGCATCTGCTGTGCATACAGACGTGGCTACTTCATCAACAATAAACAGGATGGAGAAAGTTACAAGA
ACCCAGGGAAACCAGATGGAGTTAACTACATCCGCACTGACGAGGAGGGCGACTTCAGACACAAGTCATCGTTTG
TGATCTGAGACCCGCGGTGTGGCTGAGAGCGCACAGAGCGCACGTGCACATACCTCTGCTAGAAACTCCTGTCAA
GGCAGCGAGAGCTGATGCACTCGGACAGAGCTAGACACTCATTCAGAAGCTTTTCGTTTTGGCCAAAGTTGACCA
CTACTCTTCTTACTCTAACAAGCCACATGAATAGAAGAATTTTCCTCAAGATGGACCCGGTAAATATAACCACAA
GGAAGCGAAACTGGGTGCGTTCACTGAGTTGGGTTCCTAATCTGTTTCTGGCCTGATTCCCGCATGAGTATTAGG
GTGATCTTAAAGAGTTTGCTCACGTAAACGCCCGTGCTGGGCCCTGTGAAGCCAGCATGTTCACCACTGGTCGTT
CAGCAGCCACGACAGCACCATGTGAGATGGCGAGGTGGCTGGACAGCACCAGCAGCGCATCCCGGCGGGAACCCA
GAAAAGGCTTCTTACACAGCAGCCTTACTTCATCGGCCCACAGACACCACCGCAGTTTCTTCTTAAAGGCTCTGC
TGATCGGTGTTGCAGTGTCCATTGTGGAGAAGCTTTTTGGATCAGCATTTGTAAAAACAACCAAAATCAGGAAG
GTAAATTGGTTGCTGGAAGAGGGATCTTGCCTGAGGAACCCTGCTTGTCCAACAGGGTGTCAGGATTTAAGGAAA
ACCTTCGTCTTAGGCTAAGTCTGAAATGGTACTGAAATATGCTTTTCTATGGGTCTTGTTTATTTTATAAAATTT
TACATCTAAATTTTTGCTAAGGATGTATTTTGATTATTGAAAGAAAATTTCTATTTAAACTGTAAATATATTGT
CATACAATGTTAAATAACCTATTTTTTAAAAAAGTTCAACTTAAGGTAGAAGTTCCAAGCTACTAGTGTTAAAT
TGGAAAATATCAATAATTAAGAGTATTTTACCCAAGGAATCCTCTCATGGAAGTTTACTGTGATGTTCCTTTTCT
CACACAAGTTTTAGCCTTTTTCACAAGGGAACTCATACTGTCTACACATCAGACCATAGTTGCTTAGGAAACCTT
TAAAAATTCCAGTTAAGCAATGTTGAAATCAGTTTGCATCTCTTCAAAAGAAACCTCTCAGGTTAGCTTTGAACT
GCCTCTTCCTGAGATGACTAGGACAGTCTGTACCCAGAGGCCACCCAGAAGCCCTCAGATGTACATACACAGATG
CCAGTCAGCTCCTGGGGTTGCGCCAGGCGCCCCCGCTCTAGCTCACTGTTGCCTCGCTGTCTGCCAGGAGGCCCT
GCCATCCTTGGGCCCTGGCAGTGGCTGTGTCCCAGTGAGCTTTACTCACGTGGCCCTTGCTTCATCCAGCACAGC
TCTCAGGTGGGCACTGCAGGGACACTGGTGTCTCCATGTAGCGCTCCCAGCTTTGGGCTCCTGTAACAGACCTCT
TTTTGGTTATGGATGGCTCACAAAATAGGGCCCCCAATGCTATTTTTTTTTTTAAGTTTGTTTAATTATTTGTT
AAGATTGTCTAAGGCCAAAGGCAATTGCGAAATCAAGTCTGTCAAGTACAATAACATTTTTAAAAGAAAATGGAT
CCCACTGTTCCTCTTTGCCACAGAGAAAGCACCCAGACGCCACAGGCTCTGTCGCATTTCAAAACAAACCATGAT
GGAGTGGCGGCCAGTCCAGCCTTTTAAAGAACGTCAGGTGGAGCAGCCAGGTGAAAGGCCTGGCGGGGAGGAAAG
TGAAACGCCTGAATCAAAAGCAGTTTTCTAATTTTGACTTTAAATTTTTCATCCGCCGGAGACACTGCTCCCATT
TGTGGGGGACATTAGCAACATCACTCAGAAGCCTGTGTTCTTCAAGAGCAGGTGTTCTCAGCCTCACATGCCCT
GCCGTGCTGGACTCAGGACTGAAGTGCTGTAAAGCAAGGAGCTGCTGAGAAGGAGCACTCCACTGTGTGCCTGGA
GAATGGCTCTCACTACTCACCTTGTCTTTCAGCTTCCAGTGTCTTGGGTTTTTTATACTTTGACAGCTTTTTTTT
AATTGCATACATGAGACTGTGTTGACTTTTTTTAGTTATGTGAAACACTTTGCCGCAGGCCGCCTGGCAGAGGCA
GGAAATGCTCCAGCAGTGGCTCAGTGCTCCCTGGTGTCTGCTGCATGGCATCCTGGATGCTTAGCATGCAAGTTC
CCTCCATCATTGCCACCTTGGTAGAGAGGGATGGCTCCCCACCCTCAGCGTTGGGGATTCACGCTCCAGCCTCCT
TCTTGGTTGTCATAGTGATAGGGTAGCCTTATTGCCCCCTCTTCTTATACCCTAAAACCTTCTACACTAGTGCCA
TGGGAACCAGGTCTGAAAAGTAGAGAGAAGTGAAAGTAGAGTCTGGGAAGTAGCTGCCTATAACTGAGACTAGA
CGGAAAAGGAATACTCGTGTATTTAAGATATGAATGTGACTCAAGACTCGAGGCCGATACGAGGCTGTGATTCT
GCCTTTGGATGGATGTTGCTGTACACAGATGCTACAGACTTGTACTAACACACCGTAATTTGGCATTTGTTTAAC
CTCATTTATAAAAGCTTCAAAAAAACCCA
```

FIGURE 14

></usr/seqdb2/sst/DNA/Dnaseqs.min/ss.DNA77624
><subunit 1 of 1, 310 aa, 1 stop
><MW: 35020, pI: 7.90, NX(S/T): 3
MALRRPPRLRLCARLPDFFLLLLFRGCLIGAVNLKSSNRTPVVQEFESVELSCIITDSQTSD
PRIEWKKIQDEQTTYVFFDNKIQGDLAGRAEILGKTSLKIWNVTRRDSALYRCEVVARNDRK
EIDEIVIELTVQVKPVTPVCRVPKAVPVGKMATLHCQESEGHPRPHYSWYRNDVPLPTDSRA
NPRFRNSSFHLNSETGTLVFTAVHKDDSGQYYCIASNDAGSARCEEQEMEVYDLNIGGIIGG
VLVVLAVLALITLGICCAYRRGYFINNKQDGESYKNPGKPDGVNYIRTDEEGDFRHKSSFVI Important features of the protein:
Signal peptide:
amino acids 1-30

Transmembrane domain:
amino acids 243-263

N-glycosylation sites.
amino acids 104-107, 192-195 cAMP- and cGMP-dependent protein kinase phosphorylation site.
amino acids 107-110

Casein kinase II phosphorylation site.
amino acids 106-109, 296-299

Tyrosine kinase phosphorylation site.
amino acids 69-77

N-myristoylation sites.
amino acids 26-31, 215-220, 226-231, 243-248, 244-249, 262-267

FIGURE 15

```
CAGGACCAGGTCTTCCTACGCTGGAGCAGCGGGGAGACAGCCACCATGCACATCCTCGTGGTCCATGCCATGGTG
ATCCTGCTGACGCTGGGCCCGCCTCGAGCCGACGACAGCGAGTTCCAGGCGCTGCTGGACATCTGGTTTCCGGAG
GAGAAGCCACTGCCCACCGCCTTCCTGGTGGACACATCGGAGGAGGCGCTGCTGCTTCCTGACTGGCTGAAGCTG
CGCATGATCCGTTCTGAGGTGCTCCGCCTGGTGGACGCCGCCCTGCAGGACCTGGAGCCGCAGCAGCTGCTGCTG
TTCGTGCAGTCGTTTGGCATCCCCGTGTCCAGCATGAGCAAACTCCTCCAGTTCCTGGACCAGGCAGTGGCCCAC
GACCCCAGACTCTGGAGCAGAACATCATGGACAAGAATTACATGGCCCACCTGGTGGAGGTCAGCATGAGCGC
GGCGCCTCCGGAGGCCAGACTTTCCACTCCTTGCTCACAGCCTCCCTGCCGCCCCGCCGAGACAGCACAGAGGCA
CCCAAACCAAAGAGCAGCCCAGAGCAGCCCATAGGCCAGGGCCGGATTCGGGTGGGGACCCAGCTCCGGGTGCTG
GGCCCTGAGGACGACCTGGCTGGCATGTTCCTCCAGATTTTCCCGCTCAGCCCGGACCCTCGGTGGCAGAGCTCC
AGTCCCCGCCCCGTGGCCCTCGCCCTGCAGCAGGCCCTGGGCCAGGAGCTGGCCCGCGTCGTCCAGGGCAGCCCC
GAGGTGCCGGGCATCACGGTGCGTGTCCTGCAGGCCCTCGCCACCCTGCTCAGCTCCCCACACGGCGGTGCCCTG
GTGATGTCCATGCACCGTAGCCACTTCCTGGCCTGCCCGCTGCTGCGCCAGCTCTGCCAGTACCAGCGCTGTGTG
CCACAGGACACCGGCTTCTCCTCGCTCTTCCTGAAGGTGCTCCTGCAGATGCTGCAGTGGCTGGACAGCCCTGGC
GTGGAGGGCGGGCCCCTGCGGGCACAGCTCAGGATGCTTGCCAGCCAGGCCTCAGCCGGGCGCAGGCTCAGTGAT
GTGCGAGGGGGGCTCCTGCGCCTGGCCGAGGCCCTGGCCTTCCGTCAGGACCTGGAGGTGGTCAGCTCCACCGTC
CGTGCCGTCATCGCCACCCTGAGGTCTGGGGAGCAGTGCAGCGTGGAGCCGGACCTGATCAGCAAAGTCCTCCAG
GGGCTGATCGAGGTGAGGTCCCCCCACCTGGAGGAGCTGCTGACTGCATTCTTCTCTGCCACTGCGGATGCTGCC
TCCCGTTTCCAGCCTGTAAGCCCGTTGTGGTGGTGAGCTCCCTGCTGCTGCAGGAGGAGGAGCCCCTGGCTGGG
GGGAAGCCGGGTGCGGACGGTGGCAGCCTGGAGGCCGTGCGGCTGGGGCCCTCGTCAGGCCTCCTAGTGGACTGG
CTGGAAATGCTGGACCCCGAGGTGGTCAGCAGCTGCCCCGACCTGCAGCTCAGGCTGCTCTTCTCCCGGAGGAAG
GGCAAAGGTCAGGCCCAGGTGCCCTCGTTCCGTCCCTACCTCCTGACCCTCTTCACGCATCAGTCCAGCTGGCCC
ACACTGCACCAGTGCATCCGAGTCCTGCTGGGCAAGAGCCGGGAACAGAGGTTCGACCCCTCTGCCTCTCTGGAC
TTCCTCTGGGCCTGCATCCATGTTCCTCGCATCTGGCAGGGCGGGACCAGCGCACCCCGCAGAAGCGGCGGGAG
GAGCTGGTGCTGCGGGTCCAGGGCCCGGAGCTCATCAGCCTGGTGGAGCTGATCCTGGCCGAGGCGGAGACGCGG
AGCCAGGACGGGGACACAGCCGCCTGCAGCCTCATCCAGGCCCGGCTGCCCCTGCTGCTCAGCTGCTGCTGTGGG
GACGATGAGAGTGTCAGGAAGGTGACGGAGCACCTGTCAGGCTGCATCCAGCAGTGGGGAGACAGCGTGCTGGGA
AGGCGCTGCCGAGACCTTCTCCTGCAGCTCTACCTACAGCGGCCGGAGCTGCGGGTGCCCGTGCCTGAGGTCCTA
CTGCACAGCGAAGGGGCTGCCAGCAGCAGCGTCTGCAAGCTGGACGGACTCATCCACCGCTTCATCACGCTCCTT
GCGGACACCAGCGACTCCCGGGCGTTGGAGAACCGAGGGGCCGGATGCCAGCATGGCCTGCCGGAAGCTGGCGGTG
GCGCACCCGCTGCTGCTGCTCAGGCACCTGCCCATGATCGCGGCGCTCCTGCACGGCCGCACCCACCCTCAACTTC
CAGGAGTTCCGGCAGCAGAACCACCTGAGCTGCTTCCTGCACGTGCTGGGCCTGCTGGAGCTGCTGCAGCCGCAC
GTGTTCCGCAGCGAGCACCAGGGGCGCTGTGGGACTGCCTTCTGTCCTTCATCCGCCTGCTGCTGAATTACAGG
AAGTCCTCCCGCCATCTGGCTGCCTTCATCAACAAGTTTGTGCAGTTCATCCATAAGTACATTACCTACAATGCC
CCAGCAGCCATCTCCTTCCTGCAGAAGCACGCCGACCCGCTCCACGACCTGTCCTTCGACAACAGTGACCTGGTG
ATGCTGAAATCCCTCCTTGCAGGGCTCAGCCTGCCCAGCAGGGACGACAGGACCGACCGAGGCCTGGACGAAGAG
GGCGAGGAGGAGAGCTCAGCCGGCTCCTTGCCCCTGGTCAGCGTCTCCCTGTTCACCCCTCTGACCGCGGCCGAG
ATGGCCCCCTACATGAAACGGCTTTCCCGGGGCCAAACGGTGGAGGATCTGCTGGAGGTTCTGAGTGACATAGAC
GAGATGTCCCGGCGGAGACCCGAGATCCTGAGCTTCTTCTCGACCAACCTGCAGCGGCTGATGAGCTCGGCCGAG
GAGTGTTGCCGCAACCTCGCCTTCAGCCTGGCCCTGCGCTCCATGCAGAACAGCCCCAGCATTGCAGCCGCTTTC
CTGCCCACGTTCATGTACTGCCTGGGCAGCCAGGACTTTGAGGTGGTGCAGACGGCCCTCCGGAACCTGCCTGAG
TACGCTCTCCTGTGCCAAGAGCACGCGGCTGTGCTGCTCCACCGGGCCTTCCTGGTGGGCATGTACGGCCAGATG
GACCCCAGCGCGCAGATCTCCGAGGCCCTGAGGATCCTGCATATGGAGGCCGTGATGTGAGCCTGTGGCAGCCGA
CCCCCCTCCAAGCCCCGGCCCGTCCCGTCCCGGGATCCTCGAGGCAAAGCCCAGGAAGCGTGGGCGTTGCTGG
TCTGTCCGAGGAGGTGAGGGCGCCGAGCCCTGAGGCCAGGCAGGCCCAGGAGCAATACTCCGAGCCCTGGGGTGG
CTCCGGGCCGGCCGCTGGCATCAGGGGCCGTCCAGCAAGCCCTCATTCACCTTCTGGGCCACAGCCCTGCCGCGG
AGCGGCGGATCCCCCCGGGCATGGCCTGGGCTGGTTTTGAATGAAACGACCTGAACTGTCAA
```

FIGURE 16

```
></usr/seqdb2/sst/DNA/Dnaseqs.min/ss.DNA77631
><subunit 1 of 1, 1029 aa, 1 stop
><MW: 114213, pI: 6.42, NX(S/T): 0
MHILVVHAMVILLTLGPPRADDSEFQALLDIWFPEEKPLPTAFLVDTSEEALLLPDWLKLRM
IRSEVLRLVDAALQDLEPQQLLLFVQSFGIPVSSMSKLLQFLDQAVAHDPQTLEQNIMDKNY
MAHLVEVQHERGASGGQTFHSLLTASLPPRRDSTEAPKPKSSPEQPIGQGRIRVGTQLRVLG
PEDDLAGMFLQIFPLSPDPRWQSSSPRPVALALQQALGQELARVVQGSPEVPGITVRVLQAL
ATLLSSPHGGALVMSMHRSHFLACPLLRQLCQYQRCVPQDTGFSSLFLKVLLQMLQWLDSPG
VEGGPLRAQLRMLASQASAGRRLSDVRGGLLRLAEALAFRQDLEVVSSTVRAVIATLRSGEQ
CSVEPDLISKVLQGLIEVRSPHLEELLTAFFSATADAASPFPACKPVVVVSSLLLQEEEPLA
GGKPGADGGSLEAVRLGPSSGLLVDWLEMLDPEVVSSCPDLQLRLLFSRRKGKGQAQVPSFR
PYLLTLFTHQSSWPTLHQCIRVLLGKSREQRFDPSASLDFLWACIHVPRIWQGRDQRTPQKR
REELVLRVQGPELISLVELILAEAETRSQDGDTAACSLIQARLPLLLSCCCGDDESVRKVTE
HLSGCIQQWGDSVLGRRCRDLLLQLYLQRPELRVPVPEVLLHSEGAASSSVCKLDGLIHRFI
TLLADTSDSRALENRGADASMACRKLAVAHPLLLLRHLPMIAALLHGRTHLNFQEFRQQNHL
SCFLHVLGLLELLQPHVFRSEHQGALWDCLLSFIRLLLNYRKSSRHLAAFINKFVQFIHKYI
TYNAPAAISFLQKHADPLHDLSFDNSDLVMLKSLLAGLSLPSRDDRTDRGLDEEGEEESSAG
SLPLVSVSLFTPLTAAEMAPYMKRLSRGQTVEDLLEVLSDIDEMSRRRPEILSFFSTNLQRL
MSSAEECCRNLAFSLALRSMQNSPSIAAAFLPTFMYCLGSQDFEVVQTALRNLPEYALLCQE
HAAVLLHRAFLVGMYGQMDPSAQISEALRILHMEAVM Important features:
Signal peptide:
amino acids 1-16 cAMP- and cGMP-dependent protein kinase phosphorylation sites.
amino acids 154-158, 331-335, 616-620, 785-789, 891-895

N-myristoylation sites.
amino acids 91-97, 136-142, 224-230, 435-441, 439-445, 443-449,
665-671, 698-704

Amidation sites.
amino acids 329-333, 634-638
```

FIGURE 17

CCGGGCCATGCAGCCTCGGCCCCGCGGGCGCCCGCCGCGCACCCGAGGAGATGAGGCTCCGC
AATGGCACCTTCCTGACGCTGCTGCTCTTCTGCCTGTGCGCCTTCCTCTCGCTGTCCTGGTA
CGCGGCACTCAGCGGCCAGAAAGGCGACGTTGTGGACGTTTACCAGCGGGAGTTCCTGGCGC
TGCGCGATCGGTTGCACGCAGCTGAGCAGGAGAGCCTCAAGCGCTCCAAGGAGCTCAACCTG
GTGCTGGACGAGATCAAGAGGGCCGTGTCAGAAAGGCAGGCGCTGCGAGACGGAGACGGCAA
TCGCACCTGGGGCCGCCTAACAGAGGACCCCCGATTGAAGCCGTGGAACGGCTCACACCGGC
ACGTGCTGCACCTGCCCACCGTCTTCCATCACCTGCCACACCTGCTGGCCAAGGAGAGCAGT
CTGCAGCCCGCGGTGCGCGTGGGCCAGGGCCGCACCGGAGTGTCGGTGGTGATGGGCATCCC
GAGCGTGCGGCGCGAGGTGCACTCGTACCTGACTGACACTCTGCACTCGCTCATCTCCGAGC
TGAGCCCGCAGGAGAAGGAGGACTCGGTCATCGTGGTGCTGATCGCCGAGACTGACTCACAG
TACACTTCGGCAGTGACAGAGAACATCAAGGCCTTGTTCCCCACGGAGATCCATTCTGGGCT
CCTGGAGGTCATCTCACCCTCCCCCCACTTCTACCCTGACTTCTCCCGCCTCCGAGAGTCCT
TTGGGGACCCCAAGGAGAGAGTCAGGTGGAGGACCAAACAGAACCTCGATTACTGCTTCCTC
ATGATGTACGCGCAGTCCAAAGGCATCTACTACGTGCAGCTGGAGGATGACATCGTGGCCAA
GCCCAACTACCTGAGCACCATGAAGAACTTTGCACTGCAGCAGCCTTCAGAGGACTGGATGA
TCCTGGAGTTCTCCCAGCTGGGCTTCATTGGTAAGATGTTCAAGTCGCTGGACCTGAGCCTG
ATTGTAGAGTTCATTCTCATGTTCTACCGGGACAAGCCCATCGACTGGCTCCTGGACCATAT
TCTGTGGGTGAAAGTCTGCAACCCCGAGAAGGATGCGAAGCACTGTGACCGGCAGAAAGCCA
ACCTGCGGATCCGCTTCAAACCGTCCCTCTTCCAGCACGTGGGCACTCACTCCTCGCTGGCT
GGCAAGATCCAGAAACTGAAGGACAAAGACTTTGGAAAGCAGGCGCTGCGGAAGGAGCATGT
GAACCCGCCAGCAGAGGTGAGCACGAGCCTGAAGACATACCAGCACTTCACCCTGGAGAAAG
CCTACCTGCGCGAGGACTTCTTCTGGGCCTTCACCCCTGCCGCGGGGACTTCATCCGCTTC
CGCTTCTTCCAACCTCTAAGACTGGAGCGGTTCTTCTTCCGCAGTGGGAACATCGAGCACCC
GGAGGACAAGCTCTTCAACACGTCTGTGGAGGTGCTGCCCTTCGACAACCCTCAGTCAGACA
AGGAGGCCCTGCAGGAGGGCCGCACCGCCACCCTCCGGTACCCTCGGAGCCCCGACGGCTAC
CTCCAGATCGGCTCCTTCTACAAGGGAGTGGCAGAGGGAGAGGTGGACCCAGCCTTCGGCCC
TCTGGAAGCACTGCGCCTCTCGATCCAGACGGACTCCCCTGTGTGGGTGATTCTGAGCGAGA
TCTTCCTGAAAAAGGCCGACTAAGCTGCGGGCTTCTGAGGGTACCCTGTGGCCAGCCCTGAA
GCCCACATTTCTGGGGGTGTCGTCACTGCCGTCCCCGGAGGGCCAGATACGGCCCCGCCCAA
AGGGTTCTGCCTGGCGTCGGGCTTGGGCCGGCCTGGGGTCCGCCGCTGGCCCGGAGGCCCTA
GGAGCTGGTGCTGCCCCCGCCCGCCGGGCCGCGGAGGAGGCAGGCGGCCCCCACACTGTGCC
TGAGGCCCGGAACCGTTCGCACCCGGCCTGCCCCAGTCAGGCCGTTTTAGAAGAGCTTTTAC
TTGGGCGCCCGCCGTCTCTGGCGCGAACACTGGAATGCATATACTACTTTATGTGCTGTGTT
TTTTATTCTTGGATACATTTGATTTTTTCACGTAAGTCCACATATACTTCTATAAGAGCGTG
ACTTGTAATAAAGGGTTAATGAAGAAAAAAAAAAAAAAAAAAAAAAAAAAAAAAAAAAAAAA
AAAAAAAAAAAAAAAA

FIGURE 18

```
></usr/seqdb2/sst/DNA/Dnaseqs.min/ss.DNA82307
><subunit 1 of 1, 548 aa, 1 stop
><MW: 63198, pI: 8.10, NX(S/T): 4
MRLRNGTFLTLLLFCLCAFLSLSWYAALSGQKGDVVDVYQREFLALRDRLHAAEQESLKRSK
ELNLVLDEIKRAVSERQALRDGDGNRTWGRLTEDPRLKPWNGSHRHVLHLPTVFHHLPHLLA
KESSLQPAVRVGQGRTGVSVVMGIPSVRREVHSYLTDTLHSLISELSPQEKEDSVIVVLIAE
TDSQYTSAVTENIKALFPTEIHSGLLEVISPSPHFYPDFSRLRESFGDPKERVRWRTKQNLD
YCFLMMYAQSKGIYYVQLEDDIVAKPNYLSTMKNFALQQPSEDWMILEFSQLGFIGKMFKSL
DLSLIVEFILMFYRDKPIDWLLDHILWVKVCNPEKDAKHCDRQKANLRIRFKPSLFQHVGTH
SSLAGKIQKLKDKDFGKQALRKEHVNPPAEVSTSLKTYQHFTLEKAYLREDFFWAFTPAAGD
FIRFRFFQPLRLERFFFRSGNIEHPEDKLFNTSVEVLPFDNPQSDKEALQEGRTATLRYPRS
PDGYLQIGSFYKGVAEGEVDPAFGPLEALRLSIQTDSPVWVILSEIFLKKAD Important features:
Signal sequence
amino acids 1-23

N-glycosylation sites.
amino acids 5-9, 87-91, 103-107, 465-469

N-myristoylation sites.
amino acids 6-12, 136-142, 370-376, 509-515
```

SECRETED AND TRANSMEMBRANE POLYPEPTIDES AND NUCLEIC ACIDS ENCODING THE SAME

RELATED APPLICATIONS

This application is a continuation of, and claims priority under 35 USC §120 to, U.S. application Ser. No. 09/866,034 filed May 25, 2001, which is a continuation of, and claims priority under 35 USC §120 to, PCT Application PCT/US99/28634 filed Dec. 1, 1999, which claims priority under 35 USC §119 to U.S. Provisional Application No. 60/119,965 filed Feb. 12, 1999.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiationfactors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

1. PRO1800

Hep27 protein is synthesized and accumulated in the nucleus of human hepatoblastoma cells (HepG2 cells) following growth arrest induced by butyrate treatment (Gabrielli et al., *Eur. J. Biochem.* 232:473–477 (1995)). The synthesis of Hep27 is inhibited in cells that, released from the butyrate block, have resumed DNA synthesis. The Hep27 protein sequence shows significant homology to the known short-chain alcohol dehydrogenase (SCAD) family of proteins and it has been suggested that Hep27 is a new member of the SCAD family of proteins. In agreement with its nuclear localization, Hep27 has a region similar to the bipartite nuclear-targeting sequence and Hep27 mRNA expression and protein synthesis suggests the existence of a regulation at the post-transcriptional level.

We herein describe the identification and characterization of novel polypeptides having homology to Hep27 protein, designated herein as PRO1800 polypeptides.

2. PRO539

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in Drosophila as well as in vertebrates. Perrimon, *Cell* 80:517–520 (1995).

Costal-2 is a novel kinesin-related protein in the Hedgehog signaling pathway. Hedgehog (Hh) was first identified as a segment-polarity gene by a genetic screen in *Drosophila melanogaster*, Nusslein-Volhard et al. *Roux. Arch. Dev. Biol.* 193: 267–282 (1984), that plays a wide variety of developmental functions. Perrimon, supra. Although only one Drosophila Hh gene has been identified, three mammalian Hh homologues have been isolated: Sonic Hh (SHh), Desert Hh (DHh) and Indian Hh (IHh), Echelard et al., *Cell* 75: 1417–30 (1993); Riddle et al., *Cell* 75: 1401–16 (1993). SHh is expressed at high level in the notochord and floor plate of developing vertebrate embryos. In vitro explant assays as well as ectopic expression of SHh in transgenic animals show that SHh plays a key role in neuronal tube patterning, Echelard et al., supra., Krauss et al., *Cell* 75, 1432–44 (1993), Riddle et al., *Cell* 75: 1401–16 (1993), Roelink et al, *Cell* 81: 445–55 (1995). In vitro explant assays as well as ectopic expression of SHh in transgenic animals show that SHh plays a key role in neural tube patterning, Echelard et al. (1993), supra.; Ericson et al., *Cell* 81: 747–56 (1995);

Marti et al., *Nature* 375: 322–5 (1995); Roelink et al. (1995), supra; Hynes et al., *Neuron* 19: 15–26 (1997). Hh also plays a role in the development of limbs (Krauss et al., *Cell* 75: 1431–44 (1993); Laufer et al., *Cell* 79, 993–1003 (1994)), somites (Fan and Tessier-Lavigne, *Cell* 79, 1175–86 (1994); Johnson et al., *Cell* 79: 1165–73 (1994)), lungs (Bellusci et al., *Develop.* 124: 53–63 (1997) and skin (Oro et al., *Science* 276: 817–21 (1997). Likewise, IHh and DHh are involved in bone, gut and germinal cell development, Apelqvist et al., *Curr. Biol.* 7: 801–4 (1997); Bellusci et al., *Dev. Suppl.* 124: 53–63 (1997); Bitgood et al., *Curr. Biol.* 6: 298–304 (1996); Roberts et al., *Development* 121: 3163–74 (1995). SHh knockout mice further strengthened the notion that SHh is critical to many aspect of vertebrate development, Chiang et al., *Nature* 383: 407–13 (1996). These mice show defects in midline structures such as the notochord and the floor plate, absence of ventral cell types in neural tube, absence of distal limb structures, cyclopia, and absence of the spinal column and most of the ribs.

At the cell surface, the Hh signals is thought to be relayed by the 12 transmembrane domain protein Patched (Ptch) [Hooper and Scott, *Cell* 59: 751–65 (1989); Nakano et al., *Nature* 341: 508–13 (1989)] and the G-protein coupled like receptor Smoothened (Smo) [Alcedo et al., *Cell* 86: 221–232 (1996); van den Heuvel and Ingham, *Nature* 382: 547–551 (1996)]. Both genetic and biochemical evidence support a receptor model where Ptch and Smo are part of a multicomponent receptor complex, Chen and Struhl, *Cell* 87: 553–63 (1996); Marigo et al., *Nature* 384: 176–9 (1996); Stone et al., *Nature* 384: 129–34 (1996). Upon binding of Hh to Ptch, the normal inhibitory effect of Ptch on Smo is relieved, allowing Smo to transduce the Hh signal across the plasma membrane. Loss of function mutations in the Ptch gene have been identified in patients with the basal cell nevus syndrome (BCNS), a hereditary disease characterized by multiple basal cell carcinomas (BCCs). Disfunctional Ptch gene mutations have also been associated with a large percentage of sporadic basal cell carcinoma tumors, Chidambaram et al., *Cancer Research* 56: 4599–601 (1996); Gailani et al., *Nature Genet.* 14: 78–81 (1996); Hahn et al., *Cell* 85: 841–51 (1996); Johnson et al., *Science* 272: 1668–71 (1996); Unden et al., *Cancer Res.* 56: 4562–5; Wicking et al., *Am. J. Hum. Genet.* 60: 21–6 (1997). Loss of Ptch function is thought to cause an uncontrolled Smo signaling in basal cell carcinoma. Similarly, activating Smo mutations have been identified in sporatic BCC tumors (Xie et al., *Nature* 391: 90–2 (1998)), emphasizing the role of Smo as the signaling subunit in the receptor complex for SHh. However, the exact mechanism by which Ptch controls Smo activity still has yet to be clarified and the signaling mechanisms by which the Hh signal is transmitted from the receptor to downstream targets also remain to be elucidated. Genetic epistatic analysis in Drosophila has identified several segment-polarity genes which appear to function as components of the Hh signal transduction pathway, Ingham, *Curr. Opin. Genet. Dev.* 5: 492–8 (1995); Perrimon, supra. These include a kinesin-like molecule, Costal-2 (Cos-2) [Robbins et al., *Cell* 90: 225–34 (1997); Sisson et al., *Cell* 90: 235–45 (1997)], a protein designated fused [Preat et al., *Genetics* 135: 1047–62 (1990); Therond et al., *Proc. Natl. Acad Sci. USA* 93: 4224–8 (1996)], a novel molecule with unknown function designated Suppressor of fused [Pham et al., *Genetics* 140: 587–98 (1995); Preat, *Genetics* 132: 725–36 (1992)] and a zinc finger protein Ci. [Alexandre et al., *Genes Dev.* 10: 2003–13 (1996); Dominguez et al., *Science* 272: 1621–5 (1996); Orenic et al, *Genes Dev.* 4: 1053–67 (1990)]. Additional elements implicated in Hh signaling include the transcription factor CBP [Akimaru et al., *Nature* 386: 735–738 (1997)], the negative regulator slimb [Jiang and Struhl, *Nature* 391: 493–496 (1998)] and the SHh response element COUP-TFII [Krishnan et al., *Science* 278: 1947–1950 (1997)].

Mutants in Cos-2 are embryonicly lethal and display a phenotype similar to Hh over expression, including duplications of the central component of each segment and expansion domain of Hh responsive genes. In contrast, mutant embryos for fused and Ci show a phenotype similar to Hh loss of function including deletion of the posterior part of each segment and replacement of a mirror-like image duplication of the anterior part or each segment and replacement of a mirror-like duplication of the anterior part, Busson et al., *Roux. Arch. Dev. Biol.* 197: 221–230 (1988). Molecular characterizations of Ci suggested that it is a transcription factor which directly activates Hh responsive genes such as Wingless and Dpp, Alexandre et al., (1996) supra, Dominguez et al., (1996) supra. Likewise, molecular analysis of fused reveals that it is structurally related to serine threonine kinases and that both intact N-terminal kinase domain and a C-terminal regulatory region are required for its proper function, Preat et al., *Nature* 347: 87–9 (1990); Robbins et al., (1997), supra; Therond et al., *Proc. Natl. Acad. Sci. USA* 93: 4224–8 (1996). Consistent with the putative opposing functions of Cos-2 and fused, fused mutations are suppressed by Cos-2 mutants and also by Suppressor of fused mutants, Preat et al., *Genetics* 135: 1047–62 (1993). However, whereas fused null mutations and N-terminal kinase domain mutations can be fully suppressed by Suppressor of fused mutations, C-terminus mutations of fused display a strong Cos-2 phenotype in a Suppressor of fused background. This suggests that the fused kinase domain can act as a constitutive activator of SHh signaling when Suppressor of Fused is not present. Recent studies have shown that the 92 kDa Drosophila fused, Cos-2 and Ci are present in a microtubule associated multiprotein complex and that Hh signaling leads to dissociation of this complex from microtubules, Robbins et al, *Cell* 90: 225–34 (1997); Sisson et al., *Cell* 90: 235–45 (1997). Both fused and Cos-2 become phosphorylated in response to Hh treatment, Robbins et al., supra; Therond et al., *Genetics* 142: 1181–98 (1996), but the kinase(s) responsible for this activity(ies) remain to be characterized. To date, the only known vertebrate homologues for these components are members of the Gli protein family (e.g., Gli-1, Gli-2 and Gli-3). These are zinc finger putative transcription factors that are structurally related to Ci. Among these, Gli-1 was shown to be a candidate mediator of the SHh signal [Hynes et al., *Neuron* 15: 35–44 (1995), Lee et al., *Development* 124: 2537–52 (1997); Alexandre et al., *Genes Dev.* 10: 2003–13 (1996)] suggesting that the mechanism of gene activation in response to Hh may be conserved between fly and vertebrates. To determine whether other signaling components in the Hh cascade are evolutionarily conserved and to examine the function of fused in the Hh signaling cascade on the biochemical level, Applicants have isolated and characterized the human fused cDNA. Tissue distribution on the mouse indicates that fused is expressed in SHh responsive tissues. Biochemical studies demonstrate that fused is a functional kinase. Functional studies provide evidence that fused is an activator of Gli and that a dominant negative form of fused is capable of blocking SHh signaling in Xenopus embryos. Together this data demonstrated that both Cos-2 and fused are directly involved in Hh signaling.

For additional references related to the Costal-2 protein, see Simpson et al., *Dev. Biol.* 122:201–209 (1987), Grau et al., *Dev. Biol.* 122:186–200 (1987), Preat et al., *Genetics* 135:1047–1062 (1993), Sisson et al., *Cell* 90:235–245 (1997) and Robbins et al., *Cell* 90:225–234 (1997).

Applicants have herein identified and describe a cDNA encoding a human Costal-2 homolog polypeptide, designated herein as PRO539.

3. PRO982

Efforts are being undertaken by both industry and academia to identify new, native secreted proteins. Many efforts are focused on the screening of mammalian recombinant DNA libraries to identify the coding sequences for novel secreted proteins. We herein describe the identification and characterization of novel secreted polypeptides, designated herein as PRO982 polypeptides.

4. PRO1434

The nel gene has been described to encode a protein that is expressed in the neural tissues of chicken (Watanabe et al., *Genomics* 38(3):273–276 (1996)). Recently, two novel human cDNAs (designated NELL1 and NELL2) have been isolated and characterized which encode polypeptides having homology to that encoded by the chicken nel gene, wherein those human polypeptides contain six EGF-like repeats (Watanabe et al., supra). Given the neural-specific expression of these genes, it is suggested that they may play a role in neural development. There is, therefore, significant interest in identifying and characterizing novel polypeptides having homology to net, NELL1 and NELL2.

We herein describe the identification and characterization of novel polypeptides having homology to the net protein, designated herein as PRO1434 polypeptides.

5. PRO1863

Efforts are being undertaken by both industry and academia to identify new, native transmembrane proteins. Many efforts are focused on the screening of mammalian recombinant DNA libraries to identify the coding sequences for novel transmembrane proteins. We herein describe the identification and characterization of novel transmembrane polypeptides, designated herein as PRO1863 polypeptides.

6. PRO1917

The characterization of inositol phosphatases is of interest because it is fundamental to the understanding of signaling activities that stimulate the release of $Ca^{2+}$ from the endoplasmic reticulum. Molecular cloning allowed the identification of a multiple inositol polyphosphate phosphatase which is highly expressed in kidney and liver (Craxton et al. (1997) *Biochem J.* 328:75–81).

7. PRO1868

The inflammatory response is complex and is mediated by a variety of signaling molecules produced locally by mast cells, nerve endings, platelets, leucocytes and complement activation. Certain of these signaling molecules cause the endothelial cell lining to become more porous and/or even to express selectins which act as cell surface molecules which recognize and attract leucocytes through specific carbohydrate recognition. Stronger leucocyte binding is mediated by integrins, which mediate leukocyte movement through the endothelium. Additional signaling molecules act as chemoattractants, causing the bound leucocytes to crawl towards the source of the attractant. Other signaling molecules produced in the course of an inflammatory response escape into the blood and stimulate the bone marrow to produce more leucocytes and release them into the blood stream.

Inflammation is typically initiated by an antigen, which can be virtually any molecule capable of initiating an immune response. Under normal physiological conditions these are foreign molecules, but molecules generated by the organism itself can serve as the catalyst as is known to occur in various disease states.

T-cell proliferation is a mixed lymphocyte culture or mixed lymphocyte reaction (MLR) is an established indication of the ability of a compound to stimulate the immune system. In an inflammatory response, the responding leucocytes can be neutrophilic, eosinophilic, monocytic or lymphocytic. Histological examination of the affected tissues provides evidence of an immune stimulating or inhibiting response. See *Current Protocols in Immunology*, ed. John E. Coligan, 1994, John Wiley and Sons, Inc.

Inflammatory bowel disease (IBD) is a term used to collectively describe gut disorders including both ulcerative colitis (UC) and Crohn's disease, both of which are classified as distinct disorders, but share common features and likely share pathology. The commonality of the diagnostic criteria can make it difficult to precisely determine which of the two disorders a patient has; however the type and location of the lesion in each are typically different. UC lesions are characteristically a superficial ulcer of the mucosa and appear in the colon, proximal to the rectum. CD lesions are characteristically extensive linear fissures, and can appear anywhere in the bowel, occasionally involving the stomach, esophagus and duodenum.

Conventional treatments for IBD usually involve the administration of antiinflammatory or immunosuppressive agents, such as sulfasalazine, corticosteriods, 6-mercaptopurine/azathoprine, or cyclospoine all of which only bring partial relief to the afflicted patient. However, when antiinflammatory/immunosuppressive therapies fail, colectomies are the last line of defense. Surgery is required for about 30% of CD patients within the first year after diagnosis, with the likelihood for operative procedure increasing about 5% annually thereafter. Unfortunately, CD also has a high rate of reoccurrence as about 5% of patients require subsequent surgery after the initial year. UC patients further have a substantially increased risk of developing colorectal cancer. Presumably, this is due to the recurrent cycles of injury to the epithelium, followed by regrowth, which continually increases the risk of neoplastic transformation.

A recently discovered member of the immunoglobulin superfamily known as Junctional Adhesion Molecule (JAM) has been identified to be selectively concentrated at intercellular junctions of endothelial and epithelial cells of different origins. Martin-Padura, I. et al., *J. Cell Biol.* 142(1): 117–27 (1998). JAM is a type I integral membrane protein with two extracellular, intrachain disulfide loops of the V-type. JAM bears substantial homology to A33 antigen (FIG. 1 or FIG. 18). A monoclonal antibody directed to JAM was found to inhibit spontaneous and chemokine-induced monocyte transmigration through an endothelial cell monolayer in vitro. Martin-Padura, supra.

It has been recently discovered that JAM expression is increased in the colon of CRF2-4–/– mice with colitis. CRF 2-4–/– (IL-10R subunit knockout mice) develop a spontaneous colitis mediated by lymphocytes, monocytes and neutrophils. Several of the animals also developed colon adenocarcinoma. As a result, it is foreseeable likely that the compounds of the invention are expressed in elevated levels in or otherwise associated with human diseases such as inflammatory bowel disease, other inflammatory diseases of the gut as well as colorectal carcinoma.

The compounds of the invention also bear significant homology to A33 antigen, a known colorectal cancer-associated marker. The A33 antigen is expressed in more than 90% of primary or metastatic colon cancers as well as normal colon epithelium. In carcinomas originating from the colonic mucosa, the A33 antigen is expressed homogeneously in more than 95% of all cases. The A33 antigen, however, has not been detected in a wide range of other normal issues, i.e., its expression appears to be organ specific. Therefore, the A33 antigen appears to play an important role in the induction of colorectal cancer.

Since colon cancer is a widespread disease, early diagnosis and treatment is an important medical goal. Diagnosis and treatment of colon cancer can be implemented using monoclonal antibodies (mAbs) specific therefore having fluorescent, nuclear magnetic or radioactive tags. Radioactive gene, toxins and/or drug tagged mAbs can be used for treatment in situ with minimal patient description. mAbs can also be used to diagnose during the diagnosis and treatment of colon cancers. For example, when the serum levels of the A33 antigen are elevated in a patient, a drop of the levels after surgery would indicate the tumor resection was successful. On the other hand, a subsequent rise in serum A33 antigen levels after surgery would indicate that metastases of the original tumor may have formed or that new primary tumors may have appeared.

Such monoclonal antibodies can be used in lieu of, or in conjunction with surgery and/or other chemotherapies. For example, preclinical analysis and localization studies in patients infected with colorectal carcinoma with a mAb to A33 are described in Welt et al., *J. Clin. Oncol.* 8: 1894–1906 (1990) and Welt et al., *J. Clin. Oncol.* 12: 1561–1571 (1994), while U.S. Pat. No. 4,579,827 and U.S. Ser. No. 424,991 (E.P. 199,141) are directed to the therapeutic administration of monoclonal antibodies, the latter of which relates to the application of anti-A33 mAb.

We herein describe the identification and characterization of novel polypeptides having homology to A33 antigen protein, designated herein as PRO1868 polypeptides.

8. PRO3434

Efforts are being undertaken by both industry and academia to identify new, native secreted proteins. Many efforts are focused on the screening of mammalian recombinant DNA libraries to identify the coding sequences for novel secreted proteins. We herein describe the identification and characterization of novel secreted polypeptides, designated herein as PRO3434 polypeptides.

9. PRO1927

Proteins are glycosylated by a complex set of reactions which are mediated by membrane bound glycosyltransferases. There is a large number of different glycosyltransferases that account for the array of carbohydrate structures synthesized. N-acetylglucosaminyltransferase proteins comprise a family of glycosyltransferases that provide for a variety of important biological functions in the mammalian organism. As an example, UDP-N-acetylglucosamine: alpha-3-D-mannoside beta-1,2-N-acetylglucosaminyltransferase I is an glycosyltransferase that catalyzes an essential first step in the conversion of high-mannose N-glycans to hybrid and complex N-glycans (Sarkar et al., *Proc. Natl. Acad. Sci. USA.* 88:234–238 (1991). UPD-N-acetylglucosamine: alpha 1,3-D-mannoside beta 1,4-N-acetylglucosaminyltransferase is an essential enzyme in the production of tri- and tetra-antennary asparagine-linked sugar chains, and has been recently been purified from bovine small intestine using cDNA cloning (Minowa et al., *J. Biol. Chem.* (1998) 273(19): 11556–62). There is interest in the identification and characterization of additional members of the N-acetylglucosaminyltransferase protein family, and more generally, the identification of novel glycosyltransferases.

SUMMARY OF THE INVENTION

1. PRO1800

A cDNA clone (DNA35672-2508) has been identified, having homology to nucleic acid encoding Hep27 protein, that encodes a novel polypeptide, designated in the present application as "PRO1800".

In one embodiment, the invention provides an isolated nucleic acid molecule comprising DNA encoding a PRO1800 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1800 polypeptide having the sequence of amino acid residues from about 1 or about 16 to about 278, inclusive of FIG. 2 (SEQ ID NO:2), or (b) the complement of the DNA molecule of (a).

In another aspect, the invention concerns an isolated nucleic acid molecule encoding a PRO1800 polypeptide comprising DNA hybridizing to the complement of the nucleic acid between about nucleotides 36 or about 81 and about 869, inclusive, of FIG. 1 (SEQ ID NO:1). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203538 (DNA35672-2508) or (b) the complement of the nucleic acid molecule of (a). In a preferred embodiment, the nucleic acid comprises a DNA encoding the same mature polypeptide encoded by the human protein cDNA in ATCC Deposit No. 203538 (DNA35672-2508).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 16 to about 278, inclusive of FIG. 2 (SEQ ID NO:2), or (b) the complement of the DNA of (a).

In a further aspect, the invention concerns an isolated nucleic acid molecule having at least 230 nucleotides and produced by hybridizing a test DNA molecule under stringent conditions with (a) a DNA molecule encoding a PRO1800 polypeptide having the sequence of amino acid residues from 1 or about 16 to about 278, inclusive of FIG. 2 (SEQ ID NO:2), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1800 polypeptide, with or without the N-terminal signal sequence and/or the initiating methionine, or is complementary to such encoding nucleic acid molecule. The signal peptide has been tentatively identified as extending from about amino acid position 1 to about amino acid position 15 in the sequence of FIG. 2 (SEQ ID NO:2).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 16 to about 278, inclusive of FIG. 2 (SEQ ID NO:2), or (b) the complement of the DNA of (a).

Another embodiment is directed to fragments of a PRO1800 polypeptide coding sequence that may find use as hybridization probes. Such nucleic acid fragments may be from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 1 (SEQ ID NO:1).

In another embodiment, the invention provides isolated PRO1800 polypeptide encoded by any of the isolated nucleic acid sequences hereinabove identified.

In a specific aspect, the invention provides isolated native sequence PRO1800 polypeptide, which in certain embodiments, includes an amino acid sequence comprising residues 1 or about 16 to about 278 of FIG. 2 (SEQ ID NO:2).

In another aspect, the invention concerns an isolated PRO1800 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 16 to about 278, inclusive of FIG. 2 (SEQ ID NO:2).

In a further aspect, the invention concerns an isolated PRO1800 polypeptide, comprising an amino acid sequence scoring at least about 80% positives, preferably at least about 85% positives, more preferably at least about 90% positives, most preferably at least about 95% positives when compared with the amino acid sequence of residues 1 or about 16 to about 278, inclusive of FIG. 2 (SEQ ID NO:2).

In yet another aspect, the invention concerns an isolated PRO1800 polypeptide, comprising the sequence of amino acid residues 1 or about 16 to about 278, inclusive of FIG. 2 (SEQ ID NO:2), or a fragment thereof sufficient to provide a binding site for an anti-PRO1800 antibody. Preferably, the PRO1800 fragment retains a qualitative biological activity of a native PRO1800 polypeptide.

In a still further aspect, the invention provides a polypeptide produced by (i) hybridizing a test DNA molecule under stringent conditions with (a) a DNA molecule encoding a PRO1800 polypeptide having the sequence of amino acid residues from about 1 or about 16 to about 278, inclusive of FIG. 2 (SEQ ID NO: 2), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1800 polypeptide. In a particular embodiment, the agonist or antagonist is an anti-PRO1800 antibody.

In a further embodiment, the invention concerns a method of identifying agonists or antagonists of a native PRO1800 polypeptide by contacting the native PRO1800 polypeptide with a candidate molecule and monitoring a biological activity mediated by said polypeptide.

In a still further embodiment, the invention concerns a composition comprising a PRO1800 polypeptide, or an agonist or antagonist as hereinabove defined, in combination with a pharmaceutically acceptable carrier.

2. PRO539

A cDNA clone (DNA47465-1561) has been identified, having homology to nucleic acid encoding Costal-2 protein, that encodes a novel polypeptide, designated in the present application as "PRO539".

In one embodiment, the invention provides an isolated nucleic acid molecule comprising DNA encoding a PRO539 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO539 polypeptide having the sequence of amino acid residues from about 1 to about 830, inclusive of FIG. 4 (SEQ ID NO:7), or (b) the complement of the DNA molecule of (a).

In another aspect, the invention concerns an isolated nucleic acid molecule encoding a PRO539 polypeptide comprising DNA hybridizing to the complement of the nucleic acid between about nucleotides 186 and about 2675, inclusive, of FIG. 3 (SEQ ID NO:6). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203661 (DNA47465-1561) or (b) the complement of the nucleic acid molecule of (a). In a preferred embodiment, the nucleic acid comprises a DNA encoding the same mature polypeptide encoded by the human protein cDNA in ATCC Deposit No. 203661 (DNA47465-1561).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 to about 830, inclusive of FIG. 4 (SEQ ID NO:7), or (b) the complement of the DNA of (a).

In a further aspect, the invention concerns an isolated nucleic acid molecule having at least 100 nucleotides and produced by hybridizing a test DNA molecule under stringent conditions with (a) a DNA molecule encoding a PRO539 polypeptide having the sequence of amino acid residues from 1 to about 830, inclusive of FIG. 4 (SEQ ID NO:7), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO539 polypeptide, with or without the initiating methionine, or is complementary to such encoding nucleic acid molecule.

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 to about 830, inclusive of FIG. 4 (SEQ ID NO:7), or (b) the complement of the DNA of (a).

Another embodiment is directed to fragments of a PRO539 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 3 (SEQ ID NO:6).

In another embodiment, the invention provides isolated PRO539 polypeptide encoded by any of the isolated nucleic acid sequences hereinabove identified.

In a specific aspect, the invention provides isolated native sequence PRO539 polypeptide, which in certain embodiments, includes an amino acid sequence comprising residues 1 to about 830 of FIG. 4 (SEQ ID NO:7).

In another aspect, the invention concerns an isolated PRO539 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 to about 830, inclusive of FIG. 4 (SEQ ID NO:7).

In a further aspect, the invention concerns an isolated PRO539 polypeptide, comprising an amino acid sequence scoring at least about 80% positives, preferably at least about 85% positives, more preferably at least about 90% positives, most preferably at least about 95% positives when compared with the amino acid sequence of residues 1 to about 830, inclusive of FIG. 4 (SEQ ID NO:7).

In yet another aspect, the invention concerns an isolated PRO539 polypeptide, comprising the sequence of amino acid residues 1 to about 830, inclusive of FIG. 4 (SEQ ID NO:7), or a fragment thereof sufficient to provide a binding site for an anti-PRO539 antibody. Preferably, the PRO539 fragment retains a qualitative biological activity of a native PRO539 polypeptide.

In a still further aspect, the invention provides a polypeptide produced by (i) hybridizing a test DNA molecule under stringent conditions with (a) a DNA molecule encoding a PRO539 polypeptide having the sequence of amino acid residues from about 1 to about 830, inclusive of FIG. 4 (SEQ ID NO:7), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO539 polypeptide. In a particular embodiment, the agonist or antagonist is an anti-PRO539 antibody.

In a further embodiment, the invention concerns a method of identifying agonists or antagonists of a native PRO539 polypeptide by contacting the native PRO539 polypeptide with a candidate molecule and monitoring a biological activity mediated by said polypeptide. In a preferred embodiment, the biological activity is either binding to microtubiles or the ability to complex with fused and cubitus interruptus.

In a still further embodiment, the invention concerns a composition comprising a PRO539 polypeptide, or an agonist or antagonist as hereinabove defined, in combination with a pharmaceutically acceptable carrier.

In yet another embodiment, the invention provides for compounds and methods for developing antagonists against and agonist promoting PRO539 modulation of Hedgehog signaling. In particular, an antagonist of vertebrate PRO539 which blocks, prevents, inhibits and/or neutralized the normal functioning of PRO539 in SH signaling pathway, including both small bioorganic molecules and antisense nucleotides.

In yet another embodiment, the invention provides for alternatively spliced variants of human PRO539.

In still yet a further embodiment, the invention provides a method of screening or assaying for identifying molecules that alter the PRO539 modulation of hedgehog signaling. Preferably, the molecules either prevent interaction of PRO539 with its associative complexing proteins (such as fused or cubitus interruptus) or prevent or inhibit dissociation of complexes. The assay comprises the incubation of a mixture comprising PRO539 and a substrate with a candidate molecule and detection of the ability of the candidate molecule to modulate PRO539 hedgehog signaling. The screened molecules preferably are small molecule drug candidates.

In yet another embodiment, the method relates to a technique of diagnosing to determine whether a particular disorder is modulated by hedgehog signaling, comprising:
  (a) culturing test cells or tissues;
  (b) administering a compound which can inhibit PRO539 modulated hedgehog signaling; and
  (c) determining whether hedgehog signaling is modulated.

3. PRO982

A cDNA clone (DNA57700-1408) has been identified that encodes a novel polypeptide, designated in the present application as "PRO982."

In one embodiment, the invention provides an isolated nucleic acid molecule comprising DNA encoding a PRO982 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO982 polypeptide having the sequence of amino acid residues from 1 or about 22 to about 125, inclusive of FIG. 6 (SEQ ID NO:9), or (b) the complement of the DNA molecule of (a).

In another aspect, the invention concerns an isolated nucleic acid molecule encoding a PRO982 polypeptide comprising DNA hybridizing to the complement of the nucleic acid between about residues 89 and about 400, inclusive, of FIG. 5 (SEQ ID NO:8). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203583 (DNA57700-1408), or (b) the complement of the DNA molecule of (a). In a preferred embodiment, the nucleic acid comprises a DNA encoding the same mature polypeptide encoded by the human protein cDNA in ATCC Deposit No. 203583 (DNA57700-1408).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from 1 or about 22 to about 125, inclusive of FIG. 6 (SEQ ID NO:9), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO982 polypeptide having the sequence of amino acid residues from 1 or about 22 to about 125, inclusive of FIG. 6 (SEQ ID NO:9), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO982 polypeptide, with or without the N-terminal signal sequence and/or the initiating methionine, or is complementary to such encoding nucleic acid molecule. The signal peptide has been tentatively identified as extending from amino acid position 1 through about amino acid position 21 in the sequence of FIG. 6 (SEQ ID NO:9)

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 22 to about 125, inclusive of FIG. 6 (SEQ ID NO:9), or (b) the complement of the DNA of (a).

Another embodiment is directed to fragments of a PRO982 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO982 polypeptide encoded by any of the isolated nucleic acid sequences hereinabove defined.

In a specific aspect, the invention provides isolated native sequence PRO982 polypeptide, which in one embodiment, includes an amino acid sequence comprising residues 1 or about 22 to 125 of FIG. 6 (SEQ ID NO:9).

In another aspect, the invention concerns an isolated PRO982 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 22 to about 125, inclusive of FIG. 6 (SEQ ID NO:9).

In a further aspect, the invention concerns an isolated PRO982 polypeptide, comprising an amino acid sequence scoring at least about 80% positives, preferably at least about 85% positives, more preferably at least about 90% positives, most preferably at least about 95% positives when compared with the amino acid sequence of residues 1 or about 22 to 125 of FIG. 6 (SEQ ID NO:9).

In yet another aspect, the invention concerns an isolated PRO982 polypeptide, comprising the sequence of amino acid residues 1 or about 22 to about 125, inclusive of FIG. 6 (SEQ ID NO:9), or a fragment thereof sufficient to provide a binding site for an anti-PRO982 antibody. Preferably, the PRO982 fragment retains a qualitative biological activity of a native PRO982 polypeptide.

In a still further aspect, the invention provides a polypeptide produced by (i) hybridizing a test DNA molecule under stringent conditions with (a) a DNA molecule encoding a PRO982 polypeptide having the sequence of amino acid residues from 1 or about 22 to about 125, inclusive of FIG. 6 (SEQ ID NO:9), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

4. PRO1434

A cDNA clone (DNA68818-2536) has been identified, having homology to nucleic acid encoding nel protein, that encodes a novel polypeptide, designated in the present application as "PRO1434".

In one embodiment, the invention provides an isolated nucleic acid molecule comprising DNA encoding a PRO1434 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1434 polypeptide having the sequence of amino acid residues from about 1 or about 28 to about 325, inclusive of FIG. 8 (SEQ ID NO: 11), or (b) the complement of the DNA molecule of (a).

In another aspect, the invention concerns an isolated nucleic acid molecule encoding a PRO1434 polypeptide comprising DNA hybridizing to the complement of the nucleic acid between about nucleotides 581 or about 662 and about 1555, inclusive, of FIG. 7 (SEQ ID NO:10). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203657 (DNA68818-2536) or (b) the complement of the nucleic acid molecule of (a). In a preferred embodiment, the nucleic acid comprises a DNA encoding the same mature polypeptide encoded by the human protein cDNA in ATCC Deposit No. 203657 (DNA68818-2536).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 28 to about 325, inclusive of FIG. 8 (SEQ ID NO: 11), or (b) the complement of the DNA of (a).

In a further aspect, the invention concerns an isolated nucleic acid molecule having at least 65 nucleotides and produced by hybridizing a test DNA molecule under stringent conditions with (a) a DNA molecule encoding a PRO1434 polypeptide having the sequence of amino acid residues from 1 or about 28 to about 325, inclusive of FIG. 8 (SEQ ID NO:11), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1434 polypeptide, with or without the N-terminal signal sequence and/or the initiating methionine, and its soluble, i.e., transmembrane domain deleted or inactivated variants, or is complementary to such encoding nucleic acid molecule. The signal peptide has been tentatively identified as extending from about amino acid position 1 to about amino acid position 27 in the sequence of FIG. 8 (SEQ ID NO:11). The transmembrane domain has been tentatively identified as extending from about amino acid position 11 to about amino acid position 30 in the PRO1434 amino acid sequence (FIG. 8, SEQ ID NO:11).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 28 to about 325, inclusive of FIG. 8 (SEQ ID NO:11), or (b) the complement of the DNA of (a).

Another embodiment is directed to fragments of a PRO1434 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 7 (SEQ ID NO:10).

In another embodiment, the invention provides isolated PRO1434 polypeptide encoded by any of the isolated nucleic acid sequences hereinabove identified.

In a specific aspect, the invention provides isolated native sequence PRO1434 polypeptide, which in certain embodiments, includes an amino acid sequence comprising residues 1 or about 28 to about 325 of FIG. 8 (SEQ ID NO:11).

In another aspect, the invention concerns an isolated PRO1434 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 28 to about 325, inclusive of FIG. 8 (SEQ ID NO:11).

In a further aspect, the invention concerns an isolated PRO1434 polypeptide, comprising an amino acid sequence scoring at least about 80% positives, preferably at least about 85% positives, more preferably at least about 90% positives, most preferably at least about 95% positives when compared with the amino acid sequence of residues 1 or about 28 to about 325, inclusive of FIG. 8 (SEQ ID NO:11).

In yet another aspect, the invention concerns an isolated PRO1434 polypeptide, comprising the sequence of amino acid residues 1 or about 28 to about 325, inclusive of FIG. 8 (SEQ ID NO:11), or a fragment thereof sufficient to provide a binding site for an anti-PRO1434 antibody. Preferably, the PRO1434 fragment retains a qualitative biological activity of a native PRO1434 polypeptide.

In a still further aspect, the invention provides a polypeptide produced by (i) hybridizing a test DNA molecule under stringent conditions with (a) a DNA molecule encoding a PRO1434 polypeptide having the sequence of amino acid residues from about 1 or about 28 to about 325, inclusive of FIG. 8 (SEQ ID NO:11), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1434 polypeptide. In a particular embodiment, the agonist or antagonist is an anti-PRO1434 antibody.

In a further embodiment, the invention concerns a method of identifying agonists or antagonists of a native PRO1434 polypeptide by contacting the native PRO1434 polypeptide with a candidate molecule and monitoring a biological activity mediated by said polypeptide.

In a still further embodiment, the invention concerns a composition comprising a PRO1434 polypeptide, or an agonist or antagonist as hereinabove defined, in combination with a pharmaceutically acceptable carrier.

5. PRO1863

A cDNA clone (DNA59847-2510) has been identified that encodes a novel transmembrane polypeptide, designated in the present application as "PRO1863".

In one embodiment, the invention provides an isolated nucleic acid molecule comprising DNA encoding a PRO1863 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1863 polypeptide having the sequence of amino acid residues from about 1 or about 16 to about 437, inclusive of FIG. 10 (SEQ ID NO: 16), or (b) the complement of the DNA molecule of (a).

In another aspect, the invention concerns an isolated nucleic acid molecule encoding a PRO1863 polypeptide comprising DNA hybridizing to the complement of the nucleic acid between about nucleotides 17 or about 62 and about 1327, inclusive, of FIG. 9 (SEQ ID NO:15). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203576 (DNA59847-2510) or (b) the complement of the nucleic acid molecule of (a). In a preferred embodiment, the nucleic acid comprises a DNA encoding the same mature polypeptide encoded by the human protein cDNA in ATCC Deposit No. 203576 (DNA59847-2510).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 16 to about 437, inclusive of FIG. 10 (SEQ ID NO:16), or (b) the complement of the DNA of (a).

In a further aspect, the invention concerns an isolated nucleic acid molecule having at least 345 nucleotides and produced by hybridizing a test DNA molecule under stringent conditions with (a) a DNA molecule encoding a PRO1863 polypeptide having the sequence of amino acid residues from 1 or about 16 to about 437, inclusive of FIG. 10 (SEQ ID NO:16), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1863 polypeptide, with or without the N-terminal signal sequence and/or the initiating methionine, and its soluble, i.e., transmembrane domain deleted or inactivated variants, or is complementary to such encoding nucleic acid molecule. The signal peptide has been tentatively identified as extending from about amino acid position 1 to about amino acid position 17 in the sequence of FIG. 10 (SEQ ID NO:16). The transmembrane domain has been tentatively identified as extending from about amino acid position 243 to about amino acid position 260 in the PRO1863 amino acid sequence (FIG. 10, SEQ ID NO:16).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 16 to about 437, inclusive of FIG. 10 (SEQ ID NO:16), or (b) the complement of the DNA of (a).

Another embodiment is directed to fragments of a PRO1863 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 9 (SEQ ID NO:15).

In another embodiment, the invention provides isolated PRO1863 polypeptide encoded by any of the isolated nucleic acid sequences hereinabove identified.

In a specific aspect, the invention provides isolated native sequence PRO1863 polypeptide, which in certain embodiments, includes an amino acid sequence comprising residues 1 or about 16 to about 437 of FIG. 10 (SEQ ID NO:16).

In another aspect, the invention concerns an isolated PRO1863 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 16 to about 437, inclusive of FIG. 10 (SEQ ID NO:16).

In a further aspect, the invention concerns an isolated PRO1863 polypeptide, comprising an amino acid sequence scoring at least about 80% positives, preferably at least about 85% positives, more preferably at least about 90% positives, most preferably at least about 95% positives when compared with the amino acid sequence of residues 1 or about 16 to about 437, inclusive of FIG. 10 (SEQ ID NO:16).

In yet another aspect, the invention concerns an isolated PRO1863 polypeptide, comprising the sequence of amino acid residues 1 or about 16 to about 437, inclusive of FIG. 10 (SEQ ID NO:16), or a fragment thereof sufficient to provide a binding site for an anti-PRO1863 antibody. Preferably, the PRO1863 fragment retains a qualitative biological activity of a native PRO1863 polypeptide.

In a still further aspect, the invention provides a polypeptide produced by (i) hybridizing a test DNA molecule under stringent conditions with (a) a DNA molecule encoding a PRO1863 polypeptide having the sequence of amino acid residues from about 1 or about 16 to about 437, inclusive of FIG. 10 (SEQ ID NO:16), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1863 polypeptide. In a particular embodiment, the agonist or antagonist is an anti-PRO1863 antibody.

In a further embodiment, the invention concerns a method of identifying agonists or antagonists of a native PRO1863 polypeptide by contacting the native PRO1863 polypeptide with a candidate molecule and monitoring a biological activity mediated by said polypeptide.

In a still further embodiment, the invention concerns a composition comprising a PRO1863 polypeptide, or an agonist or antagonist as hereinabove defined, in combination with a pharmaceutically acceptable carrier.

6. PRO1917

A cDNA clone (DNA76400-2528) has been identified that encodes a novel polypeptide having homology to inositol phosphatase and designated in the present application as "PRO1917".

In one embodiment, the invention provides an isolated nucleic acid molecule comprising DNA encoding a PRO1917 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1917 polypeptide having the sequence of amino acid residues from 1 or about 31 to about 487, inclusive of FIG. 12 (SEQ ID NO:18), or (b) the complement of the DNA molecule of (a).

In another aspect, the invention concerns an isolated nucleic acid molecule encoding a PRO1917 polypeptide comprising DNA hybridizing to the complement of the nucleic acid between about residues 96 and about 1466, inclusive, of FIG. 11 (SEQ ID NO:17). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203573 (DNA76400-2528), or (b) the complement of the DNA molecule of (a). In a preferred embodiment, the nucleic acid comprises a DNA encoding the same mature polypeptide encoded by the human protein cDNA in ATCC Deposit No. 203573 (DNA76400-2528).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from 1 or about 31 to about 487, inclusive of FIG. 12 (SEQ ID NO:18), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO1917 polypeptide having the sequence of amino acid residues from 1 or about 31 to about 487, inclusive of FIG. 12 (SEQ ID NO:18), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1917 polypeptide, with or without the N-terminal signal sequence and/or the initiating methionine, or is complementary to such encoding nucleic acid molecule. The signal peptide has been tentatively identified as extending from amino acid position 1 through about amino acid position 30 in the sequence of FIG. 12 (SEQ ID NO:18).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 31 to about 487, inclusive of FIG. 12 (SEQ ID NO:18), or (b) the complement of the DNA of (a).

Another embodiment is directed to fragments of a PRO1917 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO1917 polypeptide encoded by any of the isolated nucleic acid sequences hereinabove defined.

In a specific aspect, the invention provides isolated native sequence PRO1917 polypeptide, which in one embodiment, includes an amino acid sequence comprising residues 1 or about 31 to 487 of FIG. 12 (SEQ ID NO:18).

In another aspect, the invention concerns an isolated PRO1917 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 31 to about 487, inclusive of FIG. 12 (SEQ ID NO:18).

In a further aspect, the invention concerns an isolated PRO1917 polypeptide, comprising an amino acid sequence scoring at least about 80% positives, preferably at least about 85% positives, more preferably at least about 90% positives, most preferably at least about 95% positives when compared with the amino acid sequence of residues 1 or about 31 to 487 of FIG. 12 (SEQ ID NO:18).

In yet another aspect, the invention concerns an isolated PRO1917 polypeptide, comprising the sequence of amino acid residues 1 or about 31 to about 487, inclusive of FIG. 12 (SEQ ID NO:18), or a fragment thereof sufficient to provide a binding site for an anti-PRO1917 antibody. Preferably, the PRO1917 fragment retains a qualitative biological activity of a native PRO1917 polypeptide.

In a still further aspect, the invention provides a polypeptide produced by (i) hybridizing a test DNA molecule under stringent conditions with (a) a DNA molecule encoding a PRO1917 polypeptide having the sequence of amino acid residues from 1 or about 31 to about 487, inclusive of FIG. 12 (SEQ ID NO:18), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1917 polypeptide. In a particular embodiment, the agonist or antagonist is an anti-PRO1917 antibody.

In a further embodiment, the invention concerns a method of identifying agonists or antagonists of a native PRO1917 polypeptide, by contacting the native PRO1917 polypeptide with a candidate molecule and monitoring a biological activity mediated by said polypeptide.

In a still further embodiment, the invention concerns a composition comprising a PRO1917 polypeptide, or an agonist or antagonist as hereinabove defined, in combination with a pharmaceutically acceptable carrier.

7. PRO1868

The present invention concerns compositions and methods for the diagnosis and treatment of inflammatory diseases in mammals, including humans. The present invention is based on the identification of proteins (including agonist and antagonist antibodies) which either stimulate or inhibit the immune response in mammals. Inflammatory diseases can be treated by suppressing the inflammatory response. Molecules that enhance an inflammatory response stimulate or potentiate the immune response to an antigen. Molecules which stimulate an inflammatory response can be inhibited where suppression of the inflammatory response would be beneficial. Molecules which stimulate the inflammatory response can be used therapeutically where enhancement of the inflammatory response would be beneficial. Such stimulatory molecules can also be inhibited where suppression of the inflammatory response would be of value. Neutralizing antibodies are examples of molecules that inhibit molecules having immune stimulatory activity and which would be beneficial in the treatment of inflammatory diseases. Molecules which inhibit the inflammatory response can also be utilized (proteins directly or via the use of antibody agonists) to inhibit the inflammatory response and thus ameliorate inflammatory diseases.

Accordingly, the proteins of the invention are useful for the diagnosis and/or treatment (including prevention) of immune related diseases. Antibodies which bind to stimulatory proteins are useful to suppress the inflammatory response. Antibodies which bind to inhibitory proteins are useful to stimulate inflammatory response and the immune system. The proteins and antibodies of the invention are also useful to prepare medicines and medicaments for the treatment of inflammatory and immune related diseases.

In one embodiment, the invention concerns antagonists and agonists of a PRO1868 polypeptide that inhibits one or more of the functions or activities of a PRO1868 polypeptide.

In another embodiment, the invention concerns a method for determining the presence of a PRO1868 polypeptide comprising exposing a cell suspected of containing the polypeptide to an anti-PRO1868 antibody and determining binding of the antibody to the cell.

In yet another embodiment, the present invention relates to a method of diagnosing an inflammatory elated disease in a mammal, comprising detecting the level of expression of a gene encoding a PRO1868 polypeptide (a) in a test sample of tissue cells obtained from the mammal, and (b) in a control sample of known normal tissue cells of the same cell type, wherein a higher expression level in the test sample indicates the presence of an inflammatory disease in the mammal.

In another embodiment, the present invention relates to method of diagnosing an inflammatory disease in a mammal, comprising (a) contacting an anti-PRO1868 antibody with a test sample of tissue culture cells obtained from the mammal, and (b) detecting the formation of a complex between the antibody and the PRO1868 polypeptide. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality relating to the inflammatory response.

In another embodiment, the present invention relates to a diagnostic kit, containing an anti-PRO1868 antibody and a carrier (e.g., a buffer) in suitable packaging. The kit preferably contains instructions for using the antibody to detect the PRO1868 polypeptide.

In a further embodiment, the invention concerns an article of manufacture, comprising:
 a container;
 a label on the container; and
 a composition comprising an active agent contained within the container; wherein the composition is effective for stimulating or inhibiting an inflammatory response in a mammal, the label on the container indicates that the composition can be used to treat an inflammatory disease, and the active agent in the composition is an agent stimulating or inhibiting the expression and/or activity of the PRO1868 polypeptide. In a preferred aspect, the active agent is a PRO1868 polypeptide or an anti-PRO1868 antibody.

A further embodiment is a method for identifying a compound capable of inhibiting the expression and/or activity of a PRO1868 polypeptide by contacting a candidate compound with a PRO1868 polypeptide under conditions and for time sufficient to allow these two compounds to interact. In a specific aspect, either the candidate compound or the PRO1868 polypeptide is immobilized on a solid support. In another aspect, the non-immobilized component carries a detectable label.

In yet a further aspect, the invention relates to a method of treating an inflammatory disease, by administration of an effective therapeutic amount of a PRO1868 antagonist to a patient in need thereof for the treatment of a disease selected from: inflammatory bowel disease, systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis, eosinophilic pneumonias, idiopathic pulmonary fibrosis and hypersensitivity pneumonitis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonias, idiopathic pulmonary fibrosis and hypersensitivity pneumonitis, transplantation associated diseases including graft rejection and graft-verus host disease.

In a further embodiment, the present invention provides a method of diagnosing tumor in a mammal, comprising detecting the level of expression of a gene encoding a PRO1868 polypeptide (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained.

In another embodiment, the present invention provides a method of diagnosing tumor in a mammal, comprising (a) contacting an anti-PRO1868 antibody with a test sample of the tissue cells obtained from the mammal, and (b) detecting the formation of a complex between the anti-PRO1868 and the PRO1868 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art. Preferably, the test sample is obtained from an individual mammal suspected to have neoplastic cell growth or proliferation (e.g., cancerous cells).

In another embodiment, the present invention provides a cancer diagnostic kit, comprising an anti-PRO1868 antibody and a carrier (e.g. a buffer) in suitable packaging. The kit preferably contains instructions for using the antibody to detect the PRO1868 polypeptide.

In yet another embodiment, the invention provides a method for inhibiting the growth of tumor cells comprising exposing a cell which overexpresses a PRO1868 polypeptide to an effective amount of an agent inhibiting the expression and/or activity of the PRO1868 polypeptide. The agent preferably is an anti-PRO1868 polypeptide, a small organic and inorganic peptide, phosphopeptide, antisense or ribozyme molecule, or a triple helix molecule. In a specific aspect, the agent, e.g., anti-PRO1868 antibody induces cell death. In a further aspect, the tumor cells are further exposed to radiation treatment and/or a cytotoxic or chemotherapeutic agent.

In a further embodiment, the invention concerns an article of manufacture, comprising:
a container;
a label on the container, and
a composition comprising an active agent contained within the container; wherein the composition is effective for inhibiting the growth of tumor cells, the label on the container indicates that the composition can be used for treating conditions characterized by overexpression of a PRO1868 polypeptide, and the active agent in the composition is an agent inhibiting the expression and/or activity of the PRO1868 polypeptide. In a preferred aspect, the active agent is an anti-PRO1868 antibody.

A cDNA clone (DNA77624-2515) has been identified, having homology to nucleic acid encoding A33 antigen, that encodes a novel polypeptide, designated in the present application as "PRO1868".

In one embodiment, the invention provides an isolated nucleic acid molecule comprising DNA encoding a PRO1868 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1868 polypeptide having the sequence of amino acid residues from about 1 or about 31 to about 310, inclusive of FIG. 14 (SEQ ID NO:20), or (b) the complement of the DNA molecule of (a).

In another aspect, the invention concerns an isolated nucleic acid molecule encoding a PRO1868 polypeptide comprising DNA hybridizing to the complement of the nucleic acid between about nucleotides 51 or about 141 and about 980, inclusive, of FIG. 13 (SEQ ID NO:19). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203553 (DNA77624-2515) or (b) the complement of the nucleic acid molecule of (a). In a preferred embodiment, the nucleic acid comprises a DNA encoding the same mature polypeptide encoded by the human protein cDNA in ATCC Deposit No. 203553 (DNA77624-2515).

In still a further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues 1 or about 31 to about 310 inclusive of FIG. 14 (SEQ ID NO:20), or (b) the complement of the DNA of (a).

In a further aspect, the invention concerns an isolated nucleic acid molecule having at least 390 nucleotides and produced by hybridizing a test DNA molecule under stringent conditions with (a) a DNA molecule encoding a PRO1868 polypeptide having the sequence of amino acid residues from 1 or about 31 to about 310, inclusive of FIG. 14 (SEQ ID NO:20), or (b) the complement of the DNA molecule of (a), and, if the DNA molecule has at least about an 80% sequence identity, prefereably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1868 polypeptide, with or without the N-terminal signal sequence and/or the initiating methionine, and its soluble, i.e., transmembrane domain deleted or inactivated variants, or is complementary to such encoding nucleic acid molecule. The signal peptide has been tentatively identified as extending from about amino acid position 1 to about amino acid position 30 in the sequence of FIG. 14 (SEQ ID NO:20). The transmembrane domain has been tentatively identified as extending from about amino acid position 243 to about amino acid position 263 in the PRO1868 amino acid sequence (FIG. 14, SEQ ID NO:20).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 31 to about 310 inclusive of FIG. 14 (SEQ ID NO:20), or (b) the complement of the DNA of (a).

Another embodiment is directed to fragments of a PRO1868 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length and most preferably from about 20 to about 40 nucleotides in length and may be derived from the nucleotide sequence shown in FIG. 13 (SEQ ID NO:19).

In another embodiment, the invention provides isolated PRO1868 polypeptide encoded by any of the isolated nucleic acid sequences hereinabove identified.

In a specific aspect, the invention provides isolated native sequence PRO1868 polypeptide, which in certain embodiments, includes an amino acid sequence comprising residues 1 or about 31 to about 310 of FIG. 14 (SEQ ID NO:20).

In another aspect, the invention concerns an isolated PRO1868 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 31 to about 310, inclusive of FIG. 14 (SEQ ID NO:20).

In a further aspect, the invention concerns an isolated PRO1868 polypeptide, comprising an amino acid sequence scoring at least about 80% positives, preferably at least about 85% positives, more preferably at least about 90% positives, most preferably at least about 95% positives when compared with the amino acid sequence of residues 1 or about 31 to about 310, inclusive of FIG. 14 (SEQ ID NO:20).

In yet another aspect, the invention concerns an isolated PRO1868 polypeptide, comprising the sequence of amino acid residues 1 or about 31 to about 310, inclusive of FIG. 14 (SEQ ID NO:20), or a fragment thereof sufficient to provide a binding site for an anti-PRO1868 antibody. Preferably, the PRO1868 fragment retains a qualitative biological activity of a native PRO1868 polypeptide.

In a still further aspect, the invention provides a polypeptide produced by (i) hybridizing a test DNA molecule under stringent conditions with (a) a DNA molecule encoding a PRO1868 polypeptide having the sequence of amino acid residues from about 1 or about 31 to about 310, inclusive of FIG. 14 (SEQ ID NO:20), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1868 polypeptide. In a particular embodiment, the agonist or antagonist is an anti-PRO1868 antibody.

In a further embodiment, the invention concerns a method of identifying agonists or antagonists of a native PRO1868 polypeptide by contacting the native PRO1868 polypeptide with a candidate molecule and monitoring a biological activity mediated by said polypeptide.

In a still further embodiment, the invention concerns a composition comprising a PRO1868 polypeptide, or an agonist or antagonist as hereinabove defined, in combination with a pharmaceutically acceptable carrier.

In another embodiment, the invention provides a composition containing a PRO1868 polypeptide or an agonist or antagonist antibody in admixture with a carrier or excipient. In one aspect, the composition contains a therapeutically affective amount of the peptide or antibody. In another aspect, when the composition contains an inflammation stimulating molecule, the composition is useful for: (a) increasing infiltration of inflammatory cells into a tissue of a mammal in need thereof, (b) stimulating or enhancing an immune response in a mammal in need thereof, or (c) increasing the proliferation of T-lymphocytes in a mammal in need thereof in response to an antigen. In a further aspect, when the composition contains an inflammatory inhibiting molecule, the composition is useful for: (a) decreasing infiltration of inflammatory cells into a tissue of a mammal in need thereof, (b) inhibiting or reducing an inflammatory response in a mammal in need thereof, or (c) decreasing the proliferation of T-lymphocytes in a mammal in need thereof in response to an antigen. In another aspect, the composition contains a further active ingredient, which may, for example, be a further antibody or a cytotoxic or chemotherapeutic agent. Preferably, the composition is sterile.

In a further embodiment, the invention concerns nucleic acid encoding an anti-PRO1868 antibody, and vectors and recombinant host cells comprising such nucleic acid. In a still further embodiment, the invention concerns a method for producing such an antibody by culturing a host cell transformed with nucleic acid encoding the antibody under conditions such that the antibody is expressed, and recovering the antibody from the cell culture.

8. PRO3434

A cDNA clone (DNA77631-2537) has been identified that encodes a novel polypeptide, designated in the present application as "PRO3434."

In one embodiment, the invention provides an isolated nucleic acid molecule comprising DNA encoding a PRO3434 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO3434 polypeptide having the sequence of amino acid residues from 1 or about 17 to about 1029, inclusive of FIG. 16 (SEQ ID NO:22), or (b) the complement of the DNA molecule of (a).

In another aspect, the invention concerns an isolated nucleic acid molecule encoding a PRO3434 polypeptide comprising DNA hybridizing to the complement of the nucleic acid between about residues 46 or about 94 and about 3132, inclusive, of FIG. 15 (SEQ ID NO:21). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203651 (DNA77631-2537), or (b) the complement of the DNA molecule of (a). In a preferred embodiment, the nucleic acid comprises a DNA encoding the same mature polypeptide encoded by the human protein cDNA in ATCC Deposit No. 203651 (DNA77631-2537).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from 1 or about 17 to about 1029, inclusive of FIG. 16 (SEQ ID NO:22), or the complement of the DNA of (a).

In a further aspect, the invention concerns an isolated nucleic acid molecule having at least about 460 nucleotides and produced by hybridizing a test DNA molecule under stringent conditions with (a) a DNA molecule encoding a PRO3434 polypeptide having the sequence of amino acid residues from 1 or about 17 to about 1029, inclusive of FIG. 16 (SEQ ID NO:22), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO3434 polypeptide, with or without the N-terminal signal sequence and/or the initiating methionine, or is complementary to such encoding nucleic acid molecule. The signal peptide has been tentatively identified as extending from amino acid position 1 through about amino acid position 16 in the sequence of FIG. 16 (SEQ ID NO:22).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 17 to about 1029, inclusive of FIG. 16 (SEQ ID NO:22), or (b) the complement of the DNA of (a).

Another embodiment is directed to fragments of a PRO3434 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO3434 polypeptide encoded by any of the isolated nucleic acid sequences hereinabove defined.

In a specific aspect, the invention provides isolated native sequence PRO3434 polypeptide, which in one embodiment, includes an amino acid sequence comprising residues 1 or about 17 to 1029 of FIG. 16 (SEQ ID NO:22).

In another aspect, the invention concerns an isolated PRO3434 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 17 to about 1029, inclusive of FIG. 16 (SEQ ID NO:22).

In a further aspect, the invention concerns an isolated PRO3434 polypeptide, comprising an amino acid sequence scoring at least about 80% positives, preferably at least about 85% positives, more preferably at least about 90% positives, most preferably at least about 95% positives when compared with the amino acid sequence of residues 1 or about 17 to 1029 of FIG. 16 (SEQ ID NO:22).

In yet another aspect, the invention concerns an isolated PRO3434 polypeptide, comprising the sequence of amino acid residues 1 or about 17 to about 1029, inclusive of FIG. 16 (SEQ ID NO:22), or a fragment thereof sufficient to provide a binding site for an anti-PRO3434tibody. Preferably, the PRO982 fragment retains a qualitative biological activity of a native PRO3434 polypeptide.

In a still further aspect, the invention provides a polypeptide produced by (i) hybridizing a test DNA molecule under stringent conditions with (a) a DNA molecule encoding a PRO3434 polypeptide having the sequence of amino acid residues from 1 or about 17 to about 1029, inclusive of FIG. 16 (SEQ ID NO:22), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO3434 polypeptide. In a particular embodiment, the agonist or antagonist is an anti-PRO3434 antibody.

In a further embodiment, the invention concerns a method of identifying agonists or antagonists of a native PRO3434 polypeptide, by contacting the native PRO3434 polypeptide with a candidate molecule and monitoring a biological activity mediated by said polypeptide.

In a still further embodiment, the invention concerns a composition comprising a PRO3434 polypeptide, or an agonist or antagonist as hereinabove defined, in combination with a pharmaceutically acceptable carrier.

9. PRO1927

A cDNA clone (DNA82307-2531)has been identified that encodes a novel polypeptide having homology to glycosyltransferases, and is designated in the present application as "PRO1927".

In one embodiment, the invention provides an isolated nucleic acid molecule comprising DNA encoding a PRO1927 polypeptide.

In one aspect, the isolated nucleic acid comprises DNA having at least about 80% sequence identity, preferably at least about 85% sequence identity, more preferably at least about 90% sequence identity, most preferably at least about 95% sequence identity to (a) a DNA molecule encoding a PRO1927 polypeptide having the sequence of amino acid residues from 1 or about 24 to about 548, inclusive of FIG. 18 (SEQ ID NO:24), or (b) the complement of the DNA molecule of (a).

In another aspect, the invention concerns an isolated nucleic acid molecule encoding a PRO1927 polypeptide comprising DNA hybridizing to the complement of the nucleic acid between about residues 120 and about 1694, inclusive, of FIG. 17 (SEQ ID NO:23). Preferably, hybridization occurs under stringent hybridization and wash conditions.

In a further aspect, the invention concerns an isolated nucleic acid molecule comprising DNA having at least about 80% sequence identity, preferably at least about 85% sequence identity, more preferably at least about 90% sequence identity, most preferably at least about 95% sequence identity to (a) a DNA molecule encoding the same mature polypeptide encoded by the human protein cDNA in ATCC Deposit No. 203537 (DNA82307-2531), or (b) the complement of the DNA molecule of (a). In a preferred embodiment, the nucleic acid comprises a DNA encoding the same mature polypeptide encoded by the human protein cDNA in ATCC Deposit No. 203537 (DNA82307-2531).

In a still further aspect, the invention concerns an isolated nucleic acid molecule comprising (a) DNA encoding a polypeptide having at least about 80% sequence identity, preferably at least about 85% sequence identity, more preferably at least about 90% sequence identity, most preferably at least about 95% sequence identity to the sequence of amino acid residues from 1 or about 24 to about 548, inclusive of FIG. 18 (SEQ ID NO:24), or the complement of the DNA of (a).

In a further aspect, the invention concerns an isolated nucleic acid molecule having at least about 50 nucleotides, and preferably at least about 100 nucleotides and produced by hybridizing a test DNA molecule under stringent conditions with (a) a DNA molecule encoding a PRO1927 polypeptide having the sequence of amino acid residues from 1 or about 24 to about 548, inclusive of FIG. 18 (SEQ ID NO:24), or (b) the complement of the DNA molecule of (a), and, if the DNA molecule has at least about an 80% sequence identity, preferably at least about an 85% sequence identity, more preferably at least about a 90% sequence identity, most preferably at least about a 95% sequence identity to (a) or (b), isolating the test DNA molecule.

In a specific aspect, the invention provides an isolated nucleic acid molecule comprising DNA encoding a PRO1927 polypeptide, with or without the N-terminal signal sequence and/or the initiating methionine, and its soluble variants (i.e. transmembrane domain deleted or inactivated), or is complementary to such encoding nucleic acid molecule. The signal peptide has been tentatively identified as extending from amino acid position 1 through about amino acid position 23 in the sequence of FIG. 18 (SEQ ID NO:24). A type II transmembrane domain has been tentatively identified as extending from about amino acid position 6 to about amino acid position 25 in the PRO1927 amino acid sequence (FIG. 18, SEQ ID NO:24).

In another aspect, the invention concerns an isolated nucleic acid molecule comprising (a) DNA encoding a polypeptide scoring at least about 80% positives, preferably at least about 85% positives, more preferably at least about 90% positives, most preferably at least about 95% positives when compared with the amino acid sequence of residues 1 or about 24 to about 548, inclusive of FIG. 18 (SEQ ID NO:24), or (b) the complement of the DNA of (a).

Another embodiment is directed to fragments of a PRO1927 polypeptide coding sequence that may find use as hybridization probes. Such nucleic acid fragments are from about 20 to about 80 nucleotides in length, preferably from about 20 to about 60 nucleotides in length, more preferably from about 20 to about 50 nucleotides in length, and most preferably from about 20 to about 40 nucleotides in length.

In another embodiment, the invention provides isolated PRO1927 polypeptide encoded by any of the isolated nucleic acid sequences hereinabove defined.

In a specific aspect, the invention provides isolated native sequence PRO1927 polypeptide, which in one embodiment, includes an amino acid sequence comprising residues 1 or about 24 to 548 of FIG. 18 (SEQ ID NO:24).

In another aspect, the invention concerns an isolated PRO1927 polypeptide, comprising an amino acid sequence having at least about 80% sequence identity, preferably at least about 85% sequence identity, more preferably at least about 90% sequence identity, most preferably at least about 95% sequence identity to the sequence of amino acid residues 1 or about 24 to about 548, inclusive of FIG. 18 (SEQ ID NO:24).

In a further aspect, the invention concerns an isolated PRO1927 polypeptide, comprising an amino acid sequence scoring at least about 80% positives, preferably at least about 85% positives, more preferably at least about 90% positives, most preferably at least about 95% positives when compared with the amino acid sequence of residues 1 or about 24 to 548 of FIG. 18 (SEQ ID NO:24).

In yet another aspect, the invention concerns an isolated PRO1927 polypeptide, comprising the sequence of amino acid residues 1 or about 24 to about 548, inclusive of FIG. 18 (SEQ ID NO:24), or a fragment thereof sufficient to provide a binding site for an anti-PRO1927 antibody. Preferably, the PRO1927 fragment retains a qualitative biological activity of a native PRO1927 polypeptide.

In a still further aspect, the invention provides a polypeptide produced by (i) hybridizing a test DNA molecule under stringent conditions with (a) a DNA molecule encoding a PRO1927 polypeptide having the sequence of amino acid residues from 1 or about 24 to about 548, inclusive of FIG. 18 (SEQ ID NO:24), or (b) the complement of the DNA molecule of (a), and if the test DNA molecule has at least about an 80% sequence identity, preferably at least about an 85% sequence identity, more preferably at least about a 90% sequence identity, most preferably at least about a 95% sequence identity to (a) or (b), (ii) culturing a host cell comprising the test DNA molecule under conditions suitable for expression of the polypeptide, and (iii) recovering the polypeptide from the cell culture.

In yet another embodiment, the invention concerns agonists and antagonists of a native PRO1927 polypeptide. In a particular embodiment, the agonist or antagonist is an anti-PRO1927 antibody.

In a further embodiment, the invention concerns a method of identifying agonists or antagonists of a native PRO1927 polypeptide, by contacting the native PRO1927 polypeptide with a candidate molecule and monitoring a biological activity mediated by said polypeptide.

In a still further embodiment, the invention concerns a composition comprising a PRO1927 polypeptide, or an agonist or antagonist as hereinabove defined, in combination with a pharmaceutically acceptable carrier 10. Additional Embodiments In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:1) of a native sequence PRO1800 cDNA, wherein SEQ ID NO:1 is a clone designated herein as "DNA35672-2508".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:6) of a native sequence PRO539 cDNA, wherein SEQ ID NO:6 is a clone designated herein as "DNA47465-1561".

FIG. 4 shows the amino acid sequence (SEQ ID NO:7) derived from the coding sequence of SEQ ID NO:6 shown in FIG. 3.

FIG. 5 shows a nucleotide sequence (SEQ ID NO:8) of a native sequence PRO982 cDNA, wherein SEQ ID NO:8 is a clone designated herein as "DNA57700-1408".

FIG. 6 shows the amino acid sequence (SEQ ID NO:9) derived from the coding sequence of SEQ ID NO: 8 shown in FIG. 5.

FIG. 7 shows a nucleotide sequence (SEQ ID NO:10) of a native sequence PRO1434 cDNA, wherein SEQ ID NO:10 is a clone designated herein as "DNA68818-2536".

FIG. 8 shows the amino acid sequence (SEQ ID NO:11) derived from the coding sequence of SEQ ID NO:10 shown in FIG. 7.

FIG. 9 shows a nucleotide sequence (SEQ ID NO:15) of a native sequence PRO1863 cDNA, wherein SEQ ID NO:15 is a clone designated herein as "DNA59847-2510".

FIG. 10 shows the amino acid sequence (SEQ ID NO:16) derived from the coding sequence of SEQ ID NO:16 shown in FIG. 9.

FIG. 11 shows a nucleotide sequence (SEQ ID NO:17) of a native sequence PRO1917 cDNA, wherein SEQ ID NO:17 is a clone designated herein as "DNA76400-2528".

FIG. 12 shows the amino acid sequence (SEQ ID NO:18) derived from the coding sequence of SEQ ID NO:18 shown in FIG. 11.

FIG. 13 shows a nucleotide sequence (SEQ ID NO:19) of a native sequence PRO1868 cDNA, wherein SEQ ID NO:19 is a clone designated herein as "DNA77624-2515".

FIG. 14 shows the amino acid sequence (SEQ ID NO:20) derived from the coding sequence of SEQ ID NO:19 shown in FIG. 13.

FIG. 15 shows a nucleotide sequence (SEQ ID NO:21) of a native sequence PRO3434 cDNA, wherein SEQ ID NO:21 is a clone designated herein as "DNA77631-2537".

FIG. 16 shows the amino acid sequence (SEQ ID NO:22) derived from the coding sequence of SEQ ID NO:21 shown in FIG. 15.

FIG. 17 shows a nucleotide sequence (SEQ ID NO:23) of a native sequence PRO1927 cDNA, wherein SEQ ID NO:23 is a clone designated herein as "DNA82307-2531".

FIG. 18 shows the amino acid sequence (SEQ ID NO:24) derived from the coding sequence of SEQ ID NO:23 shown in FIG. 17.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10: 1–6 (1997) and von Heinje et al., *Nucl. Acids. Res.* 14:4683–4690 (1986)). Moreover, it is also recognized that, in some cases, cleavage of a signal sequence from a secreted polypeptide is not entirely uniform, resulting in more than one secreted species. These polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 5 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389–3402

(1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix= BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389–3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5× SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1× SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. µIntermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

TABLE 1

```
/*
*
* C-C increased from 12 to 15
* Z is average of EQ
* B is average of ND
* match with stop is _M; stop-stop = 0; J (joker) match = 0
*/
#define _M      -8       /* value of a match with a stop */
int     _day[26][26] = {
/*    A  B  C  D  E  F  G  H  I  J  K  L  M  N  O  P  Q  R  S  T  U  V  W  X  Y  Z */
/* A */ {2, 0, -2, 0, 0, -4, 1, -1, -1, 0, -1, -2, -1, 0, _M, 1, 0, -2, 1, 1, 0, 0, -6, 0, -3, 0},
/* B */ {0, 3, -4, 3, 2, -5, 0, 1, -2, 0, 0, -3, -2, 2, _M, -1, 1, 0, 0, 0, 0, -2, -5, 0, -3, 1},
/* C */ {-2, -4, 15, -5, -5, -4, -3, -3, -2, 0, -5, -6, -5, -4, _M, -3, -5, -4, 0, -2, 0, -2, -8, 0, 0, -5},
/* D */ {0, 3, -5, 4, 3, -6, 1, 1, -2, 0, 0, -4, -3, 2, _M, -1, 2, -1, 0, 0, 0, -2, -7, 0, -4, 2},
/* E */ {0, 2, -5, 3, 4, -5, 0, 1, -2, 0, 0, -3, -2, 1, _M, -1, 2, -1, 0, 0, 0, -2, -7, 0, -4, 3},
/* F */ {-4, -5, -4, -6, -5, 9, -5, -2, 1, 0, -5, 2, 0, -4, _M, -5, -5, -4, -3, -3, 0, -1, 0, 0, 7, -5},
/* G */ {1, 0, -3, 1, 0, -5, 5, -2, -3, 0, -2, -4, -3, 0, _M, -1, -1, -3, 1, 0, 0, -1, -7, 0, -5, 0},
/* H */ {-1, 1, -3, 1, 1, -2, -2, 6, -2, 0, 0, -2, -2, 2, _M, 0, 3, 2, -1, -1, 0, -2, -3, 0, 0, 2},
/* I */ {-1, -2, -2, -2, -2, 1, -3, -2, 5, 0, -2, 2, 2, -2, _M, -2, -2, -2, -1, 0, 0, 4, -5, 0, -1, -2},
/* J */ {0, 0, 0, 0, 0, 0, 0, 0, 0, 0, 0, 0, 0, 0, _M, 0, 0, 0, 0, 0, 0, 0, 0, 0, 0, 0},
/* K */ {-1, 0, -5, 0, 0, -5, -2, 0, -2, 0, 5, -3, 0, 1, _M, -1, 1, 3, 0, 0, 0, -2, -3, 0, -4, 0},
/* L */ {-2, -3, -6, -4, -3, 2, -4, -2, 2, 0, -3, 6, 4, -3, _M, -3, -2, -3, -3 , -1, 0, 2, -2, 0, -1, -2}
/* M */ {-1, -2, -5, -3, -2, 0, -3, -2, 2, 0, 0, 4, 6, -2, _M, -2, -1, 0, -2, -1, 0, 2, -4, 0, -2, -1},
/* N */ {0, 2, -4, 2, 1, -4, 0, 2, -2, 0, 1, -3, -2, 2, _M, -1, 1, 0, 1, 0, 0, -2, -4, 0, -2, 1},
/* O */ {_M,_M,_M,_M,_M,_M,_M,_M,_M,_M,_M,_M,_M,_M,_M,_M,_M,_M,_M,_M,_M,_M,_M,_M,_M,_M,},
/* P */ {1, -1, -3, -1, -1, -5, -1, 0, -2, 0, -1, -3, -2, -1,_M, 6, 0, 0, 1, 0, 0, -1, -6, 0, -5, 0},
/* Q */ {0, 1, -5, 2, 2, -5, -1, 3, -2, 0, 1, -2, -1, 1, _M, 0, 4, 1, -1, -1, 0, -2, -5, 0, -4, 3},
/* R */ {-2, 0, -4, -1, -1, -4, -3, 2, -2, 0, 3, -3, 0, 0, _M, 0, 1, 6, 0, -1, 0, -2, 2, 0, -4, 0},
/* S */ {1, 0, 0, 0, 0, -3, 1, -1, -1, 0, 0, -3, -2, 1, _M, 1, -1, 0, 2, 1, 0, -1, -2, 0, -3, 0},
/* T */ {1, 0, -2, 0, 0, -3, 0, -1, 0, 0, 0, -1, -1, 0, _M, 0, -1, -1, 1, 3, 0, 0, -5, 0, -3, 0},
/* U */ {0, 0, 0, 0, 0, 0, 0, 0, 0, 0, 0, 0, 0, 0,_M, 0, 0, 0, 0, 0, 0, 0, 0, 0, 0},
/* V */ {0, -2, -2, -2, -2, -1, -1, -2, 4, 0, -2, 2, 2, -2,_M, -1, -2, -2, -1, 0, 0, 4, -6, 0, -2, -2},
/* W */ {-6, -5, -8, -7, -7, 0, -7, -3, -5, 0, -3, -2, -4, -4,_M, -6, -5, 2, -2, -5, 0, -6, 17, 0, 0, -6},
/* X */ {0, 0, 0, 0, 0, 0, 0, 0, 0, 0, 0, 0, 0, 0, _M, 0, 0, 0, 0, 0, 0, 0, 0, 0, 0, 0},
/* Y */ {-3, -3, 0, -4, -4, 7, -5, 0, -1, 0, -4, -1, -2, -2, _M, -5, -4, -4, -3, -3, 0, -2, 0, 0, 10, -4},
/* Z */ {0, 1, -5, 2, 3, -5, 0, 2, -2, 0, 0, -2, -1, 1,_M, 0, 3, 0, 0, 0, 0, -2, -6, 0, -4, 4}
};
/*
*/ include <stdio.h>
include <ctype.h>
#define MAXJMP    16     /* max jumps in a diag */
#define MAXGAP    24     /* don't continue to penalize gaps larger than this */
#define JMPS      1024   /* max jmps in an path */
#define MX        4      /* save if there's at least MX-1 bases since last jmp */
#define DMAT      3      /* value of matching bases */
#define DMIS      0      /* penalty for mismatched bases */
#define DINS0     8      /* penalty for a gap */
#define DINS1     1      /* penalty per base */
```

TABLE 1-continued

```
#define PINS0         8        /* penalty for a gap */
#define PINS1         4        /* penalty per residue */
struct jmp {
    short         n[MAXJMP];    /* size of jmp (neg for dely) */
    unsigned short x[MAXJMP];   /* base no. of jmp in seq x */
                                /* limits seq to 2^16 -1 */
};
struct diag {
    int           score;        /* score at last jmp */
    long          offset;       /* offset of prev block */
    short         ijmp;         /* current jmp index */
    struct jmp    jp;           /* list of jmps */
};
struct path {
    int           spc;          /* number of leading spaces */
    short         n[JMPS];/* size of jmp (gap) */
    int           x[JMPS];/* loc of jmp (last elem before gap) */
};
char          *ofile;           /* output file name */
char          *namex[2];        /* seq names: getseqs() */
char          *prog;            /* prog name for err msgs */
char          *seqx[2];         /* seqs: getseqs() */
int           dmax;             /* best diag: nw() */
int           dmax0;            /* final diag */
int           dna;              /* set if dna: main() */
int           endgaps;          /* set if penalizing end gaps */
int           gapx, gapy;       /* total gaps in seqs */
int           len0, len1;       /* seq lens */
int           ngapx, ngapy;     /* total size of gaps */
int           smax;             /* max score: nw() */
int           *xbm;             /* bitmap for matching */
long          offset;           /* current offset in jmp file */
struct  diag  *dx;              /* holds diagonals */
struct  path  pp[2];            /* holds path for seqs */
char          *calloc(), *malloc(), *index(), *strcpy();
char          *getseq(), *g_calloc();
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with ⅓ or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static  __dbval[26] = {
    1,14,2,13,0,0,4,11,0,0,12,0,3,15,0,0,0,5,6,8,8,7,9,0,10,0
};
static  __pbval[26] = {
    1, 2|(1< <('D'–'A'))|(1< <('N'–'A')), 4, 8, 16, 32, 64,
    128, 256, 0xFFFFFFF, 1< <10, 1< <11, 1< <12, 1< <13, 1< <14,
    1< <15, 1< <16, 1< <17, 1< <18, 1< <19, 1< <20, 1< <21, 1< <22,
    1< <23, 1< <24, 1< <25|(1< <('E'–'A'))|(1< <('Q'–'A'))
};
main(ac, av)                                                                                                main
    int       ac;
    char      *av[];
{
    prog = av[0];
    if(ac != 3) {
        fprintf(stderr, "usage: %s file1 file2\n", prog);
        fprintf(stderr, "where file1 and file2 are two dna or two protein sequences.\n");
        fprintf(stderr, "The sequences can be in upper- or lower-case\n");
        fprintf(stderr, "Any lines beginning with ';' or '<' are ignored\n");
        fprintf(stderr, "Output is in the file \"align.out\"\n");
        exit(1);
    }
    namex[0] = av[1];
    namex[1] = av[2];
```

TABLE 1-continued

```
    seqx[0] = getseq(namex[0], &len0);
    seqx[1] = getseq(namex[1], &len1);
    xbm = (dna)? _dbval : _pbval;
    endgaps = 0;          /* 1 to penalize endgaps */
    ofile = "align.out";   /* output file */
    nw();                 /* fill in the matrix, get the possible jmps */
    readjmps();           /* get the actual jmps */
    print();              /* print stats, alignment */
    cleanup(0);           /* unlink any tmp files */
}
/* do the alignment, return best score: main()
 * dna: values in Fitch and Smith, PNAS, 80, 1382–1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                                        nw
{
    char      *px, *py;      /* seqs and ptrs */
    int       *ndely, *dely; /* keep track of dely */
    int       ndelx, delx;   /* keep track of delx */
    int       *tmp;          /* for swapping row0, row1 */
    int       mis;           /* score for each type */
    int       ins0, ins1;    /* insertion penalties */
    register  id;            /* diagonal index */
    register  ij;            /* jmp index */
    register  *col0, *col1;  /* score for curr, last row */
    register  xx, yy;        /* index into seqs */
    dx = ( struct diag *)g_calloc("to get diags", len0 + len1 + 1, sizeof(struct diag));
    ndely = (int *)g_calloc("to get ndely", len1 + 1, sizeof(int));
    dely = (int *)g_calloc("to get dely", len1 + 1, sizeof(int));
    col0 = (int *)g_calloc("to get col0", len1 + 1, sizeof(int));
    col1 = (int *)g_calloc("to get col1", len1 + 1, sizeof(int));
    ins0 = (dna)? DINS0 : PINS0;
    ins1 = (dna)? DINS1 : PlNS1;
    smax = -10000;
    if (endgaps) {
        for (col0[0] = dely[0] = -ins0, yy = 1; yy <= len1; yy++) {
            col0[yy] = dely[yy] = col0[yy-1] - ins1;
            ndely[yy] = yy;
        }
        col0[0] = 0;        /* Waterman Bull Math Biol 84 */
    }
    else
        for (yy = 1; yy <= len1; yy++)
            dely[yy] = -ins0;
    /* fill in match matrix
     */
    for (px = seqx[0], xx = 1; xx <= len0; px++, xx++) {
        /* initialize first entry in col
         */
        if (endgaps) {
            if (xx == 1)
                col1[0] = delx = -(ins0 + ins1);
            else
                col1[0] = delx = col0[0] - ins1;
            ndelx = xx;
        }
        else {
            col1[0] = 0;
            delx = -ins0;
            ndelx = 0;
        }
                                                                                            ...nw
        for (py = seqx[1], yy = 1; yy <= len1; py++, yy++) {
            mis = col0[yy-1];
            if (dna)
                mis + = (xbm[*px-'A']&xbm[*py-'A'])? DMAT : DMIS;
            else
                mis += _day[*px-'A'][*py-'A'];
            /* update penalty for del in x seq;
             * favor new del over ongong del
             * ignore MAXGAP if weighting endgaps
             */
```

TABLE 1-continued

```
            if (endgaps || ndely[yy] < MAXGAP) {
                if (col0[yy] - ins0 >= dely[yy]) {
                    dely[yy] = col0[yy] - (ins0+ins1);
                    ndely[yy] = 1;
                } else {
                    dely[yy] -= ins1;
                    ndely[yy]++;
                }
            } else {
                if (col0[yy] - (ins0+ins1) >= dely[yy]) {
                    dely[yy] = col0[yy] - (ins0+ins1);
                    ndely[yy] = 1;
                } else
                    ndely[yy]++;
            }
            /* update penalty for del in y seq;
             * favor new del over ongong del
             */
            if (endgaps || ndelx < MAXGAP) {
                if (col1[yy-1] - ins0 >= delx) {
                    delx = col1[yy-1] - (ins0+ins1);
                    ndelx = 1;
                } else {
                    delx -= ins1;
                    ndelx++;
                }
            } else {
                if (col1[yy-1] - (ins0+ins1) >= delx) {
                    delx = col1[yy-1] - (ins0+ins1);
                    ndelx = 1;
                } else
                    ndelx++;
            }
            /* pick the maximum score; we're favoring
             * mis over any del and delx over dely
             */
                                                                            ...nw
            id = xx - yy + len1 - 1;
            if (mis >= delx && mis >= dely[yy])
                col1[yy] = mis;
            else if (delx >= dely[yy]) {
                col1[yy] = delx;
                ij = dx[id].ijmp;
                if (dx[id].jp.n[0] && (!dna || (ndelx >= MAXJMP
                    && xx > dx[id].jp.x[ij]+MX) || mis > dx[id].score+DINS0)) {
                    dx[id].ijmp++;
                    if (++ij >= MAXJMP) {
                        writejmps(id);
                        ij = dx[id].ijmp = 0;
                        dx[id].offset = offset;
                        offset += sizeof(struct jmp) + sizeof(offset);
                    }
                }
                dx[id].jp.n[ij] = ndelx;
                dx[id].jp.x[ij] = xx;
                dx[id].score = delx;
            }
            else {
                col1[yy] = dely[yy];
                ij = dx[id].ijmp;
if (dx[id].jp.n[0] && (!dna || (ndely[yy] >= MAXJMP
                    && xx > dx[id].jp.x[ij]+MX) || mis > dx[id].score+DINS0)) {
                    dx[id].ijmp ++;
                    if (++ij >= MAXJMP) {
                        writejmps(id);
                        ij = dx[id].ijmp = 0;
                        dx[id].offset = offset;
                        offset += sizeof(struct jmp) + sizeof(offset);
                    }
                }
                dx[id].jp.n[ij] = -ndely[yy];
                dx[id].jp.x[ij] = xx;
                dx[id].score = dely[yy];
            }
```

TABLE 1-continued

```
            if (xx == len0 && yy < len1) {
                /* last col
                 */
                if (endgaps)
                    col1[yy] -= ins0+ins1*(len1-yy);
                if(col1[yy] > smax) {
                    smax = col1[yy];
                    dmax = id;
                }
            }
        }
        if (endgaps && xx < len0)
            col1[yy-1] -= ins0+ins1*(len0-xx);
        if (col1[yy-1] > smax) {
            smax = col1[yy-1];
            dmax = id;
        }
        tmp = col0; col0 = col1; col1 = tmp;
    }
    (void) free((char *)ndely);
    (void) free((char *)dely);
    (void) free((char *)col0);
    (void) free((char *)col1);
}
/*
*
* print() -- only routine visible outside this module
*
* static:
* getmat() -- trace back best path, count matches: print()
* pr_align() -- print alignment of described in array p[ ]: print()
* dumpblock() -- dump a block of lines with numbers, stars: pr_align()
* nums() -- put out a number line: dumpblock()
* putline() -- put out a line (name, [num], seq, [num]): dumpblock()
* stars() - -put a line of stars: dumpblock()
* stripname() -- strip any path and prefix from a seqname
*/
#include "nw.h"
#define SPC           3
#define P__LINE     256      /* maximum output line */
#define P__SPC        3      /* space between name or num and seq */
extern      __day[26][26];
int         olen;            /* set output line length */
FILE        *fx;             /* output file */
print()                                                                                                    print
{
    int     lx, ly, firstgap, lastgap;    /* overlap */
    if ((fx = fopen(ofile, "w")) == 0) {
        fprintf(stderr, "%s: can't write %s\n", prog, ofile);
        cleanup(1);
    }
    fprintf(fx, "<first sequence: %s (length = %d)\n", namex[0], len0);
    fprintf(fx, "<second sequence: %s (length = %d)\n", namex[1], len1);
    olen = 60;
    lx = len0;
    ly = len1;
    firstgap = lastgap = 0;
    if (dmax < len1 - 1) {              /* leading gap in x */
        pp[0].spc = firstgap = len1 - dmax - 1;
        ly -= pp[0].spc;
    }
    else if (dmax > len1 - 1) {         /* leading gap in y */
        pp[1].spc = firstgap = dmax - (len1 - 1);
        lx -= pp[1].spc;
    }
    if (dmax0 < len0 - 1) {             /* trailing gap in x */
        lastgap = len0 - dmax0 -1;
        lx -= lastgap;
    }
    else if (dmax0 > len0 - 1) {        /* trailing gap in y */
        lastgap = dmax0 - (len0 - 1);
        ly -= lastgap;
    }
```

TABLE 1-continued

```
        getmat(lx, ly, firstgap, lastgap);
        pr_align();
}
/*
* trace back the best path, count matches
*/
static
getmat(lx, ly, firstgap, lastgap)                                                           getmat
        int        lx, ly;                  /* "core" (minus endgaps) */
        int        firstgap, lastgap;       /* leading trailing overlap */
{
        int                nm, i0, i1, siz0, siz1;
        char               outx[32];
        double             pct;
        register           n0, n1;
        register char      *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "< %d match%s in an overlap of %d: %.2f percent similarity\n",
                nm, (nm == 1)? "" : "es", lx, pct);
        fprintf(fx, "<gaps in first sequence: %d", gapx);                                  ...getmat
        if (gapx) {
                (void) sprintf(outx, "(%d %s%s)",
                        ngapx, (dna)? "base": "residue", (ngapx == 1)? "":"s");
                fprintf(fx, "% s", outx);
        fprintf(fx, ", gaps in second sequence: %d", gapy);
        if (gapy) {
                (void) sprintf(outx, "(%d %s%s)",
                        ngapy, (dna)? "base":"residue", (ngapy == 1)? "":"s");
                fprintf(fx, "%s", outx);
        }
        if (dna)
                fprintf(fx,
                        "\n<score: %d (match = %d, mismatch = %d, gap penalty = %d + %d per base)\n",
                        smax, DMAT, DMIS, DINS0, DINS1);
        else
                fprintf(fx,
                        "\n<score: %d (Dayhoff PAM 250 matrix, gap penalty = %d + %d per residue)\n",
                        smax, PINS0, PINS1);
        if (endgaps)
                fprintf(fx,
```

TABLE 1-continued

```
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */
/*
 * print alignment of described in struct path pp[]
 */
static
pr_align()
{
    int         nn;             /* char count */
    int         more;
    register    i;
    for (i = 0, lmax = 0; i < 2++) {
        nn = stripname(namex[i]);
        if (nn > lmax)
                lmax = nn;
        nc[i] = 1;
        ni[i] = 1;
        siz[i] = ij[i] = 0;
        ps[i] = seqx[i];
        po[i] = out[i];
    }
    for (nn = nm = 0, more = 1; more;) {
        for (i = more = 0; i < 2; i++) {
            /*
             * do we have more of this sequence?
             */
            if (!*ps[i])
                    continue;
            more ++;
            if (pp[i].spc) {    /* leading space */
                    *po[i]++ = ' ';
                    pp[i].spc--;
            }
            else if (siz[i]) {  /* in a gap */
                    *po[i]++ = '-';
                    siz[i]--;
            }
            else {              /* we're putting a seq element
                                 */
                    *po[i] = *ps[i];
                    if (islower(*ps[i]))
                            *ps[i] = toupper(*ps[i]);
                    po[i]++;
                    ps[i]++;
                    /*
                     * are we at next gap for this seq?
                     */
                    if (ni[i] == pp[i].x[ij[i]]) {
                            /*
                             * we need to merge all gaps
                             * at this location
                             */
                            siz[i] == pp[i].n[ij[i]++];
                            while (ni[i] == pp[i].x[ij[i]])
                                    siz[i] += pp[i].n[ij[i] ++];
                    }
                    ni[i] ++;
            }
        }
``` pr_align

...pr_align

TABLE 1-continued

```
            if (++nn == olen || !more && nn) {
                dumpblock();
                for (i = 0; i < 2; i++)
                    po[i] = out[i];
                nn = 0;
            }
        }
}
/*
* dump a block of lines, including numbers, stars: pr_align()
*/
static
dumpblock()                                                                                     dumpblock
{
    register i;
    for(i = 0; i < 2; i++)
        *po[i]-- = '\0';
                                                                                                ...dumpblock
    (void) putc('\n', fx);
    for (i = 0; i < 2; i++) {
        if (*out[i] && (*out[i] != ' ' || *(po[i]) != ' ')) {
            if (i == 0)
                nums(i);
            if (i == 0 && *out[1])
                stars();
            putline(i);
            if (i == 0 && *out[1])
                fprintf(fx, star);
            if (i == 1)
                nums(i);
        }
    }
}
/*
* put out a number line: dumpblock()
*/
static
nums(ix)                                                                                        nums
    int    ix;      /* index in out[] holding seq line */
{
    char        nline[P_LINE];
    register    i, j;
    register char   *pn, *px, *py;
    for(pn = nline, i = 0; i < lmax+P_SPC; i++, pn++)
        *pn = ' ';
    for (i = nc[ix], py = out[ix]; *py; py++, pn++) {
        if (*py == ' ' || *py == '-');
            *pn = ' ';
        else {
            if (i%10 == 0 || (i == 1 && nc[ix] != 1)) {
                j = (i < 0)? -i : i;
                for (px = pn; j; j /= 10, px--)
                    *px = j%10 + '0';
                if (i < 0)
                    *px = '-';
            }
            else
                *pn = ' ';
            i++;
        }
    }
    *pn = '\0';
    nc[ix] = i;
    for (pn = nline; *pn; pn++)
        (void) putc(*pn, fx);
    (void) putc('\n', fx);
}
/*
* put out a line (name, [num], seq, [num]): dumpblock()
*/
static
putline(ix)                                                                                     putline
    int    ix;
{
```

TABLE 1-continued

```
             int       i;
             register char   *px;
             for (px = namex[ix], i = 0; *px && *px != ':'; px++, i++)
                   (void) putc(*px, fx);
             for (;i < lmax + P_SPC; i++)
                   (void) putc(' ', fx);
             /* these count from 1:
              * ni[] is current element (from 1)
              * nc[] is number at start of current line
              */
             for (px = out[ix]; *px; px++)
                   (void) putc(*px&0x7F, fx);
             (void) putc('\n', fx);
       }
/*
 * put a line of stars (seqs always in out[0], out[1]): dumpblock()
 */
static
stars()
{
             int       i;
             register char   *p0, *p1, cx, *px;
             if    (!*out[0] || (*out[0] == ' ' && *(p0[0]) == ' ') ||
                    !*out[1] || (*out[1] == ' ' && *(po[1]) == ' '))
                    return;
             px = star;
             for (i = lmax + P_SPC; i; i--)
                   *px++ = ' ';
             for (p0 = out[0], p1 = out[1]; *p0 && *p1; p0++, p1++) {
                   if (isalpha(*p0) && isalpha(*p1)) {
                         if (xbm[*p0-'A']&xbm[*p1-'A']) {
                               cx = '*';
                               nm++;
                         }
                         else if (!dna && _day[*p0- 'A'][*p1-'A'] > 0)
                               cx = '.';
                         else
                               cx = ' ';
                   }
                   else
                         cx = ' ';
                   *px++ = cx;
             }
             *px++ = '\n';
             *px = '\0';
}
/*
 * strip path or prefix from pn, return len: pr_align()
 */
static
stripname(pn)
       char      *pn;         /* file name (may be path) */
{
       register char        *px, *py;
       py = 0;
       for (px = pn; *px; px++)
             if (*px == '/')
                   py = px + 1;
       if (py)
             (void) strcpy(pn, py);
       return(strlen(pn));
}
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
#include "nw.h"
#include <sys/file.h>
char   *jname = "/tmp/homgXXXXXX";     /* tmp file for jmps */
FILE   *fj;
int    cleanup();                       /* cleanup tmp file */
long   lseek();
/*
 * remove any tmp file if we blow
 */
```

...putline stars stripname

TABLE 1-continued

```
cleanup(i)                                                                                                    cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                                                                             getseq
        char    *file;          /* file name */
        int     *len;           /* seq len */
{
        char                    line[1024], *pseq;
        register char           *px, *py;
        int                     natgc, tlen;
        FILE                    *fp;
        if ((fp = fopen(file, "r")) == 0) {
            fprintf(stderr, "%s: can't read %s\n", prog, file);
            exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr, "%s: malloc() failed to get %d bytes for %s\n", prog, tlen+6, file);
                exit(1);
        }
        pseq[0] = pseq[1] = pseq[2] = pseq[3] = '\0';
                                                                                                             ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU", *(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                                                         g_calloc
        char    *msg;           /* program, calling routine */
        int     nx, sz;         /* number and size of elements */
{
        char            *px, *calloc();
        if ((px = calloc((unsigned)nx, (unsigned)sz)) == 0) {
                if (*msg) {
                        fprintf(stderr, "%s: g_calloc() failed %s (n= %d, sz= %d)\n", prog, msg, nx, sz);
                        exit(1);
                }
        }
        return(px);
}
/*
 * get final jmps from dx[] or tmp file, set pp[], reset dmax: main()
 */
readjmps()                                                                                                    readjmps
{
```

TABLE 1-continued

```
    int        fd = -1;
    int        siz, i0, i1;
    register i, j, xx;
    if (fj) {
        (void) fclose(fj);
        if ((fd = open(jname, O_RDONLY, 0)) < 0) {
            fprintf(stderr, "%s: can't open() %s\n", prog, jname);
            cleanup(1);
        }
    }
    for (i = i0 = i1 = 0, dmax0 = dmax, xx = len0; ; i++) {
        while (1) {
            for (j = dx[dmax].ijmp; j >= 0 && dx[dmax].jp.x[j] >= xx; j--)
                                                                                ...readjmps
                ;
            if (j < 0 && dx[dmax].offset && fj) {
                (void) lseek(fd, dx[dmax].offset, 0);
                (void) read(fd, (char *)&dx[dmax].jp, sizeof(struct jmp));
                (void) read(fd, (char *)&dx[dmax].offset, sizeof(dx[dmax].offset));
                dx[dmax].ijmp = MAXJMP-1;
            }
            else
                break;
        }
        if (i >= JMPS) {
            fprintf(stderr, "%s: too many gaps in alignment\n", prog);
            cleanup(1);
        }
        if (j >= 0) {
            siz = dx[dmax].jp.n[j];
            xx = dx[dmax].jp.x[j];
            dmax += siz;
            if (siz < 0) {              /* gap in second seq */
                pp[1].n[i1] = -siz;
                xx += siz;
                /* id = xx - yy + len1 - 1
                 */
                pp[1].x[i1] = xx - dmax + len1 - 1;
                gapy++;
                ngapy -= siz;
/* ignore MAXGAP when doing endgaps */
                siz = (-siz < MAXGAP || endgaps)? -siz : MAXGAP;
                i1++;
            }
            else if (siz > 0) {         /* gap in first seq */
                pp[0].n[i0] = siz;
                pp[0].x[i0] = xx;
                gapx++;
                ngapx += siz;
/* ignore MAXGAP when doing endgaps */
                siz = (siz < MAXGAP || endgaps)? siz : MAXGAP;
                i0++;
            }
        }
        else
            break;
    }
    /* reverse the order of jmps
     */
    for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
    }
    for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
    }
    if (fd >= 0)
        (void) close(fd);
    if (fj) {
        (void) unlink(jname);
        fj = 0;
        offset = 0;
    }
}
/*
```

TABLE 1-continued

```
* write a filled jmp struct offset of the prev one (if any): nw()
*/
writejmps(ix)                                                                    writejmps
    int     ix;
{
    char    *mktemp();
    if (!fj) {
        if (mktemp(jname) < 0) {
            fprintf(stderr, "%s: can't mktemp() %s\n", prog, jname);
            cleanup(1);
        }
        if ((fj = fopen(jname, "w")) == 0) {
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

1. Full-length PRO1800 Polypeptides

Using the WU-BLAST2 sequence alignment computer program, it has been found that a portion of the full-length native sequence PRO1800 (shown in FIG. 2 and SEQ ID NO:2) has certain amino acid sequence identity with the human Hep27 protein (HE27_HUMAN). Accordingly, it is presently believed that PRO1800 disclosed in the present application is a newly identified Hep27 homolog and possesses activity typical of that protein.

2. Full-length PRO539 Polypeptides

Using the WU-BLAST2 sequence alignment computer program, it has been found that a portion of the full-length native sequence PRO539 (shown in FIG. 4 and SEQ ID NO:7) has certain amino acid sequence identity with a portion of a kinesin-related protein from *Drosophila melanogaster* (AF019250_1). Accordingly, it is presently believed that PRO539 disclosed in the present application is a newly identified member of the Hedgehog signaling pathway protein family and possesses activity typical of the Drosophila Costal-2 protein.

3. Full-length PRO982 Polypeptides

As far as is known, the DNA57700-1408 sequence encodes a novel secreted factor designated herein as PRO982. Although, using WU-BLAST2 sequence alignment computer programs, some sequence identities with known proteins were revealed.

4. Full-length PRO1434 Polypeptides

Using the WU-BLAST2 sequence alignment computer program, it has been found that a portion of the full-length native sequence PRO1434 (shown in FIG. 8 and SEQ ID NO:11) has certain amino acid sequence identity with the mouse nel protein precursor (NEL_MOUSE). Accordingly, it is presently believed that PRO1434 disclosed in the present application is a newly identified nel homolog and may possess activity typical of the nel protein family.

5. Full-length PRO1863 Polypeptides

The DNA59847-2510 clone was isolated from a human prostate tissue library. As far as is known, the DNA59847-2510 sequence encodes a novel factor designated herein as PRO1863; using the WU-BLAST2 sequence alignment computer program, no significant sequence identities to any known proteins were revealed.

6. Full-length PRO1917 Polypeptides Using WU-BLAST2 sequence alignment computer programs, it has been found that amino acids 41 to 487 of PRO1917 (shown in FIG. 12 and SEQ ID NO:18) has certain amino acid sequence identity with an inositol phosphatase designated in the Dayhoff database as "AF012714_1". Accordingly, it is presently believed that PRO1917 disclosed in the present application is a newly identified member of inositol phosphatase family and may possess enzymatic activity typical of inositol phosphatases.

7. Full-length PRO1868 Polypeptides

Using the WU-BLAST2 sequence alignment computer program, it has been found that a portion of the full-length native sequence PRO1868 (shown in FIG. 14 and SEQ ID NO:20) has certain amino acid sequence identity with the human A33 antigen protein (P_W14146). Accordingly, it is presently believed that PRO1868 disclosed in the present application is a newly identified A33 antigen homolog which may possess activity and/or expression patterns typical of the A33 antigen protein. The PRO1868 polypeptide may find use in the therapeutic treatment of inflammatory diseases as described above and colorectal cancer.

8. Full-length PRO3434 Polypeptides

The DNA77631-2537 clone was isolated from a human aortic tissue library using a trapping technique that selects for nucleotide sequences encoding secreted proteins. As far as is known, the DNA77631-2537 sequence encodes a novel factor designated herein as PRO3434; using the WU-BLAST2 sequence alignment computer program, no significant sequence identities to any known proteins were revealed.

9. Full-length PRO1927 Polypeptides

Using WU-BLAST2 sequence alignment computer programs, it has been found that a full-length native sequence PRO1927 (FIG. 18; SEQ ID NO:24) has certain amino acid sequence identity with the amino acid sequence of the protein designated "AB000628_1" in the Dayhoff database. Accordingly, it is presently believed that PRO1927 disclosed in the present application is a newly identified member of the glycosyltransferase family of proteins and may possess glycosylation activity.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 1 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |

TABLE 6-continued

| Original Residue | Exemplary Substitutions | Preferred Substitutions |
| --- | --- | --- |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in functionor immunologicalidentity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties. W. H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*. 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology,* 52:456–457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa,* and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tona ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published May 2, 1985); Kluyveromyces hosts (U.S. Pat. No. 4,943,529; Fleer et al., *Bio/Technology,* 9:968–975 (1991)) such as, e.g., *K. lactis* (MW98-8C, CBS683, CBS4574; Louvencourt et al., *J. Bacteriol.,* 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus*; yarrowia (EP 402,226); *Pichia pastoris* (EP 183,070; Sreekrishna et al., *J. Basic Microbiol.,* 28:265–278 [1988]); Candida; *Trichoderma reesia* (EP 244,234); *Neurospora crassa* (Case et al., *Proc. Natl. Acad. Sci. USA,* 76:5259–5263 [1979]); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.,* 112:284–289 [1983]; Tilbum et al., *Gene,* 26:205–221 [1983]; Yelton et al., *Proc. Natl. Acad. Sci. USA,* 81: 1470–1474 [1984]) and *A. niger* (Kelly and Hynes, *EMBO J.,* 4:475–479 [1985]). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs,* 269 (1982).

Suitable host cells for the expression of glycosylated PRO are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphateisomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293:620–625 (1981); Mantei et al., *Nature,* 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology* 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, -4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795–799 (1996); Yasuda, *Biomed. Ther.*, 27:1221–1223 (1993); Hora et al., *Bio/Technology*, 8:755–758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245–246 (1989); Chien et al., *Proc. Natl. Acad. Sci. USA*, 88:9578–9582 (1991)) as disclosed by Chevray and Nathans, *Proc. Natl. Acad. Sci. USA*, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.* 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522–525 (1986); Riechmann et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al., *Nature,* 332:323–327 (1988); Verhoeyen et al., *Science,* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.,* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection WO 91/00360; WO 92/200373; EP 030891. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity may also be prepared using heterobifunctional cross-linkers as described in Wolff et al. *Cancer Research*, 53: 2560–2565 (1993). Alternatively, an antibody can be engineered that has dual Fc regions and may thereby have enhanced complement lysis and ADCC capabilities. See Stevenson et al., *Anti-Cancer Drug Design.* 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generationof such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatizedphosphatidylethanolamine(PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286–288 (1982) via a disulfide-interchange reaction. A chemotherapeutic agent (such as Doxorubicin) is optionally contained within the liposome. See Gabizon et al., *J. National Cancer Inst.* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889–7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfideinterchange, stabilization may be achieved by modifying sulfhydryl residues, lyophilizing from acidic solutions, controlling moisture content, using appropriate additives, and developing specific polymer matrix compositions.

G. Uses for anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278–1280 (1991)) in the unique XhoI and NotI sites.

Example 2

Isolation of cDNA clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500–1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol debydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p–4p) or the complex formation of these proteins may also be preferably employed in combination with the amylase-expressing yeast.

Transformation was performed based on the protocol outlined by Gietz et al., *Nucl. Acid. Res.,* 20:1425 (1992). Transformed cells were then inoculated from agar into YEPD complex media broth (100 ml) and grown overnight at 30° C. The YEPD broth was prepared as described in Kaiser et al., *Methods in Yeast Genetics,* Cold Spring Harbor Press, Cold Spring Harbor, N.Y., p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol.<10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics,* Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., *Anal. Biochem.,* 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

```
                                              (SEQ ID NO:25)
5'-TGTAAAACGACGGCCAGTTAAATAGACCTGCAATTATTAATCT-3'
```

The sequence of reverse oligonucleotide 2 was:

```
                                              (SEQ ID NO:26)
5'-CAGGAAACAGCTATGACCACCTGCACACCTGCAAATCCATT-3'
```

PCR was then perfoemed as follows:

| a. |            | Denature | 92° C., | 5 minutes  |
|----|------------|----------|---------|------------|
| b. | 3 cycles of: | Denature | 92° C., | 30 seconds |
|    |            | Anneal   | 59° C., | 30 seconds |
|    |            | Extend   | 72° C., | 60 seconds |
| c. | 3 cycles of: | Denature | 92° C., | 30 seconds |
|    |            | Anneal   | 57° C., | 30 seconds |
|    |            | Extend   | 72° C., | 60 seconds |
| d. | 25 cycles of: | Denature | 92° C., | 30 seconds |
|    |            | Anneal   | 55° C., | 30 seconds |
|    |            | Extend   | 72° C., | 60 seconds |
| e. |            | Hold     | 4° C.   |            |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA clones Encoding Human PRO1800

A consensus DNA sequence was assembled relative to other EST sequences using phrap as described in Example I above. This consensus sequence is herein designated DNA30934. Based on the DNA30934 consensus sequence, oligonucleotides were synthesized: 1) to identify by PCR a cDNA library that contained the sequence of interest, and 2) for use as probes to isolate a clone of the full-length coding sequence for PRO1800.

PCR primers (forward and reverse) were synthesized:

```
forward PCR primer (30934.f1)
5'-GCATAATGGATGTCACTGAGG-3'            (SEQ ID NO:3)

reverse PCR primer (30934.r1)
5'-AGAACAATCCTGCTGAAAGCTAG-3'          (SEQ ID NO:4)
```

Additionally, a synthetic oligonucleotide hybridization probe was constructed from the consensus DNA30934 sequence which had the following nucleotide sequence Hybridization Probe (30934.p1)
5'-GAAACGAGGAGGCGGCTCAGTGGTGATCG TGTCTTCCATAGCAGCC-3' (SEQ ID NO :5)

RNA for construction of the cDNA libraries was isolated from human fetal liver tissue. DNA sequencing of the clones isolated as described above gave the full-length DNA sequence for PRO1800 (designated herein as DNA35672-2508 [FIG. 1, SEQ ID NO:1]; and the derived protein sequence for PRO1800.

The entire nucleotide sequence of DNA35672-2508 is shown in FIG. 1 (SEQ ID NO:1). Clone DNA35672-2508 contains a single open reading frame with an apparent translational initiation site at nucleotide positions 36–38 and ending at the stop codon at nucleotide positions 870–872 (FIG. 1). The predicted polypeptide precursor is 278 amino acids long (FIG. 2). The full-length PRO1800 protein shown in FIG. 2 has an estimated molecular weight of about 29,537 daltons and a pI of about 8.97. Analysis of the full-length PRO1800 sequence shown in FIG. 2 (SEQ ID NO:2) evidences the presence of the following: a signal peptide from about amino acid 1 to about amino acid 15, a potential N-glycosylation site from about amino acid 183 to about amino acid 186, potential N-myristolation sites from about amino acid 43 to about amino acid 48, from about amino acid 80 to about amino acid 85, from about amino acid 191 to about amino acid 196, from about amino acid 213 to about amino acid 218 and from about amino acid 272 to about amino acid 277 and a microbodies C-terminal targeting signal from about amino acid 276 to about amino acid 278. Clone DNA35672-2508 has been deposited with ATCC on Dec 15, 1998 and is assigned ATCC deposit no. 203538.

An analysis of the Dayhoff database (version 35.45 SwissProt 35), using a WU-BLAST2 sequence alignment analysis of the full-length sequence shown in FIG. 2 (SEQ ID NO:2), evidenced significant homology between the PRO1800 amino acid sequence and the following Dayhoff sequences: HE27_HUMAN, CELF36H9_1, CEF54F3_3, A69621, AP000007_227, UCPA_ECOLI, F69868, Y4LA_RHISN, DHK2_STRVN and DHG1_BACME.

Example 5

Isolation of cDNA clones Encoding Human PRO539

A consensus DNA sequence was assembled relative to other EST sequences using phrap as described in Example 1. This consensus sequence is herein designated DNA41882. Based on the DNA41882 consensus sequence shown, oligonucleotides were synthesized: 1) to identify by PCR a cDNA library that contained the sequence of interest, and 2) for use as probes to isolate a clone of the full-length coding sequence for PRO539.

RNA for construction of the cDNA libraries was isolated from human fetal kidney tissue. DNA sequencing of the clones isolated as described above gave the full-length DNA sequence for PRO539 (designated herein as DNA47465-1561 [FIG. 3, SEQ ID NO:6]; and the derived protein sequence for PRO539.

The entire nucleotide sequence of DNA47465-1561 is shown in FIG. 3 (SEQ ID NO:6). Clone DNA47465-1561 contains a single open reading frame with an apparent translational initiation site at nucleotide positions 186–188 and ending at the stop codon at nucleotide positions 2676–2678 (FIG. 3). The predicted polypeptide precursor is 830 amino acids long (FIG. 4). The full-length PRO539 protein shown in FIG. 4 has an estimated molecular weight of about 95,029 daltons and a pI of about 8.26. Analysis of the full-length PRO539 sequence shown in FIG. 4 (SEQ ID NO:7) evidences the presence of the following: leucine zipper pattern sequences from about amino acid 557 to about amino acid 578 and from about amino acid 794 to about amino acid 815, potential N-glycosylation sites from about amino acid 133 to about amino acid 136 and from about amino acid 383 to about amino acid 386 and a kinesin-related protein Kif-4 coiled coil domain from about amino acid 231 to about amino acid 672. Clone DNA47465-1561 has been deposited with ATCC on Feb. 9, 1999 and is assigned ATCC deposit no. 203661.

An analysis of the Dayhoff database (version 35.45 SwissProt 35), using a WU-BLAST2 sequence alignment analysis of the full-length sequence shown in FIG. 4 (SEQ ID NO:7), evidenced homology between the PRO539 amino acid sequence and the following Dayhoff sequences: AF019250_1, KIF4_MOUSE, TRHY_HUMAN, A56514, G02520, MYSP_HUMAN, AF041382_1, A45592, HS125H2_1 and HS68O2_2.

Example 6

Isolation of cDNA clones Encoding Human PRO982

Use of the signal sequence algorithm described in Example 3 above allowed identification of a single Incyte EST sequence designated herein as Incyte EST cluster sequence no. 43715. This EST sequence was compared to a variety of EST databases which included public EST databases (e.g., GenBank) and a proprietary EST DNA database (LIFESEQ™, Incyte Pharmaceuticals, Palo Alto, Calif.) to identify existing homologies. The homology search was performed using the computer program BLAST or BLAST2 (Altshul et al., *Methods in Enzymology* 266:460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is designated DNA56095.

In light of an observed sequence homology between DNA56095 and Merck EST no. AA024389, Merck EST clone AA024389 was obtained and sequenced. The sequence, designated DNA57700-1408 (SEQ ID NO:8), is shown in FIG. 5. It is the full-length DNA sequence for PRO982.

The full length clone shown in FIG. 5 contains a single open reading frame with an apparent translational initiation site at nucleotide positions 26–28 and ending at the stop codon found at nucleotide positions 401–403 (SEQ ID NO:8). The predicted polypeptide precursor is 125 amino acids long, has a calculated molecular weight of approximately 14,198 daltons and an estimated pI of approximately 9.01. Analysis of the full-length PRO982 sequence shown in FIG. 6 (SEQ ID NO:9) evidences the presence of a signal peptide from about amino acid 1 to about amino acid 21 and potential anaphylatoxin domain from about amino acid 50 to about amino acid 59. An analysis of the Dayhoff database (version 35.45 SwissProt 35) evidenced homology between the PRO982 amino acid sequence and the following Dayhoff sequences: RNTMDCV_1; A48151; WAP_RAT; S24596; A53640; MT4_HUMAN; U93486_1; SYNBILGFG_1; P_R49917; and P_R41880. Clone DNA57700-1408 was deposited with the ATCC on Jan. 12, 1999 and is assigned ATCC deposit no. 203583.

Example 7

Isolation of cDNA clones Encoding Human PRO1434

A consensus DNA sequence was assembled relative to other EST sequences using phrap as described in Example I above. This consensus sequence is herein designated DNA54187. Based on the DNA54187 consensus sequence, oligonucleotides were synthesized: 1) to identify by PCR a cDNA library that contained the sequence of interest, and 2) for use as probes to isolate a clone of the full-length coding sequence for PRO1434.

PCR primers (forward and reverse) were synthesized:

```
forward PCR primer
5'-GAGGTGTCGCTGTGAAGCCAACGG-3'        (SEQ ID NO:12)

reverse PCR primer
5'-CGCTCGATTCTCCATGTGCCTTCC-3'        (SEQ ID NO:13)
```

Additionally, a synthetic oligonucleotide hybridization probe was constructed from the consensus DNA54187 sequence which had the following nucleotide sequence

```
Hybridization Probe
5'-GACGGAGTGTGTGGACCCTGTGTACG
   AGCCTGATCAGTGCTGTCC-3' (SEQ ID NO:14)
```

RNA for construction of the cDNA libraries was isolated from human retina tissue (LIB94). DNA sequencing of the clones isolated as described above gave the full-length DNA sequence for PRO1434 (designated herein as DNA68818-2536 [FIG. 7, SEQ ID NO:10]; and the derived protein sequence for PRO1434.

The entire nucleotide sequence of DNA68818-2536 is shown in FIG. 7 (SEQ ID NO:10). Clone DNA68818-2536 contains a single open reading frame with an apparent translational initiation site at nucleotide positions 581–583 and ending at the stop codon at nucleotide positions 1556–1558 (FIG. 7). The predicted polypeptide precursor is 325 amino acids long (FIG. 8). The full-length PRO1434 protein shown in FIG. 8 has an estimated molecular weight of about 35,296 daltons and a pI of about 5.37. Analysis of the full-length PRO1434 sequence shown in FIG. 8 (SEQ ID NO:11) evidences the presence of a variety of important protein domains as shown in FIG. 8. Clone DNA68818-2536 has been deposited with ATCC on Feb. 9, 1999 and is assigned ATCC deposit no. 203657.

An analysis of the Dayhoff database (version 35.45 SwissProt 35), using a WU-BLAST2 sequence alignment analysis of the full-length sequence shown in FIG. 8 (SEQ ID NO:11), evidenced significant homology between the PRO1434 amino acid sequence and the following Dayhoff sequences: NEL_MOUSE, APMU_PIG, P_W37501, NEL_RAT, TSP1_CHICK, P_W37500,NEL2_HUMAN, MMU010792_1, D86983_1 and 10 MUCS_BOVIN.

Example 8

Isolation of cDNA clones Encoding Human PRO1863

Use of the signal sequence algorithm described in Example 3 above allowed identification of an EST cluster sequence from the Incyte database, designated Incyte EST cluster sequence no. 82468. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56029.

In light of the sequence homology between the DNA56029 sequence and an EST sequence contained within the Incyte EST clone no. 2186536, the Incyte EST clone no. 2186536 was purchased and the cDNA insert was obtained and sequenced. The sequence of this cDNA insert is shown in FIG. 9 and is herein designated as DNA59847-2510.

Clone DNA59847-2510 contains a single open reading frame with an apparent translational initiation site at nucleotide positions 17–19 and ending at the stop codon at nucleotide positions 1328–1330 (FIG. 9). The predicted polypeptide precursor is 437 amino acids long (FIG. 10). The full-length PRO1863 protein shown in FIG. 10 has an estimated molecular weight of about 46,363 daltons and a pI of about 6.22. Analysis of the full-length PRO1863 sequence shown in FIG. 10 (SEQ ID NO:16) evidences the presence of the following: a signal peptide from about amino acid 1 to about amino acid 15, a transmembrane domain from about amino acid 243 to about amino acid 260, potential N-glycosylation sites from about amino acid 46 to about amino acid 49, from about amino acid 189 to about amino acid 192 and from about amino acid 382 to about amino acid 385, glycosaminoglycan attachment sites from about amino acid 51 to about amino acid 54 and from about amino acid 359 to about amino acid 362 and potential N-myristolation sites from about amino acid 54 to about amino acid 59, from about amino acid 75 to about amino acid 80, from about amino acid 141 to about amino acid 146, from about amino acid 154 to about amino acid 159, from about amino acid 168 to about amino acid 173, from about amino acid 169 to about amino acid 174, from about amino acid 198 to about amino acid 203, from about amino acid 254 to about amino acid 259, from about amino acid 261 to about amino acid 266, from about amino acid 269 to about amino acid 274, from about amino acid 284 to about amino acid 289, from about amino acid 333 to about amino acid 338, from about amino acid 347 to about amino acid 352, from about amino acid 360 to about amino acid 365, from about amino acid 361 to about amino acid 366, from about amino acid 388 to about amino acid 393, from about amino acid 408 to about amino acid 413 and from about amino acid 419 to about amino acid 424. Clone DNA59847-2510 has been deposited with ATCC on Jan. 12, 1999 and is assigned ATCC deposit no. 203576.

An analysis of the Dayhoff database (version 35.45 SwissProt 35), using a WU-BLAST2 sequence alignment analysis of the full-length sequence shown in FIG. 10 (SEQ ID NO:16), evidenced homology between the PRO1863 amino acid sequence and the following Dayhoff sequences: AF041083_1, P_W26579, HSA223603_1, MMU97068, RNMAGPIAN_1, CAHX_FLABR, S61882, AB007899_1, CAH1_FLALI and P_W13386.

Example 9

Isolation of cDNA clones Encoding Human PRO1917

Use of the signal sequence algorithm described in Example 3 above allowed identification of an EST cluster sequence from the LIFESEQ® database, designated EST cluster no. 85496. This EST cluster sequence was then compared to a the EST databases listed above to identify existing homologies. The homology search was performed using the computer program BLAST or BLAST2 (Altshul et al., *Methods in Enzymology* 266:460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56415.

In light of the sequence homology between the DNA56415 sequence and an EST sequence contained within EST no. 3255033, the EST clone, which derived from an ovarian tumor library, was purchased and the cDNA insert was obtained and sequenced. The sequence of this cDNA insert is shown in FIG. 11 and is herein designated as DNA76400-2528.

The full length clone shown in FIG. 11 contained a single open reading frame with an apparent translational initiation site at nucleotide positions 6–9 and ending at the stop codon found at nucleotide positions 1467–1469 (FIG. 11; SEQ ID NO:17). The predicted polypeptide precursor (FIG. 12, SEQ ID NO:18) is 487 amino acids long. PRO1917 has a calculated molecular weight of approximately 55,051 daltons and an estimated pI of approximately 8.14. Additional features include: a signal peptide at about amino acids 1–30; potential N-glycosylation sites at about amino acids 242–245 and 481484, protein kinase C phosphorylation sites at about amino acids 95–97, 182–184, and 427–429; N-myristoylation sites at about amino acids 107–112, 113–118, 117–122, 118–123, and 128–133; and an endoplasmic reticulum targeting sequence at about amino acids 484–487.

An analysis of the Dayhoff database (version 35.45 SwissProt 35), using a WU-BLAST2 sequence alignment analysis of the full-length sequence shown in FIG. 12 (SEQ ID NO:18), revealed significant homology between the PRO1917 amino acid sequence and Dayhoff sequence AF012714_1. Significant homology was also revealed between the PRO1917 amino acid sequence and the sequence of a chondrocyte protein, designated "P_W52286" on the Dayhoff database, which has been reported to be involved in the transition of chondrocytes from proliferate to hypertrophic states (International Patent Application Publication No. WO9801468-A1). Homology was also revealed between the PRO1917 amino acid sequence and the following additional Dayhoff sequences: P_W52286, GGU59420_1, P_R25597, PPA3_YEAST, PPA1_SCHPO, PPA2_SCHPO, A46783_1, DMC165H7_1, and AST8_DROME.

Clone DNA76400-2528 was deposited with the ATCC on Jan. 12, 1999, and is assigned ATCC deposit no. 203573.

Example 10

Isolation of cDNA clones Encoding Human PRO1868

A consensus DNA sequence was assembled relative to other EST sequences using phrap as described in Example 1 above. This consensus sequence is herein designated DNA49803. Based up an observed homology between the DNA49803 consensus sequence and an EST sequence contained within the Incyte EST clone no. 2994689, Incyte EST clone no. 2994689 was purchased and its insert obtained and sequenced. The sequence of that insert is shown in FIG. 13 and is herein designated DNA77624-2515.

The entire nucleotide sequence of DNA77624-2515 is shown in FIG. 13 (SEQ ID NO:19). Clone DNA77624-2515 contains a single open reading frame with an apparent translational initiation site at nucleotide positions 51–53 and ending at the stop codon at nucleotide positions 981–983 (FIG. 13). The predicted polypeptide precursor is 310 amino acids long (FIG. 14). The full-length PRO1868 protein shown in FIG. 14 has an estimated molecular weight of about 35,020 daltons and a pI of about 7.90. Analysis of the full-length PRO1868 sequence shown in FIG. 14 (SEQ ID NO:20) evidences the presence of the following: a signal peptide from about amino acid 1 to about amino acid 30, a transmembrane domain from about amino acid 243 to about amino acid 263, potential N-glycosylation sites from about amino acid 104 to about amino acid 107 and from about amino acid 192 to about amino acid 195, a cAMP- and cGMP-dependent protein kinase phosphorylation site from about amino acid 107 to about amino acid 110, casein kinase II phosphorylation sites from about amino acid 106 to about amino acid 109 and from about amino acid 296 to about amino acid 299, a tyrosine kinase phosphorylation site from about amino acid 69 to about amino acid 77 and potential N-myristolation sites from about amino acid 26 to about amino acid 31, from about amino acid 215 to about amino acid 220, from about amino acid 226 to about amino acid 231, from about amino acid 243 to about amino acid 248, from about amino acid 244 to about amino acid 249 and from about amino acid 262 to about amino acid 267. Clone DNA77624-2515 has been deposited with ATCC on Dec. 22, 1998 and is assigned ATCC deposit no. 203553.

An analysis of the Dayhoff database (version 35.45 SwissProt 35), using a WU-BLAST2 sequence alignment analysis of the full-length sequence shown in FIG. 14 (SEQ ID NO:20), evidenced significant homology between the PRO1868 amino acid sequence and the following Dayhoff sequences: HGS_RC75, P_W61379, A33_HUMAN, P_W14146, P_W14158, AMAL_DROME, P_R77437, I38346, NCM2_HUMAN and PTPD_HUMAN.

Example 11

Isolation of cDNA clones Encoding Human PRO3434

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56009.

In light of the sequence homology between the DNA56009 sequence and an EST sequence contained within the Incyte EST clone no 3327089, the Incyte EST clone no. 3327089 was purchased and the cDNA insert was obtained and sequenced. The sequence of this cDNA insert is shown in FIG. 15 and is herein designated as DNA77631-2537.

Clone DNA77631-2537 contains a single open reading frame with an apparent translational initiation site at nucleotide positions 46–48 and ending at the stop codon at nucleotide positions 3133–3135 (FIG. 15). The predicted polypeptide precursor is 1029 amino acids long (FIG. 16). The full-length PRO3434 protein shown in FIG. 16 has an estimated molecular weight of about 114,213 daltons and a pI of about 6.42. Analysis of the full-length PRO3434 sequence shown in FIG. 16 (SEQ ID NO:22) evidences the presence of very important polypeptide domains as shown in FIG. 16. Clone DNA77631-2537 has been deposited with ATCC on Feb. 9, 1999 and is assigned ATCC deposit no. 203651.

An analysis of the Dayhoff database (version 35.45 SwissProt 35), using a WU-BLAST2 sequence alignment analysis of the full-length sequence shown in FIG. 16 (SEQ ID NO:22), evidenced homology between the PRO3434 amino acid sequence and the following Dayhoff sequences: VATX_YEAST, P_R51171, POLS_IBDVP, IBDVORF_2. JC5043, IBDVPIV_1, VE7_HPV11, GEN14220, MUTS_THETH and COAC_CHICK.

Example 12

Isolation of cDNA clones Encoding Human PRO1927

Use of the signal sequence algorithm described in Example 3 above allowed identification of an EST cluster sequence from the LIFESEQ® database, designated EST Cluster No. 1913. This EST cluster sequence was then compared to a variety of expressed sequence tag (EST) databases which included the databases listed above, including an additional proprietary EST DNA database (Genentech, South San Francisco, Calif.) to identify existing homologies. The homology search was performed using the computer program BLAST or BLAST2 (Altshul et al., *Methods in Enzymology* 266:460–480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA73896.

In light of the sequence homology between the DNA73896 sequence and an EST sequence contained within EST no. 3326981H1, EST clone no. 3326981H1, which was obtained from a library constructed from RNA isolated from aortic tissue, was purchased and the cDNA insert was obtained and sequenced. The sequence of this cDNA insert is shown in FIG. 17 and is herein designated as "DNA82307-2531".

The full length clone shown in FIG. 17 contained a single open reading frame with an apparent translational initiation site at nucleotide positions 51–53 and ending at the stop codon found at nucleotide positions 1695–1697 (FIG. 17; SEQ ID NO:23). The predicted polypeptide precursor (FIG. 18, SEQ ID NO:24) is 548 amino acids long. PRO1927 has a calculated molecular weight of approximately 63,198 daltons and an estimated pI of approximately 8.10. Additional features include: a signal peptide at about amino acids 1–23; a putative transmembrane domain at about amino acids 6–25; potential N-glycosylation sites at about amino acids 5–8, 87–90, 103–106, and 465469; potential N-myristoylation sites at about amino acids 6–11, 136–141, 370–375, and 509–514.

An analysis of the Dayhoff database (version 35.45 SwissProt 35), using a WU-BLAST2 sequence alignment analysis of the full-length sequence shown in FIG. 18 (SEQ ID NO:24), revealed significant homology between the PRO1927 amino acid sequence and Dayhoff sequence AB000628_1. Homology was also revealed between the PRO1927 amino acid sequence and the following additional Dayhoff sequences: HGS_A251, HGS_A197, CELC50H11_2, CPXM_BACSU, VF03_VACCC, VF03_VACCV, DYHA_CHLRE, C69084, and A64315.

Clone DNA82307-2531 was deposited with the ATCC on Dec. 15, 1998, and is assigned ATCC deposit no. 203537.

Example 13

Inhibitory Activity in Mixed Lymphocyte Reaction (MLR) Assay (Assay 67)

This example shows that one or more of the polypeptides of the invention are active as inhibitors of the proliferation of stimulated T-lymphocytes. Compounds which inhibit proliferation of lymphocytes are useful therapeutically where suppression of an immune response is beneficial.

The basic protocol for this assay is described in Current Protocols in Immunology, unit 3.12; edited by J E Coligan, A M Kruisbeek, D H Marglies, E M Shevach, W Strober, National Insitutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3 \times 10^6$ cells/ml of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads).

The assay is prepared by plating in triplicate wells a mixture of:

100:1 of test sample diluted to 1% or to 0.1%,

50:1 of irradiated stimulator cells, and

50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1 \times 10^7$ cells/ml of assay media. The assay is then conducted as described above.

Any decreases below control is considered to be a positive result for an inhibitory compound, with decreases of less than or equal to 80% being preferred. However, any value less than control indicates an inhibitory effect for the test protein.

The following polypeptides tested positive in this assay: PRO1917 and PRO1868.

Example 14

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grams or more are anesthetized with ketamine (75–80 mg/Kg) and 5 mg/Kg xylazine intramuscularly (IM). A sample of purified polypeptide of the invention or a conditioned media test sample is injected intradermally onto the backs of the test animals with 100 µl per injection site. It is possible to have about 10–30, preferably about 16–24, injection sites per animal. One µl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positve, no infiltrate at the site of injection is scored as negative.

The following polypeptides tested positive in this assay: PRO1434.

Example 15

Proliferation of Rat Utricular Supporting Cells
(Assay 54)

This assay shows that certain polypeptides of the invention act as potent mitogens for inner ear supporting cells which are auditory hair cell progenitors and, therefore, are useful for inducing the regeneration of auditory hair cells and treating hearing loss in mammals. The assay is performed as follows. Rat UEC-4 utricular epithelial cells are aliquoted into 96 well plates with a density of 3000 cells/well in 200 μl of serum-containing medium at 33° C. The cells are cultured overnight and are then switched to serum-free medium at 37° C. Various dilutions of PRO polypeptides (or nothing for a control) are then added to the cultures and the cells are incubated for 24 hours. After the 24 hour incubation, $^3$H-thymidine (1 μCi/well) is added and the cells are then cultured for an additional 24 hours. The cultures are then washed to remove unincorporated radiolabel, the cells harvested and Cpm per well determined. Cpm of at least 30% or greater in the PRO polypeptide treated cultures as compared to the control cultures is considered a positive in the assay.

The following polypeptides tested positive in this assay: PRO982.

Example 16

Gene Amplification

This example shows that the PRO1800-, PRO539-, PRO3434- and PRO1927-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers and diagnostic determination of the presence of those cancers. Therapeutic agents may take the form of antagonists of PRO1800, PRO539, PRO3434 or PRO1927 polypeptide, for example, murine-human chimeric, humanized or human antibodies against a PRO1800, PRO539, PRO3434 or PRO1927 polypeptide.

The starting material for the screen was genomic DNA isolated from a variety cancers. The DNA is quantitated precisely, e.g., fluorometrically. As a negative control, DNA was isolated from the cells of ten normal healthy individuals which was pooled and used as assay controls for the gene copy in healthy individuals (not shown). The 5' nuclease assay (for example, TaqMan™) and real-time quantitative PCR (for example, ABI Prizm 7700 Sequence Detection System™ (Perkin Elmer, Applied Biosystems Division, Foster City, Calif.)), were used to find genes potentially amplified in certain cancers. The results were used to determine whether the DNA encoding PRO1800, PRO539, PRO3434 or PRO1927 is over-represented in any of the primary lung or colon cancers or cancer cell lines or breast cancer cell lines that were screened. The primary lung cancers were obtained from individuals with tumors of the type and stage as indicated in Table 7. An explanation of the abbreviations used for the designation of the primary tumors listed in Table 7 and the primary tumors and cell lines referred to throughout this example are given below.

The results of the TaqMan™ are reported in delta (Δ) Ct units. One unit corresponds to 1 PCR cycle or approximately a 2-fold amplification relative to normal, two units corresponds to 4-fold, 3 units to 8-fold amplification and so on. Quantitation was obtained using primers and a TaqMan™ fluorescent probe derived from the PRO1800-, PRO539-, PRO3434- or PRO1927-encoding gene. Regions of PRO1800, PRO539, PRO3434 or PRO1927 which are most likely to contain unique nucleic acid sequences and which are least likely to have spliced out introns are preferred for the primer and probe derivation, e.g., 3'-untranslated regions. The sequences for the primers and probes (forward, reverse and probe) used for the PRO1800, PRO539, PRO3434 or PRO1927 gene amplification analysis were as follows:

```
PRO1800  (DNA35672-2508)
forward  5'-ACTCGGGATTCCTGCTGTT-3'           (SEQ ID NO:27)
probe    5'-AGGCCTTTACCCAAGGCCACAAC-3'       (SEQ ID NO:28)
reverse  5'-GGCCTGTCCTGTGTTCTCA-3'           (SEQ ID NO:29)

PRO539   (DNA47465-1561)
forward  5'-TCCCACCACTTACTTCCATGAA-3'        (SEQ ID NO:30)
probe    5'-CTGTGGTACCCAATTGCCGCCTTGT-3'     (SEQ ID NO:31)
reverse  5'-ATTGTCCTGAGATTCGAGCAAGA-3'       (SEQ ID NO :32)

PRO3434  (DNA77631-2537)
forward  5'-GTCCAGCAAGCCCTCATT-3'            (SEQ ID NO:33)
probe    5'-CTTCTGGGCCACAGCCCTGC-3'          (SEQ ID NO:34)
reverse  5'-CAGTTCAGGTCGTTTCATTCA-3'         (SEQ ID NO:35)

PRO1927  (DNA82307-2531)
forward  5'-CCAGTCAGGCCGTTTTAGA-3'           (SEQ ID NO:36)
probe    5'-CGGGCGCCCAAGTAAAAGCTC-3'         (SEQ ID NO:37)
reverse  5'-CATAAAGTAGTATATGCATTCCAGTGTT-3'  (SEQ ID NO:38)
```

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700TM Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 7 describes the stage, T stage and N stage of various primary tumors which were used to screen the PRO1800, PRO539, PRO3434 and PRO1927 compounds of the invention.

TABLE 7

Primary Lung and Colon Tumor Profiles

| Primary Tumor Stage | Stage | Other Stage | Dukes Stage | T Stage | N Stage |
| --- | --- | --- | --- | --- | --- |
| Human lung tumor AdenoCa (SRCC724) [LT1] | IIA | | | T1 | N1 |
| Human lung tumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT7] | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735) [LT13] | IB | | | T2 | N0 |
| Human lung tumor SqCCa (SRCC736) [LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | 1A | | | T1 | N0 |
| Human colon AdenoCa (SRCC742) [CT2] | M1 | D | pT4 | N0 | |
| Human colon AdenoCa (SRCC743) [CT3] | | B | pT3 | N0 | |
| Human colon AdenoCa (SRCC744) [CT8] | | B | T3 | N0 | |
| Human colon AdenoCa (SRCC745) [CT10] | | A | pT2 | N0 | |
| Human colon AdenoCa (SRCC746) [CT12] | MO, R1 | B | T3 | N0 | |
| Human colon AdenoCa (SRCC747) [CT14] | pMO, RO | B | pT3 | pN0 | |
| Human colon AdenoCa (SRCC748) [CT15] | M1, R2 | D | T4 | N2 | |
| Human colon AdenoCa (SRCC749) [CT16] | pMO | B | pT3 | pN0 | |
| Human colon AdenoCa (SRCC750) [CT17] | | C1 | pT3 | pN1 | |
| Human colon AdenoCa (SRCC751) [CT1] | MO, R1 | B | pT3 | N0 | |
| Human colon AdenoCa (SRCC752) [CT4] | | B | pT3 | M0 | |
| Human colon AdenoCa (SRCC753) [CT5] | G2 | C1 | pT3 | pN0 | |
| Human colon AdenoCa (SRCC754) [CT6] | pMO, RO | B | pT3 | pN0 | |
| Human colon AdenoCa (SRCC755) [CT7] | G1 | A | pT2 | pN0 | |
| Human colon AdenoCa (SRCC756) [CT9] | G3 | D | pT4 | pN2 | |
| Human colon AdenoCa (SRCC757) [CT11] | | B | T3 | N0 | |
| Human colon AdenoCa (SRCC758) [CT18] | MO, RO | B | pT3 | pN0 | |

DNA Preparation:

DNA was prepared from cultured cell lines, primary tumors, normal human blood. The isolation was performed using purification kit, buffer set and protease and all from Quiagen, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 ml PBS. Buffer C1 was equilibrated at 4° C. Qiagen protease #19155 was diluted into 6.25 ml cold ddH$_2$O to a final concentration of 20 mg/ml and equilibrated at 4° C. 10 ml of G2 Buffer was prepared by diluting Qiagen RNAse A stock (100 mg/ml) to a final concentration of 200 µg/ml.

Buffer C1 (10 ml, 4° C.) and ddH2O (40 ml, 4° C.) were then added to the 10 ml of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 ml Buffer C1 (at 4° C.) and 6 ml ddH$_2$O, followed by a second 4° C. centrifugation at 2500 rpm for 15 minutes. The nuclei were then resuspended into the residual buffer using 200 µl per tip. G2 buffer (10 ml) was added to the suspended nuclei while gentle vortexing was applied. Upon completion of buffer addition, vigorous vortexing was applied for 30 seconds. Quiagen protease (200 µl, prepared as indicated above) was added and incubated at 50° C. for 60 minutes. The incubation and centrifugation was repeated until the lysates were clear (e.g., incubating additional 30–60 minutes, pelleting at 3000× g for 10 min., 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenized in 19 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2L ddH$_2$O, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000× g for 10 min., 4° C.).

Human Blood Preparation and Lysis:

Blood was drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200 µl tip. G2 buffer (10 ml) were added to the suspended nuclei while gently vortexing, followed by vigorous vortexing for 30 seconds. Quiagen protease was added (200 µl) and incubated at 50° C. for 60 minutes. The incubation and centrifugation was repeated until the lysates were clear (e.g., incubating additional 30–60 minutes, pelleting at 3000× g for 10 min., 4° C.).

Purification of Cleared Lysates:

(1) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

(2) Quantitation of Genomic DNA and Preparation for Gene Amplification Assay:

The DNA levels in each tube were quantified by standard $A_{260}$, $A_{280}$ spectrophotometry on a 1:20 dilution (5 µl DNA +95 µl ddH$_2$O) using the 0.1 ml quartz cuvetts in the Beckman DU640 spectrophotometer. $A_{260}/A_{280}$ ratios were in the range of 1.8–1.9. Each DNA samples was then diluted further to approximately 200 ng/ml in TE (pH 8.5). If the original material was highly concentrated (about 700 ng/µl), the material was placed at 50° C. for several hours until resuspended.

Fluorometric DNA quantitation was then performed on the diluted material (20–600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 µl, prepared within 12 hours of use) was diluted into 100 ml 1× TNE buffer. A 2 ml cuvette was filled with the fluorometer solution, placed into the machine, and the machine was zeroed. pGEM 3Zf(+) (2 µl, lot #360851026) was added to 2 ml of fluorometer solution and calibrated at 200 units. An additional 2 µl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometricly determined concentration was then used to dilute each sample to 10 ng/µl in ddH$_2$O. This was done simultaneously on all template samples for a single TaqMan plate assay, and with enough material to run 500–1000 assays. The samples were tested in triplicate with Taqman™ primers and probe both B-actin and GAPDH on a single plate with normal human DNA and no-template controls. The diluted samples were used provided that the CT value of normal human DNA subtracted from test DNA was +/−1 Ct. The diluted, lot-qualified genomic DNA was stored in 1.0 ml aliquots at −80° C. Aliquots which were subsequently to be used in the gene amplification assay were stored at 4° C. Each 1 ml aliquot is enough for 8–9 plates or 64 tests.

Gene Amplification Assay:

The PRO1800, PRO539, PRO3434 and PRO1927 compounds of the invention were screened in the following primary tumors and the resulting ΔCt values greater than or equal to 1.0 are reported in Table 8 below.

TABLE 8

(ΔCt values in lung and colon primary tumor models)

| Primary Tumor | PRO1800 | PRO539 | PRO3434 | PRO1927 |
|---|---|---|---|---|
| LT11 | 1.65, 1.59, 1.03 | | | |
| LT12 | 1.34, 2.28, 2.03 | 1.25 | | |
| LT13 | 1.27, 2.18 | 1.64, 1.08 | 5.24, 4.47 | 4.38, 4.80 |
| LT15 | 1.70, 2.23, 1.93 | 1.78, 1.10 | 1.24 | 1.00 |
| LT16 | 1.00, 1.05, 1.09 | | 3.65, 3.19 | 2.73, 2.74 |
| LT17 | 1.94, 1.63 | 1.94, 1.01 | | |
| LT18 | 1.12 | | | |
| LT19 | 2.51, 2.18 | 1.16 | | |
| LT21 | 1.30 | 1.32 | | |
| CT2 | 1.50 | | | |
| CT3 | | 1.17 | | |
| CT10 | | 1.16 | | |
| CT12 | | 1.19 | | |
| CT14 | 1.62 | | | |
| CT15 | 1.48, 1.08 | 1.03 | 1.19, 1.40 | 1.10, 1.30 |
| CT5 | 1.10 | | | |
| CT11 | 1.20 | 1.12 | | |
| Colo-320 (colon tumor cell line) | 1.16 | | 1.78, 1.76, 1.74 | 1.51 |
| HF-00084 (lung tumor cell line) | | | 2.20 | 2.41 |
| HCT-116 (colon tumor cell line) | | | 2.15, 2.22 | 1.41, 1.47 |
| HF-00129 (lung tumor cell line) | | | 1.00, 1.17, 4.64 1.11 | 2.31, 5.14 2.40 |
| SW-620 (colon tumor cell line) | | | 1.30 | |
| HT-29 (colon tumor cell line) | | | 1.64 | |
| SW-403 (colon tumor cell line) | | | 1.75 | |
| LS174T (colon tumor cell line) | | | 1.42 | |
| HCC-2998 (colon tumor cell line) | | | 1.15 | |
| A549 (lung tumor cell line) | | | 1.51, 1.09 | |
| Calu-6 (lung tumor cell line) | | | 1.60, 1.22 | |
| H157 (lung tumor cell line) | | | 1.61 | |
| H441 (lung tumor cell line) | | | 1.07, 1.15 | |
| H460 (lung tumor cell line) | | | 1.01 | |
| SKMES1 (lung tumor cell line) | | | 1.02 | |
| H810 (lung tumor cell line) | | | 1.20, 1.54 | |

Example 17

Induction of Pancreatic β-Cell Precursor Proliferation (Assay 117)

This assay shows that certain polypeptides of the invention act to induce an increase in the number of pancreatic β-cell precursor cells and, therefore, are useful for treating various insulin deficient states in mammals, including diabetes mellitus. The assay is performed as follows. The assay uses a primary culture of mouse fetal pancreatic cells and the primary readout is an alteration in the expression of markers that represent either β-cell precursors or mature β-cells. Marker expression is measured by real time quantitative PCR (RTQ-PCR); wherein the marker being evaluated is a transcription factor called Pdx1.

The pancreata are dissected from E14 embryos (CD1 mice). The pancreata are then digested with collagenase/dispase in F12/DMEM at 37° C. for 40 to 60 minutes (collagenase/dispase, 1.37 mg/ml, Boehringer Mannheim, #1097113). The digestion is then neutralized with an equal volume of 5% BSA and the cells are washed once with RPMI 1640. At day 1, the cells are seeded into 12-well tissue culture plates (pre-coated with laminin, 20 μg/ml in PBS, Boehringer Mannheim, #124317). Cells from pancreata from 1–2 embryos are distributed per well. The culture medium for this primary cuture is 14F/1640. At day 2, the media is removed and the attached cells washed with RPMI/1640. Two mls of minimal media are added in addition to the protein to be tested. At day 4, the media is removed and RNA prepared from the cells and marker expression analyzed by real time quantitative RT-PCR. A protein is considered to be active in the assay if it increases the expression of the relevant β-cell marker as compared to untreated controls.

14F/1640 is RPMI1640 (Gibco) Plus the Following:
  group A 1:1000
  group B 1:1000
  recombinant human insulin 10 µg/ml
  Aprotinin (50 µg/ml) 1:2000 (Boehringer manheim #981532)
  Bovine pituitary extract (BPE) 60 µg/ml
  Gentamycin 100 ng/ml
Group A: (in 10 ml PBS)
  Transferrin, 100 mg (Sigma T2252)
  Epidermal Growth Factor, 100 µg (BRL 100004)
  Triiodothyronine, 10 µl of $5 \times 10^{-6}$ M (Sigma T5516)
  Ethanolamine, 100 µl of $10^{-1}$ M (Sigma E0135)
  Phosphoethalamine, 100 µl of $10^{-1}$ M (Sigma P0503)
  Selenium, 4 µl of $10^{-1}$ M (Aesar #12574)
Group C: (in 10 ml 100% Ethanol)
  Hydrocortisone, 2 µl of $5 \times 10^{-3}$ M (Sigma #H0135)
  Progesterone, 100 µl of $1 \times 10^{-3}$ M (Sigma #P6149)
  Forskolin, 500 µl of 20 mM (Calbiochem #344270)
Minimal Media:
  RPMI 1640 plus transferrin (10 µg/ml), insulin (1 µg/ml), gentamycin (100 ng/ml), aprotinin (50 µg/ml) and BPE (15 µg/ml).
Defined Media:
  RPMI 1640 plus transferrin (10 µg/ml), insulin (1 µg/ml), gentamycin (100 ng/ml) and aprotinin (50 µg/ml).
  The following polypeptide was positive in this assay: PRO1868.

Example 18

Induction of Pancreatic β-Cell Precursor Differentiation (Assay 89)

This assay shows that certain polypeptides of the invention act to induce differentiation of pancreatic β-cell precursor cells into mature pancreatic β-cells and, therefore, are useful for treating various insulin deficient states in mammals, including diabetes mellitus. The assay is performed as follows. The assay uses a primary culture of mouse fetal pancreatic cells and the primary readout is an alteration in the expression of markers that represent either β-cell precursors or mature β-cells. Marker expression is measured by real time quantitative PCR (RTQ-PCR); wherein the marker being evaluated is insulin.

The pancreata are dissected from E14 embryos (CD1 mice). The pancreata are then digested with collagenase/dispase in F12/DMEM at 37° C. for 40 to 60 minutes (collagenase/dispase, 1.37 mg/ml, Boehringer Mannheim, #1097113). The digestion is then neutralized with an equal volume of 5% BSA and the cells are washed once with RPM11640. At day 1, the cells are seeded into 12-well tissue culture plates (pre-coated with laminin, 20 µg/ml in PBS, Boehringer Mannheim, #124317). Cells from pancreata from 1–2 embryos are distributed per well. The culture medium for this primary cuture is 14F/1640. At day 2, the media is removed and the attached cells washed with RPMI/1640. Two mls of minimal media are added in addition to the protein to be tested. At day 4, the media is removed and RNA prepared from the cells and marker expression analyzed by real time quantitative RT-PCR. A protein is considered to be active in the assay if it increases the expression of the relevant β-cell marker as compared to untreated controls.

14F/1640 is RPMI1640 (Gibco) Plus the Following:
  group A 1:1000
  group B 1:1000
  recombinant human insulin 10 µg/ml
  Aprotinin (50 µg/ml) 1:2000 (Boehringer manheim #981532)
  Bovine pituitary extract (BPE) 60 µg/ml
  Gentamycin 100 ng/ml
Group A: (in 10 ml PBS)
  Transferrin, 100 mg (Sigma T2252)
  Epidermal Growth Factor, 100 µg (BRL 100004)
  Triiodothyronine, 10 µl of $5 \times 10^{-6}$ M (Sigma T5516)
  Ethanolamine, 100 µl of $10^{-1}$ M (Sigma E0135)
  Phosphoethalamine, 100 µl of $10^{-1}$ M (Sigma P0503)
  Selenium, 4 µl of $10^{-1}$ M (Aesar #12574)
Group C: (in 10 ml 100% Ethanol)
  Hydrocortisone, 2 µl of $5 \times 10^{-3}$ M (Sigma #H0135)
  Progesterone, 100 µl of $1 \times 10^{-3}$ M (Sigma #P6149)
  Forskolin, 500 µl of 20 mM (Calbiochem #344270)
Minimal Media:
  RPMI 1640 plus transferrin (10 µg/ml), insulin (1 µg/ml), gentamycin (100 ng/ml), aprotinin (50 µg/ml) and BPE (15 µg/ml).
Defined Media:
  RPMI 1640 plus transferrin (10 µg/ml), insulin (1 µg/ml), gentamycin (100 ng/ml) and aprotinin (50 µg/ml).
  The following polypeptide was positive in this assay: PRO1863.

Example 19

Mouse Kidney Mesangial Cell Proliferation Assay (Assay 92)

This assay shows that certain polypeptides of the invention act to induce proliferation of mammalian kidney mesangial cells and, therefore, are useful for treating kidney disorders associated with decreased mesangial cell function such as Berger disease or other nephropathies associated with Schönlein-Henoch purpura, celiac disease, dermatitis herpetiformis or Crohn disease. The assay is performed as follows. On day one, mouse kidney mesangial cells are plated on a 96 well plate in growth media (3:1 mixture of Dulbecco's modified Eagle's medium and Ham's F12 medium, 95% fetal bovine serum, 5% supplemented with 14 mM HEPES) and grown overnight. On day 2, PRO polypeptides are diluted at 2 concentrations(1% and 0.1%) in serum-free medium and added to the cells. Control samples are serum-free medium alone. On day 4, 20 µl of the Cell Titer 96 Aqueous one solution reagent (Progema) was added to each well and the colormetric reaction was allowed to proceed for 2 hours. The absorbance (OD) is then measured at 490 nm. A positive in the assay is anything that gives an absorbance reading which is at least 15% above the control reading.

The following polypeptide tested positive in this assay: PRO1917.

Example 20

Fibroblast (BHK-21) Proliferation (Assay 98)

This assay shows that certain polypeptides of the invention act to induce proliferation of mammalian fibroblast cells in culture and, therefore, function as useful growth factors in mammalian systems. The assay is performed as follows. BHK-21 fibroblast cells plated in standard growth medium at 2500 cells/well in a total volume of 100 µl . The PRO polypeptide, β-FGF (positive control) or nothing (negative control) are then added to the wells in the presence of 1 µg/ml of heparin for a total final volume of 200 µl. The cells are then incubated at 37° C. for 6 to 7 days. After incubation, the media is removed, the cells are washed with PBS and then an acid phosphatase substrate reaction mixture (100 µl/well) is added. The cells are then incubated at 37° C. for 2 hours. 10 µl per well of 1N NaOH is then added to stop the acid phosphatase reaction. The plates are then read at OD 405 nm. A positive in the assay is acid phosphatase activity which is at least 50% above the negative control.

The following polypeptide tested positive in this assay: PRO982.

Example 21

Chondrocyte Re-differentiation Assay (Assay 110)

This assay shows that certain polypeptides of the invention act to induce redifferentiation of chondrocytes, therefore, are expected to be useful for the treatment of various bone and/or cartilage disorders such as, for example, sports injuries and arthritis. The assay is performed as follows. Porcine chondrocytes are isolated by overnight collagenase digestion of articular cartilage of metacarpophalangeal joints of 4–6 month old female pigs. The isolated cells are then seeded at 25,000 cells/cm$^2$ in Ham F-12 containing 10% FBS and 4 µg/ml gentamycin. The culture media is changed every third day and the cells are then seeded in 96 well plates at 5,000 cells/well in 100 µl of the same media without serum and 100 µl of the test PRO polypeptide, 5 nM staurosporin (positive control) or medium alone (negative control) is added to give a final volume of 200 µl/well. After 5 days of incubation at 37° C., a picture of each well is taken and the differentiation state of the chondrocytes is determined. A positive result in the assay occurs when the redifferentiation of the chondrocytes is determined to be more similar to the positive control than the negative control.

The following polypeptide tested positive in this assay: PRO1863.

Example 22

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5× SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1× SSC and 0.1% SDS at 42° C.

DNAs having a desired sequence identity with the DNA encoding full-length native sequence PRO can then be identified using standard techniques known in the art.

Example 23

Expression of PRO in E. coli

This example illustrates preparation of an unglycosylated form of PRO by recombinant expression in E. coli.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene 2.95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in E. coli in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) Ion galE rpoHts(htpRts) clpP(lacIq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g (NH$_4$)$_2$SO$_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM MgSO$_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 24

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at -80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 25

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 26

Expression of PRO in Baculovirus-infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("*Sf9*") cells (ATCC CRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 27

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 28

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 29

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 30

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, *Bio/Technology*, 9: 19–21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*. 31:7796–7801 (1992) or which act as inhibitors, agonists, or antagonists of native peptides as shown by Athauda et al., *J. Biochem.*, 113:742–746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Deposit of Material

The following materials have been deposited with the American Type Culture Collection, 12301 Parklawn Drive, Rockville, Md., USA (ATCC):

| Material | ATCC Dep. No. | Deposit Date |
|---|---|---|
| DNA35672-2508 | 203538 | Dec. 15, 1998 |
| DNA47465-1561 | 203661 | Feb. 9, 1999 |
| DNA57700-1408 | 203583 | Jan. 12, 1999 |

-continued

| Material | ATCC Dep. No. | Deposit Date |
|---|---|---|
| DNA68818-2536 | 203657 | Feb. 9, 1999 |
| DNA59847-2510 | 203576 | Jan. 12, 1999 |
| DNA76400-2528 | 203573 | Jan. 12, 1999 |
| DNA77624-2515 | 203553 | Dec. 22, 1998 |
| DNA77631-2537 | 203651 | Feb. 9, 1999 |
| DNA82307-2531 | 203537 | Dec. 15, 1998 |

These deposit were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid comprising:

(a) a nucleic acid sequence encoding the polypeptide of SEQ ID NO:7;
(b) the nucleic acid sequence of SEQ ID NO:6;
(c) the full-length coding sequence of the nucleic acid sequence of SEQ ID NO:6; or
(d) the full-length coding sequence of the cDNA deposited under ATCC accession number 203661.

2. The isolated nucleic acid of claim 1 comprising a nucleic acid sequence encoding the polypeptide of SEQ ID NO:7.

3. The isolated nucleic acid of claim 1 comprising the nucleic acid sequence of SEQ ID NO:6.

4. The isolated nucleic acid of claim 1 comprising the full-length coding sequence of the nucleic acid sequence of SEQ ID NO:6.

5. The isolated nucleic acid of claim 1 comprising the full-length coding sequence of the cDNA deposited under ATCC accession number 203661.

* * * * *

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Title Page item [75] Col. 1 (Inventors), Lines 1-6, Delete "David Botstein, Belmont, CA (US); Luc Desnoyers, San Francisco, CA (US); Napoleone Ferrara, San Francisco, CA (US); Sherman Fong, Alameda, CA (US); Wei-Qiang Gao, Foster City, CA (US);".

Title Page Col. 1 (Inventors), Line 9, Delete "James Pan, Belmont, CA (US);".

Title Page Col. 1 (Inventors), Lines 11-14, Delete "Timothy A. Stewart, San Francisco, CA (US); Daniel Tumas, Orinda, CA (US); Colin K. Watanabe, Moraga, CA (US);".

Title Page Col. 2 (Other Publications), Line 4, Delete "Aldimaru" and insert -- Akimaru --, therefor.

Title Page Col. 2 (Other Publications), Line 5, Delete "cubilus" and insert -- cubitus --, therefor.

Title Page Col. 2 (Other Publications), Line 8, Delete "pulative" and insert -- putative --, therefor.

Title Page Col. 2 (Other Publications), Line 12, Delete "cubilus" and insert -- cubitus --, therefor.

Title Page Col. 2 (Other Publications), Line 16, Delete "Intestine" and insert -- intestine --, therefor.

Title Page Col. 2 (Other Publications), Line 21, Delete "Bigood" and insert -- Bitgood --, therefor.

Page 2 Col. 1 (Other Publications), Line 11, Delete "Echeland" and insert -- Echelard --, therefor.

Page 2 Col. 1 (Other Publications), Line 16, Delete "747-758." and insert -- 747-756. --, therefor.

Page 2 Col. 1 (Other Publications), Line 19, Delete "sciarolome" and insert -- sclerotome --, therefor.

Page 2 Col. 1 (Other Publications), Line 20, Delete "79:1176" and insert -- 79:1175 --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Page 2 Col. 1 (Other Publications), Line 24, Delete "Greu" and insert -- Grau --, therefor.

Page 2 Col. 1 (Other Publications), Line 39, Delete "492-496." and insert -- 492-498. --, therefor.

Page 2 Col. 1 (Other Publications), Line 40, Delete "(1996)" and insert -- (1998) --, therefor.

Page 2 Col. 1 (Other Publications), Line 51, Delete "7106-7113." and insert -- 7108-7113. --, therefor.

Page 2 Col. 1 (Other Publications), Line 59, Delete "Fgl-4" and insert -- Fgf-4 --, therefor.

Page 2 Col. 2 (Other Publications), Line 4, Delete "Mango" and insert -- Marigo --, therefor.

Page 2 Col. 2 (Other Publications), Line 5, After "Nature." delete "364:" and insert -- 384: --, therefor.

Page 2 Col. 2 (Other Publications), Line 16, Delete "cubilus-interruptus" and insert -- cubitus interruptus --, therefor.

Page 2 Col. 2 (Other Publications), Line 20, Delete "617-620." and insert -- 517-520. --, therefor.

Page 2 Col. 2 (Other Publications), Line 23, Delete "587-596." and insert -- 587-598. --, therefor.

Page 2 Col. 2 (Other Publications), Line 31, After "in" insert -- a --.

Page 2 Col. 2 (Other Publications), Line 41, Delete "kinasin-related" and insert -- kinesin-related --, therefor.

Page 2 Col. 2 (Other Publications), Line 53, Delete "364:" and insert -- 384: --, therefor.

Page 2 Col. 2 (Other Publications), Line 59, Delete "4224-4226." and insert -- 4224-4228. --, therefor.

UNITED STATES PATENT AND TRADEMARK OFFICE
CERTIFICATE OF CORRECTION

PATENT NO. : 7,101,984 B2  Page 3 of 10
APPLICATION NO. : 10/033167
DATED : September 5, 2006
INVENTOR(S) : Goddard et al.

It is certified that error appears in the above-identified patent and that said Letters Patent is hereby corrected as shown below:

Page 2 Col. 2 (Other Publications), Line 60, Delete "Undan" and insert -- Unden --, therefor.

Page 3 Col. 1 (Other Publications), Line 1, Delete "Hauvel" and insert -- Heuvel --, therefor.

Page 3 Col. 1 (Other Publications), Line 4, Delete "germ-like" and insert -- germ-line --, therefor.

Page 3 Col. 1 (Other Publications), Line 5, Delete "novoid" and insert -- nevoid --, therefor.

Page 3 Col. 1 (Other Publications), Line 8, Delete "80:21-26." and insert -- 60:21-26. --, therefor.

Page 3 Col. 1 (Other Publications), Line 11, Delete "(349,801 seqs, 86," and insert -- (349, 801 seqs, 66, --, therefor.

Page 3 Col. 1 (Other Publications), Line 12, Delete "548.22)," and insert -- 548 aa), --, therefor.

Page 3 Col. 1 (Other Publications), Line 12, Delete "16:12.49" and insert -- 16:12:49 --, therefor.

Page 3 Col. 1 (Other Publications), Line 15, Delete "376. 376." and insert -- 376, --, therefor.

Page 3 Col. 1 (Other Publications), Line 22, After "contain" delete "at" and insert -- a --, therefor.

Page 3 Col. 1 (Other Publications), Lines 22-23, Delete "dionoyl-CoA" and insert -- dienoyl-CoA --, therefor.

Page 3 Col. 1 (Other Publications), Line 57, Delete "Soares$_{13}$ fetal" and insert -- Soares_fetal --, therefor.

Page 3 Col. 2 (Other Publications), Line 3, Delete "cline" and insert -- clone --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Page 3 Col. 2 (Other Publications), Line 13, Delete "element;," and insert -- element; --, therefor.

Page 3 Col. 2 (Other Publications), Line 16, Delete "meningoma" and insert -- meningioma --, therefor.

Page 3 Col. 2 (Other Publications), Line 17, Delete "3 similar" and insert -- 3' similar --, therefor.

Page 3 Col. 2 (Other Publications), Line 18, Delete "element;," and insert -- element; --, therefor.

Page 3 Col. 2 (Other Publications), Line 22, Delete "3, mRNA" and insert -- 3', mRNA --, therefor.

Page 3 Col. 2 (Other Publications), Lines 51-52, Delete "immunohistorchemical" and insert -- immunohistochemical --, therefor.

Page 4 Col. 1 (Other Publications), Line 12, Delete "1988," and insert -- 1998, --, therefor.

Page 4 Col. 1 (Other Publications), Line 12, After "assay" delete "of" and insert -- or --, therefor.

Page 4 Col. 1 (Other Publications), Line 13, Delete "archieve?" and insert -- archive? --, therefor.

Page 4 Col. 1 (Other Publications), Line 18, After "413-417" insert -- . --.

Page 4 Col. 1 (Other Publications), Line 26, Delete "metastatsis" and insert -- metastasis --, therefor.

Page 4 Col. 1 (Other Publications), Line 27, Delete "Metastatsis" and insert -- Metastasis --, therefor.

Page 4 Col. 1 (Other Publications), Line 31, Delete "Myelogeneous" and insert -- Myelogenous --, therefor.

Page 4 Col. 1 (Other Publications), Line 37, Delete "Transaction," and insert -- Transcription, --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Page 4 Col. 1 (Other Publications), Line 39, Delete "Fluerescen" and insert -- Fluorescein --, therefor.

Page 4 Col. 1 (Other Publications), Line 41, Delete "detectin" and insert -- detection --, therefor.

Page 4 Col. 2 (Other Publications), Line 22, Delete "Pollock," and insert -- Pollack, --, therefor.

Page 4 Col. 2 (Other Publications), Line 28, Delete "Pharmaceogenetics," and insert -- Pharmacogenetics, --, therefor.

Page 4 Col. 2 (Other Publications), Line 30, Delete "c-erb-B-2" and insert -- c-erbB-2 --, therefor.

Col. 1, Line 30, Delete "differentiationfactors," and insert -- differentiation factors, --, therefor.

Col. 2, Line 51, Delete "et al." and insert -- et al., --, therefor.

Col. 5, Line 27, Delete "net," and insert -- nel, --, therefor.

Col. 5, Line 29, Delete "net" and insert -- nel --, therefor.

Col. 8, Line 55, Delete "prefereably" and insert -- preferably --, therefor.

Col. 10, Line 61, Delete "prefereably" and insert -- preferably --, therefor.

Col. 13, Line 37, After "(SEQ ID NO:9)" insert -- . --.

Col. 15, Line 15, Delete "prefereably" and insert -- preferably --, therefor.

Col. 17, Line 25, Delete "prefereably" and insert -- preferably --, therefor.

Col. 21, Line 30, Delete "elated" and insert -- related --, therefor.

Col. 22, Line 49, Delete "graft-verus" and insert -- graft-virus --, therefor.

Col. 24, Line 25, Delete "prefereably" and insert -- preferably --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Col. 30, Line 23, After "carrier" insert -- . --.

Col. 35, Line 15, Delete "SEQ ID NO:16" and insert -- SEQ ID NO:15 --, therefor.

Col. 35, Line 21, Delete "SEQ ID NO:18" and insert -- SEQ ID NO:17 --, therefor.

Col. 36, Line 34, Delete "comtemplated" and insert -- contemplated --, therefor.

Col. 38, Line 27, After "2 and 3" delete "5".

Col. 41, Line 11, Delete "460480" and insert -- 460-480 --, therefor.

Col. 45, Line 29, Delete "μIntermittent"" and insert -- "Intermittent" --, therefor.

Col. 47, Line 22 (Table 1), Delete "-3 ," and insert -- -3, --, therefor.

Col. 47, Line 22 (Table 1), After "-2}" insert -- , --.

Col. 57, Line 34 (Table 1- continued), After "siz1--" insert -- ; --.

Col. 57, Line 41 (Table 1- continued), Delete "if (nl++" and insert -- if (n1++ --, therefor.

Col. 57, Line 42 (Table 1- continued), Delete "n[il++];" and insert -- n[i1++]; --, therefor.

Col. 57, Line 63 (Table 1- continued), Delete ""% s","  and insert -- "%s", --, therefor.

Col. 59, Line 26 (Table 1- continued), Delete "< 2++)" and insert -- < 2; i++) --, therefor.

Col. 61, Line 46 (Table 1- continued), Delete "== '-');" and insert -- == '-') --, therefor.

Col. 63, Line 23 (Table 1- continued), Delete "*(p0[0])" and insert -- *(po[0]) --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Col. 67, Line 32 (Table 1- continued), Delete "n[il]" and insert -- n[i1] --, therefor.

Col. 67, Line 36 (Table 1- continued), Delete "x[il]" and insert -- x[i1] --, therefor.

Col. 67, Line 41 (Table 1- continued), Delete "il++;" and insert -- i1 ++; --, therefor.

Col. 69, Line 12 (Table 1- continued), Delete ""w")" and insert -- "w")) --, therefor.

Col. 71, Line 14, After "Polypeptides" delete "Using" and insert the same on line 15 before "WU-BLAST2".

Col. 72, Line 63, Delete "Gin" and insert -- Gln --, therefor.

Col. 73, Line 17, Delete "functionor" and insert -- function or --, therefor.

Col. 73, Lines 34-36, Delete "Such substituted.................sites." and insert the same on line 33 as a continuation of paragraph.

Col. 74, Line 18, Delete "Properties." and insert -- Properties, --, therefor.

Col. 75, Line 30, Delete "USA." and insert -- USA, --, therefor.

Col. 77, Line 24, Delete "K5772" and insert -- K5 772 --, therefor.

Col. 77, Line 43, Delete "tona" and insert -- tonA --, therefor.

Col. 78, Line 8, Delete "Tilbum" and insert -- Tilburn --, therefor.

Col. 79, Line 55, After "Reg." insert -- , --.

Col. 81, Line 24, After "Enzymology" insert -- , --.

Col. 85, Line 16, Delete "-4429–4432" and insert -- 4429–4432 --, therefor.

Col. 88, Line 42, After "Immun." insert -- , --.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Col. 89, Line 62, Delete "469471" and insert -- 469-471 --, therefor.

Col. 91, Line 23, After "Biochem." insert -- , --.

Col. 91, Line 54, After "supra" insert -- ] --.

Col. 93, Line 13, After "Immunol. 13" insert -- , --.

Col. 95, Line 7, After "infection" insert -- [ --.

Col. 95, Line 8, Delete "EP 030891." and insert -- EP 030891]. --, therefor.

Col. 95, Line 33, Delete "Design." and insert -- Design, --, therefor.

Col. 95, Line 42, Delete "generationof" and insert -- generation of --, therefor.

Col. 96, Line 18, Delete "Natl" and insert -- Natl. --, therefor.

Col. 96, Line 33, Delete "Inst." and insert -- Inst., --, therefor.

Col. 97, Line 15, Delete "y" and insert -- $\gamma$ --, therefor.

Col. 99, Line 41, Delete "debydrogenase" and insert -- dehydrogenase --, therefor.

Col. 101, Line 29, Delete "perfoemed" and insert -- performed --, therefor.

Col. 102, Line 27, Delete "Example I" and insert -- Example 1 --, therefor.

Col. 102, Line 44, After "sequence" insert -- : --.

Col. 103, Line 8, Delete "Dec" and insert -- Dec. --, therefor.

Col. 104, Line 47, Delete "Example I" and insert -- Example 1 --, therefor.

Col. 104, Line 64, After "sequence" insert -- : --.

Col. 105, Line 44, Delete "460480" and insert -- 460-480 --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Col. 106, Line 44, Delete "a the" and insert -- the --, therefor.

Col. 107, Line 5, Delete "481484," and insert -- 481-484, --, therefor.

Col. 108, Line 37, Delete "no 3327089," and insert -- no. 3327089, --, therefor.

Col. 108, Lines 59-60, Delete "IBDVORF_2." and insert -- IBDVORF_2, --, therefor.

Col. 109, Line 35, Delete "465469;" and insert -- 465-469; --, therefor.

Col. 109, Line 64, Delete "Insitutes" and insert -- Institutes --, therefor.

Col. 111, Line 10, Delete "positve," and insert -- positive, --, therefor.

Col. 115, Line 5, Delete "ddH2O" and insert -- ddH$_2$O --, therefor.

Col. 116, Line 59, Delete "Taqman™" and insert -- TaqMan™ --, therefor.

Col. 118, Line 59, Delete "cuture" and insert -- culture --, therefor.

Col. 119, Line 55, Delete "RPM11640." and insert -- RPMI1640. --, therefor.

Col. 119, Line 59, Delete "cuture" and insert -- culture --, therefor.

Col. 121, Line 4, Delete "100 µl ." and insert -- 100 µl. --, therefor.

Col. 122, Line 12, Delete "Gene 2.95" and insert -- Gene, 2:95 --, therefor.

Col. 122, Line 51, Delete "Ion" and insert -- lon --, therefor.

Col. 122, Line 53, Delete "O.D.600of" and insert -- O.D.600 of --, therefor.

Col. 122, Line 56, Delete "citrate.2H2O," and insert -- citrate•2H$_2$O, --, therefor.

Col. 125, Line 16, Delete "(1996)," and insert -- (1996)), --, therefor.

UNITED STATES PATENT AND TRADEMARK OFFICE
CERTIFICATE OF CORRECTION

PATENT NO. : 7,101,984 B2
APPLICATION NO. : 10/033167
DATED : September 5, 2006
INVENTOR(S) : Goddard et al.

It is certified that error appears in the above-identified patent and that said Letters Patent is hereby corrected as shown below:

Col. 125, Line 44, Delete "3 L" and insert -- 3L --, therefor.

Col. 125, Line 46, Delete "ie" and insert -- is --, therefor.

Col. 126, Line 53, Delete "Baculovirus-infected" and insert -- Baculovirus-Infected --, therefor.

Col. 129, Line 38, Delete "(I)" and insert -- (i) --, therefor.

Col. 130, Line 32, Delete "Biochemistry." and insert -- Biochemistry, --, therefor.

Col. 185, Line 2, In Claim 1, after "acid" insert -- molecule --.

Col. 186, Line 1, In Claim 2, after "acid" insert -- molecule --.

Col. 186, Line 4, In Claim 3, after "acid" insert -- molecule --.

Col. 186, Line 6, In Claim 4, after "acid" insert -- molecule --.

Col. 186, Line 8, In Claim 5, after "acid" insert -- molecule --.

Signed and Sealed this

First Day of December, 2009

David J. Kappos
*Director of the United States Patent and Trademark Office*

SEQUENCE LISTING

```
<160> NUMBER OF SEQ ID NOS: 38

<210> SEQ ID NO 1
<211> LENGTH: 1283
<212> TYPE: DNA
<213> ORGANISM: Homo sapiens

<400> SEQUENCE: 1
cggacgcgtg ggacccatac ttgctggtct gatccatgca caaggcgggg         50
ctgctaggcc tctgtgcccg ggcttggaat tcggtgcgga tggccagctc        100
cgggatgacc cgccgggacc cgctcgcaaa taaggtggcc ctggtaacgg        150
cctccaccga cgggatcggc ttcgccatcg cccggcgttt ggcccaggac        200
ggggcccatg tggtcgtcag cagccggaag cagcagaatg tggaccaggc        250
ggtggccacg ctgcagggg aggggctgag cgtgacgggc accgtgtgcc         300
atgtggggaa ggcggaggac cgggagcggc tggtggccac ggctgtgaag        350
cttcatggag gtatcgatat cctagtctcc aatgctgctg tcaaccnttt         400
ctttggaagc ataatggatg tcactgagga ggtgtgggac aagactctgg        450
acattaatgt gaaggcccca gccctgatga caaaggcagt ggtgccagaa        500
atggagaaac gaggaggcgg ctcagtggtg atcgtgtctt ccatagcagc        550
cttcagtcca tctcctggct tcagtcctta caatgtcagt aaaacagcct        600
tgctgggcct gaccaagacc ctggccatag agctggcccc aaggaacatt        650
agggtgaact gcctagcacc tggacttatc aagactagct tcagcaggat        700
gctctggatg gacaaggaaa aagaggaaag catgaaagaa accctgcgga        750
taagaaggtt aggcgagcca gaggattgtg ctggcatcgt gtctttcctg        800
tgctctgaag atgccagcta catcactggg gaaacagtgg tggtgggtgg        850
```

```
aggaacccg    tcccgcctct    gaggaccggg    agacagccca    caggccagag            900
ttgggctcta    gctcctggtg    ctgttcctgc    attcacccac    tggccttttcc          950 cacctctgct    caccttactg    ttcacctcat    caaatcagtt    ctgccctgtg          1000
aaaagatcca    gccttccctg    ccgtcaaggt    ggcgtcttac    tcgggattcc          1050
tgctgttgtt    gtggccttgg    gtaaaggcct    ccctgagaa     cacaggacag         1100 gcctgctgac    aaggctgagt    ctaccttggc    aaagaccaag    atattttttc         1150
ctgggccact    ggtgaatctg    aggggtgatg    ggagagaagg    aacctggagt         1200
ggaaggagca    gagttgcaaa    ttaacagctt    gcaaatgagg    tgcaaataaa         1250
atgcagatga    ttgcgcggct    ttgaaaaaaa    aaa                              1283
```

<210> SEQ ID NO 2
<211> LENGTH: 278
<212> TYPE: PRT
<213> ORGANISM: Homo sapiens

<400> SEQUENCE: 2

```
Met His Lys Ala Gly Leu Leu Gly Leu Cys Ala Arg Ala Trp Asn
  1               5                  10                  15

Ser Val Arg Met Ala Ser Ser Gly Met Thr Arg Arg Asp Pro Leu
                 20                  25                  30

Ala Asn Lys Val Ala Leu Val Thr Ala Ser Thr Asp Gly Ile Gly
                 35                  40                  45

Phe Ala Ile Ala Arg Arg Leu Ala Gln Asp Gly Ala His Val Val
                 50                  55                  60

Val Ser Ser Arg Lys Gln Gln Asn Val Asp Gln Ala Val Ala Thr
                 65                  70                  75

Leu Gln Gly Glu Gly Leu Ser Val Thr Gly Thr Val Cys His Val
                 80                  85                  90

Gly Lys Ala Glu Asp Arg Glu Arg Leu Val Ala Thr Ala Val Lys
                 95                 100                 105

Leu His Gly Gly Ile Asp Ile Leu Val Ser Asn Ala Ala Val Asn
                110                 115                 120

Pro Phe Phe Gly Ser Ile Met Asp Val Thr Glu Glu Val Trp Asp
                125                 130                 135

Lys Thr Leu Asp Ile Asn Val Lys Ala Pro Ala Leu Met Thr Lys
                140                 145                 150

Ala Val Val Pro Glu Met Glu Lys Arg Gly Gly Ser Val Val
                155                 160                 165

Ile Val Ser Ser Ile Ala Ala Phe Ser Pro Ser Pro Gly Phe Ser
                170                 175                 180

Pro Tyr Asn Val Ser Lys Thr Ala Leu Leu Gly Leu Thr Lys Thr
                185                 190                 195

Leu Ala Ile Glu Leu Ala Pro Arg Asn Ile Arg Val Asn Cys Leu
                200                 205                 210

Ala Pro Gly Leu Ile Lys Thr Ser Phe Ser Arg Met Leu Trp Met
                215                 220                 225

Asp Lys Glu Lys Glu Glu Ser Met Lys Glu Thr Leu Arg Ile Arg
                230                 235                 240

Arg Leu Gly Glu Pro Glu Asp Cys Ala Gly Ile Val Ser Phe Leu
                245                 250                 255

Cys Ser Glu Asp Ala Ser Tyr Ile Thr Gly Glu Thr Val Val Val
```

```
                    260                 265                 270
Gly Gly Gly Thr Pro Ser Arg Leu
                275

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 3
gcataatgga tgtcactgag g                                              21

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 4
agaacaatcc tgctgaaagc tag                                            23

<210> SEQ ID NO 5
<211> LENGTH: 46
<212> TYPE: DNA
<213> ORGANISM: Artificial Sequence
<220> FEATURE:
<223> OTHER INFORMATION: Synthetic Oligonucleotide Probe

<400> SEQUENCE: 5
gaaacgagga ggcggctcag tggtgatcgt gtcttccata gcagcc                   46

<210> SEQ ID NO 6
<211> LENGTH: 3121
<212> TYPE: DNA
<213> ORGANISM: Homo sapiens

<400> SEQUENCE: 6
gcgccctgag ctccgcctcc gggcccgata gcggcatcga gagcgcctcc               50
gtcgaggacc aggcggcgca gggggccggc gggcgaaagg aggatgaggg              100
ggcgcagcag ctgctgaccc tgcagaacca ggtggcgcgg ctggaggagg              150
agaaccgaga ctttctggct gcgctggagg acgccatgga gcagtacaaa              200
ctgcagagcg accggctgcg tgagcagcag gaggagatgg tggaactgcg              250
gctgcggtta gagctggtgc ggccaggctg gggggcctg cggctcctga               300 atggcctgcc tcccgggtcc tttgtgcctc gacctcatac agccccctg                350 gggggtgccc acgccatgt gctgggcatg gtgccgcctg cctgcctccc                400
tggagatgaa gttggctctg agcagagggg agagcaggtg acaaatggca              450
gggaggctgg agctgagttg ctgactgagg tgaacaggct gggaagtggc              500
tcttcagctg cttcagagga ggaagaggag gaggaggagc cgcccaggcg              550
gaccttacac ctgcgcagaa ataggatcag caactgcagt cagagggcgg              600
gggcacgccc agggagtctg ccagagagga agggcccaga gctttgcctt              650
gaggagttgg atgcagccat tccagggtcc agagcagttg gtgggagcaa              700
ggcccgagtt caggcccgcc aggtcccccc tgccacagcc tcagagtggc              750
```

|  |  |  |  | |
|---|---|---|---|---|
| ggctggccca | ggcccagcag | aagatccggg | agctggctat | caacatccgc | 800 |
| atgaaggagg | agcttattgg | cgagctggtc | cgcacaggaa | aggcagctca | 850 |
| ggccctgaac | cgccagcaca | gccagcgtat | ccgggagctg | gagcaggagg | 900 |
| cagagcaggt | gcgggccgag | ctgagtgaag | gccagaggca | gctgcgggag | 950 |
| ctcgagggca | aggagctcca | ggatgctggc | gagcggtctc | ggctccagga | 1000 |
| gttccgcagg | agggtcgctg | cggcccagag | ccaggtgcag | gtgctgaagg | 1050 |
| agaagaagca | ggctacggag | cggctggtgt | cactgtcggc | ccagagtgag | 1100 |
| aagcgactgc | aggagctcga | gcggaacgtg | cagctcatgc | ggcagcagca | 1150 |
| gggacagctg | cagaggcggc | ttcgcgagga | gacggagcag | aagcggcgcc | 1200 |
| tggaggcaga | aatgagcaag | cggcagcacc | gcgtcaagga | gctggagctg | 1250 |
| aagcatgagc | aacagcagaa | gatcctgaag | attaagacgg | aagagatcgc | 1300 |
| ggccttccag | aggaagaggc | gcagtggcag | caacggctct | gtggtcagcc | 1350 |
| tggaacagca | gcagaagatt | gaggagcaga | agaagtggct | ggaccaggag | 1400 |
| atggagaagt | gctacagca | gcggcgggcg | ctggaggagc | tgggggagga | 1450 |
| gctccacaag | cgggaggcca | tcctggccaa | gaaggaggcc | ctgatgcagg | 1500 |
| agaagacggg | gctggagagc | aagcgcctga | gatccagcca | ggccctcaac | 1550 |
| gaggacatcg | tgcgagtgtc | cagccggctg | gagcacctgg | agaaggagct | 1600 |
| gtccgagaag | agcgggcagc | tgcggcaggg | cagcgcccag | agccagcagc | 1650 |
| agatccgcgg | ggagatcgac | agcctgcgcc | aggagaagga | ctcgctgctc | 1700 |
| aagcagcgcc | tggagatcga | cggcaagctg | aggcagggga | gtctgctgtc | 1750 |
| cccccgaggag | gagcggacgc | tgttccagtt | ggatgaggcc | atcgaggccc | 1800 |
| tggatgctgc | cattgagtat | aagaatgagg | ccatcacatg | ccgccagcgg | 1850 |
| gtgcttcggg | cctcagcctc | gttgctgtcc | cagtgcgaga | tgaacctcat | 1900 |
| ggccaagctc | agctacctct | catcctcaga | gaccagagcc | ctcctctgca | 1950 |
| agtattttga | caaggtggtg | acgctccgag | aggagcagca | ccagcagcag | 2000 |
| attgccttct | cggaactgga | gatgcagctg | gaggagcagc | agaggctggt | 2050 |
| gtactggctg | gaggtggccc | tggagcggca | gcgcctggag | atggaccgcc | 2100 |
| agctgaccct | gcagcagaag | gagcacgagc | agaacatgca | gctgctcctg | 2150 |
| cagcagagtc | gagaccacct | cggtgaaggg | ttagcagaca | gcaggaggca | 2200 |
| gtatgaggcc | cggattcaag | ctctggagaa | ggaactgggc | cgttacatgt | 2250 |
| ggataaacca | ggaactgaaa | cagaagctcg | gcggtgtgaa | cgctgtaggc | 2300 |
| cacagcaggg | gtggggagaa | gaggagcctg | tgctcggagg | gcagacaggc | 2350 |
| tcctggaaat | gaagatgagc | tccacctggc | acccgagctt | ctctggctgt | 2400 |
| cccccctcac | tgagggggcc | ccccgcaccc | gggaggagac | gcgggacttg | 2450 |
| gtccacgctc | cgttaccctt | gacctggaaa | cgctcgagcc | tgtgtggtga | 2500 |
| ggagcagggg | tcccccgagg | aactgaggca | gcgggaggcg | gctgagcccc | 2550 |
| tggtggggcg | ggtgcttcct | gtgggtgagg | caggcctgcc | ctggaacttt | 2600 |
| ggcctttgt | ccaagccccg | gcgggaactg | cgacgagcca | gcccgggat | 2650 |
| gattgatgtc | cggaaaaacc | ccctgtaagc | cctcggggca | gacctgcct | 2700 |
| tggagggaga | ctccgagcct | gctgaaaggg | gcagctgcct | gttttgcttc | 2750 |

```
tgtgaagggc agtccttacc gcacaccta aatccaggcc ctcatctgta       2800
ccctcactgg gatcaacaaa tttgggccat ggcccaaaag aactggaccc       2850
tcatttaaca aataatatg caaattccca ccacttactt ccatgaagct        2900
gtggtaccca attgccgcct tgtgtcttgc tcgaatctca ggacaattct       2950
ggtttcaggc gtaaatggat gtgcttgtag ttcaggggtt tggccaagaa       3000
tcatcacgaa agggtcggtg gcaaccaggt tgtggtttaa atggtcttat       3050
gtatataggg gaaactggga gactttagga tcttaaaaaa ccatttaata       3100
aaaaaaaatc tttgaaggga c                                      3121
```

<210> SEQ ID NO 7
<211> LENGTH: 830
<212> TYPE: PRT
<213> ORGANISM: Homo sapiens

<400> SEQUENCE: 7

```
Met Glu Gln Tyr Lys Leu Gln Ser Asp Arg Leu Arg Glu Gln Gln
  1               5                  10                  15

Glu Glu Met Val Glu Leu Arg Leu Arg Leu Glu Leu Val Arg Pro
                 20                  25                  30

Gly Trp Gly Gly Leu Arg Leu Leu Asn Gly Leu Pro Pro Gly Ser
                 35                  40                  45

Phe Val Pro Arg Pro His Thr Ala Pro Leu Gly Gly Ala His Ala
                 50                  55                  60

His Val Leu Gly Met Val Pro Pro Ala Cys Leu Pro Gly Asp Glu
                 65                  70                  75

Val Gly Ser Glu Gln Arg Gly Glu Gln Val Thr Asn Gly Arg Glu
                 80                  85                  90

Ala Gly Ala Glu Leu Leu Thr Glu Val Asn Arg Leu Gly Ser Gly
                 95                 100                 105

Ser Ser Ala Ala Ser Glu Glu Glu Glu Glu Glu Glu Glu Pro Pro
                110                 115                 120

Arg Arg Thr Leu His Leu Arg Arg Asn Arg Ile Ser Asn Cys Ser
                125                 130                 135

Gln Arg Ala Gly Ala Arg Pro Gly Ser Leu Pro Glu Arg Lys Gly
                140                 145                 150

Pro Glu Leu Cys Leu Glu Glu Leu Asp Ala Ala Ile Pro Gly Ser
                155                 160                 165

Arg Ala Val Gly Gly Ser Lys Ala Arg Val Gln Ala Arg Gln Val
                170                 175                 180

Pro Pro Ala Thr Ala Ser Glu Trp Arg Leu Ala Gln Ala Gln Gln
                185                 190                 195

Lys Ile Arg Glu Leu Ala Ile Asn Ile Arg Met Lys Glu Glu Leu
                200                 205                 210

Ile Gly Glu Leu Val Arg Thr Gly Lys Ala Ala Gln Ala Leu Asn
                215                 220                 225

Arg Gln His Ser Gln Arg Ile Arg Glu Leu Glu Gln Glu Ala Glu
                230                 235                 240

Gln Val Arg Ala Glu Leu Ser Glu Gly Gln Arg Gln Leu Arg Glu
                245                 250                 255

Leu Glu Gly Lys Glu Leu Gln Asp Ala Gly Glu Arg Ser Arg Leu
                260                 265                 270
```

-continued

```
Gln Glu Phe Arg Arg Arg Val Ala Ala Ala Gln Ser Gln Val Gln
            275                 280                 285

Val Leu Lys Glu Lys Lys Gln Ala Thr Glu Arg Leu Val Ser Leu
            290                 295                 300

Ser Ala Gln Ser Glu Lys Arg Leu Gln Glu Leu Glu Arg Asn Val
            305                 310                 315

Gln Leu Met Arg Gln Gln Gln Gly Gln Leu Gln Arg Arg Leu Arg
            320                 325                 330

Glu Glu Thr Glu Gln Lys Arg Arg Leu Glu Ala Glu Met Ser Lys
            335                 340                 345

Arg Gln His Arg Val Lys Glu Leu Glu Leu Lys His Glu Gln Gln
            350                 355                 360

Gln Lys Ile Leu Lys Ile Lys Thr Glu Glu Ile Ala Ala Phe Gln
            365                 370                 375

Arg Lys Arg Arg Ser Gly Ser Asn Gly Ser Val Val Ser Leu Glu
            380                 385                 390

Gln Gln Gln Lys Ile Glu Glu Gln Lys Lys Trp Leu Asp Gln Glu
            395                 400                 405

Met Glu Lys Val Leu Gln Gln Arg Arg Ala Leu Glu Glu Leu Gly
            410                 415                 420

Glu Glu Leu His Lys Arg Glu Ala Ile Leu Ala Lys Lys Glu Ala
            425                 430                 435

Leu Met Gln Glu Lys Thr Gly Leu Glu Ser Lys Arg Leu Arg Ser
            440                 445                 450

Ser Gln Ala Leu Asn Glu Asp Ile Val Arg Val Ser Ser Arg Leu
            455                 460                 465

Glu His Leu Glu Lys Glu Leu Ser Glu Lys Ser Gly Gln Leu Arg
            470                 475                 480

Gln Gly Ser Ala Gln Ser Gln Gln Gln Ile Arg Gly Glu Ile Asp
            485                 490                 495

Ser Leu Arg Gln Glu Lys Asp Ser Leu Leu Lys Gln Arg Leu Glu
            500                 505                 510

Ile Asp Gly Lys Leu Arg Gln Gly Ser Leu Leu Ser Pro Glu Glu
            515                 520                 525

Glu Arg Thr Leu Phe Gln Leu Asp Glu Ala Ile Glu Ala Leu Asp
            530                 535                 540

Ala Ala Ile Glu Tyr Lys Asn Glu Ala Ile Thr Cys Arg Gln Arg
            545                 550                 555

Val Leu Arg Ala Ser Ala Ser Leu Leu Ser Gln Cys Glu Met Asn
            560                 565                 570

Leu Met Ala Lys Leu Ser Tyr Leu Ser Ser Glu Thr Arg Ala
            575                 580                 585

Leu Leu Cys Lys Tyr Phe Asp Lys Val Val Thr Leu Arg Glu Glu
            590                 595                 600

Gln His Gln Gln Gln Ile Ala Phe Ser Glu Leu Glu Met Gln Leu
            605                 610                 615

Glu Glu Gln Gln Arg Leu Val Tyr Trp Leu Glu Val Ala Leu Glu
            620                 625                 630

Arg Gln Arg Leu Glu Met Asp Arg Gln Leu Thr Leu Gln Gln Lys
            635                 640                 645

Glu His Glu Gln Asn Met Gln Leu Leu Gln Gln Ser Arg Asp
            650                 655                 660

His Leu Gly Glu Gly Leu Ala Asp Ser Arg Arg Gln Tyr Glu Ala
```

```
                    665                 670                 675
Arg Ile Gln Ala Leu Glu Lys Glu Leu Gly Arg Tyr Met Trp Ile
                680                 685                 690
Asn Gln Glu Leu Lys Gln Lys Leu Gly Gly Val Asn Ala Val Gly
                695                 700                 705
His Ser Arg Gly Gly Glu Lys Arg Ser Leu Cys Ser Glu Gly Arg
                710                 715                 720
Gln Ala Pro Gly Asn Glu Asp Glu Leu His Leu Ala Pro Glu Leu
                725                 730                 735
Leu Trp Leu Ser Pro Leu Thr Glu Gly Ala Pro Arg Thr Arg Glu
                740                 745                 750
Glu Thr Arg Asp Leu Val His Ala Pro Leu Pro Leu Thr Trp Lys
                755                 760                 765
Arg Ser Ser Leu Cys Gly Glu Glu Gln Gly Ser Pro Glu Glu Leu
                770                 775                 780
Arg Gln Arg Glu Ala Ala Glu Pro Leu Val Gly Arg Val Leu Pro
                785                 790                 795
Val Gly Glu Ala Gly Leu Pro Trp Asn Phe Gly Pro Leu Ser Lys
                800                 805                 810
Pro Arg Arg Glu Leu Arg Arg Ala Ser Pro Gly Met Ile Asp Val
                815                 820                 825
Arg Lys Asn Pro Leu
                830
```

<210> SEQ ID NO 8
<211> LENGTH: 662
<212> TYPE: DNA
<213> ORGANISM: Homo sapiens

<400> SEQUENCE: 8

| | |
|---|---|
| attctcctag agcatctttg gaagcatgag gccacgatgc tgcatcttgg | 50 |
| ctcttgtctg ctggataaca gtcttcctcc tccagtgttc aaaaggaact | 100 |
| acagacgctc ctgttggctc aggactgtgg ctgtgccagc cgacacccag | 150 |
| gtgtgggaac aagatctaca acccttcaga gcagtgctgt tatgatgatg | 200 |
| ccatcttatc cttaaaggag acccgccgct gtggctccac ctgcaccttc | 250 |
| tggccctgct ttgagctctg ctgtcccgag tcttttggcc cccagcagaa | 300 |
| gtttcttgtg aagttgaggg ttctgggtat gaagtctcag tgtcacttat | 350 |
| ctcccatctc ccggagctgt accaggaaca ggaggcacgt cctgtaccca | 400 |
| taaaaacccc aggctccact ggcagacggc agacaagggg agaagagacg | 450 |
| aagcagctgg acatcggaga ctacagttga acttcggaga gaagcaactt | 500 |
| gacttcagag ggatggctca atgacatagc tttggagagg agcccagctg | 550 |
| gggatggcca gacttcaggg gaagaatgcc ttcctgcttc atccccttc | 600 |
| cagctcccct tcccgctgag agccactttc atcggcaata aaatccccca | 650 |
| catttaccat ct | 662 |

<210> SEQ ID NO 9
<211> LENGTH: 125
<212> TYPE: PRT
<213> ORGANISM: Homo sapiens

<400> SEQUENCE: 9

```
Met Arg Pro Arg Cys Cys Ile Leu Ala Leu Val Cys Trp Ile Thr
 1               5                  10                  15

Val Phe Leu Leu Gln Cys Ser Lys Gly Thr Thr Asp Ala Pro Val
            20                  25                  30

Gly Ser Gly Leu Trp Leu Cys Gln Pro Thr Pro Arg Cys Gly Asn
            35                  40                  45

Lys Ile Tyr Asn Pro Ser Glu Gln Cys Cys Tyr Asp Asp Ala Ile
            50                  55                  60

Leu Ser Leu Lys Glu Thr Arg Arg Cys Gly Ser Thr Cys Thr Phe
            65                  70                  75

Trp Pro Cys Phe Glu Leu Cys Cys Pro Glu Ser Phe Gly Pro Gln
            80                  85                  90

Gln Lys Phe Leu Val Lys Leu Arg Val Leu Gly Met Lys Ser Gln
            95                 100                 105

Cys His Leu Ser Pro Ile Ser Arg Ser Cys Thr Arg Asn Arg Arg
           110                 115                 120

His Val Leu Tyr Pro
           125

<210> SEQ ID NO 10
<211> LENGTH: 1942
<212> TYPE: DNA
<213> ORGANISM: Homo sapiens

<400> SEQUENCE: 10
cccacgcgtc cgcccacgcg tccgggtgcc actcgcgcgc cggccgcgct        50
ccgggcttct cttttccctc cgacgcgcca cggctgccca gacattccgg       100
ctgccgggtc tggagagctc cccgaacccc tccgcggaga ggagcgaggc       150
ggcgccaggg tggccccggg ggcgcgcttg gtctcggaga agcggggacg       200
aggccggagg atgagcgact gagggcgacg cgggcactga cgcgagttgg       250
ggccgcgact accggcagct gacagcgcga tgagcgactc cccagagacg       300
ccctagcccg gtgtgcgcgc caggcggagc gcgcaggtgg ggctgggctg       350
ttagtggtcc gccccacgcg ggtcgccggc cggcccagga tgggcgctgg       400
caacccgggc ccgcgcccgc cgctgctacc cctgcgcccg ctgcgagccc       450
ggcgtccggc ccgcgccctg cgctcatgga cggcggctcc cggctggcgg       500
cggcgcgccc ccgggctgtg aatgcgactc gcccctcggc cgcgctcccc       550
gcccgcccgc ccgccgggac gtggtagggg atgcccagct ccactgcgat       600
ggcagttggc gcgctctcca gttccctcct ggtcacctgc tgcctgatgg       650
tggctctgtg cagtccgagc atcccgctgg agaagctggc ccaggcacca       700
gagcagccgg gccaggagaa gcgtgagcac gccactcggg acggcccggg       750
gcgggtgaac gagctcgggc gcccggcgag ggacgagggc ggcagcggcc       800
gggactggaa gagcaagagc ggccgtgggc tcgccggccg tgagccgtgg       850
agcaagctga agcaggcctg ggtctcccag ggcgggggcg ccaaggccgg       900
ggatctgcag gtccggcccc gcggggacac ccgcaggcg gaagccctgg        950 ccgcagccgc ccaggacgcg attggcccgg aactcgcgcc cacgcccgag      1000
ccacccgagg agtacgtgta cccggactac cgtggcaagg gctgcgtgga      1050
cgagagcggc ttcgtgtacg cgatcgggga gaagttcgcg ccgggcccct      1100
```

-continued

| | |
|---|---|
| cggcctgccc gtgcctgtgc accgaggagg ggccgctgtg cgcgcagccc | 1150 |
| gagtgcccga ggctgcaccc gcgctgcatc cacgtcgaca cgagccagtg | 1200 |
| ctgcccgcag tgcaaggaga ggaagaacta ctgcgagttc cggggcaaga | 1250 |
| cctatcagac tttggaggag ttcgtggtgt ctccatgcga gaggtgtcgc | 1300 |
| tgtgaagcca acggtgaggt gctatgcaca gtgtcagcgt gtccccagac | 1350 |
| ggagtgtgtg gaccctgtgt acgagcctga tcagtgctgt cccatctgca | 1400 |
| aaaatggtcc aaactgcttt gcagaaaccg cggtgatccc tgctggcaga | 1450 |
| gaagtgaaga ctgacgagtg caccatatgc cactgtactt atgaggaagg | 1500 |
| cacatggaga atcgagcggc aggccatgtg cacgagacat gaatgcaggc | 1550 |
| aaatgtagac gcttcccaga acacaaactc tgacttttc tagaacattt | 1600 |
| tactgatgtg aacattctag atgactctgg gaactatcag tcaaagaaga | 1650 |
| cttttgatga ggaataatgg aaaattgttg gtacttttcc ttttcttgat | 1700 |
| aacagttact acaacagaag gaaatggata tatttcaaaa catcaacaag | 1750 |
| aactttgggc ataaaatcct tctctaaata aatgtgctat tttcacagta | 1800 |
| agtacacaaa agtacactat tatatatcaa atgtatttct ataatccctc | 1850 |
| cattagagag cttatataag tgttttctat agatgcagat taaaaatgct | 1900 |
| gtgttgtcaa ccgtcaaaaa aaaaaaaaaa aaaaaaaaa aa | 1942 |

```
<210> SEQ ID NO 11
<211> LENGTH: 325
<212> TYPE: PRT
<213> ORGANISM: Homo sapiens

<400> SEQUENCE: 11

Met Pro Ser Ser Thr Ala Met Ala Val Gly Ala Leu Ser Ser
  1               5                  10                  15

Leu Leu Val Thr Cys Cys Leu Met Val Ala Leu Cys Ser Pro Ser
                 20                  25                  30

Ile Pro Leu Glu Lys Leu Ala Gln Ala Pro Glu Gln Pro Gly Gln
             35                  40                  45

Glu Lys Arg Glu His Ala Thr Arg Asp Gly Pro Gly Arg Val Asn
             50                  55                  60

Glu Leu Gly Arg Pro Ala Arg Asp Glu Gly Ser Gly Arg Asp
         65                  70                  75

Trp Lys Ser Lys Ser Gly Arg Gly Leu Ala Gly Arg Glu Pro Trp
             80                  85                  90

Ser Lys Leu Lys Gln Ala Trp Val Ser Gln Gly Gly Ala Lys
             95                 100                 105

Ala Gly Asp Leu Gln Val Arg Pro Arg Gly Asp Thr Pro Gln Ala
            110                 115                 120

Glu Ala Leu Ala Ala Ala Gln Asp Ala Ile Gly Pro Glu Leu
            125                 130                 135

Ala Pro Thr Pro Glu Pro Pro Glu Glu Tyr Val Tyr Pro Asp Tyr
            140                 145                 150

Arg Gly Lys Gly Cys Val Asp Glu Ser Gly Phe Val Tyr Ala Ile
            155                 160                 165

Gly Glu Lys Phe Ala Pro Gly Pro Ser Ala Cys Pro Cys Leu Cys
            170                 175                 180

Thr Glu Glu Gly Pro Leu Cys Ala Gln Pro Glu Cys Pro Arg Leu
```

```
                        185                 190                 195
His Pro Arg Cys Ile His Val Asp Thr Ser Gln Cys Cys Pro Gln
                200                 205                 210
Cys Lys Glu Arg Lys Asn Tyr Cys Glu Phe Arg Gly Lys Thr Tyr
                215                 220                 225
Gln Thr Leu Glu Glu Phe Val Val Ser Pro Cys Glu Arg Cys Arg
                230                 235                 240
Cys Glu Ala Asn Gly Glu Val Leu Cys Thr Val Ser Ala Cys Pro
                245                 250                 255
Gln Thr Glu Cys Val Asp Pro Val Tyr Glu Pro Asp Gln Cys Cys
                260                 265                 270
Pro Ile Cys Lys Asn Gly Pro Asn Cys Phe Ala Glu Thr Ala Val
                275                 280                 285
Ile Pro Ala Gly Arg Glu Val Lys Thr Asp Glu Cys Thr Ile Cys
                290                 295                 300
His Cys Thr Tyr Glu Glu Gly Thr Trp Arg Ile Glu Arg Gln Ala
                305                 310                 315
Met Cys Thr Arg His Glu Cys Arg Gln Met
                320                 325

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 12
gaggtgtcgc tgtgaagcca acgg                                            24

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 13
cgctcgattc tccatgtgcc ttcc                                            24

<210> SEQ ID NO 14
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 14
gacggagtgt gtggaccctg tgtacgagcc tgatcagtgc tgtcc                     45

<210> SEQ ID NO 15
<211> LENGTH: 1587
<212> TYPE: DNA
<213> ORGANISM: Homo sapiens

<400> SEQUENCE: 15
cagccacaga cgggtcatga gcgcggtatt actgctggcc ctcctggggt                50
tcatcctccc actgccagga gtgcaggcgc tgctctgcca gtttgggaca              100
gttcagcatg tgtggaaggt gtccgaccta ccccggcaat ggacccctaa              150
```

-continued

| | |
|---|---|
| gaacaccagc tgcgacagcg gcttggggtg ccaggacacg ttgatgctca | 200 |
| ttgagagcgg accccaagtg agcctggtgc tctccaaggg ctgcacggag | 250 |
| gccaaggacc aggagccccg cgtcactgag caccggatgg gccccggcct | 300 |
| ctccctgatc tcctacacct tcgtgtgccg ccaggaggac ttctgcaaca | 350 |
| acctcgttaa ctccctcccg ctttgggccc cacagccccc agcagaccca | 400 |
| ggatccttga ggtgcccagt ctgcttgtct atggaaggct gtctggaggg | 450 |
| gacaacagaa gagatctgcc ccaagggac cacacactgt tatgatggcc | 500 |
| tcctcaggct caggggagga ggcatcttct ccaatctgag agtccaggga | 550 |
| tgcatgcccc agccaggttg caacctgctc aatgggacac aggaaattgg | 600 |
| gcccgtgggt atgactgaga actgcaatag gaaagatttt ctgacctgtc | 650 |
| atcgggggac caccattatg acacacggaa acttggctca agaacccact | 700 |
| gattggacca catcgaatac cgagatgtgc gaggtgggc aggtgtgtca | 750 |
| ggagacgctg ctgctcatag atgtaggact cacatcaacc ctggtgggga | 800 |
| caaaaggctg cagcactgtt ggggctcaaa attcccagaa gaccaccatc | 850 |
| cactcagccc ctcctggggt gcttgtggcc tcctataccc acttctgctc | 900 |
| ctcggacctg tgcaatagtg ccagcagcag cagcgttctg ctgaactccc | 950 |
| tccctcctca agctgcccct gtcccaggag accggcagtg tcctacctgt | 1000 |
| gtgcagcccc ttggaacctg ttcaagtggc tcccccgaa tgacctgccc | 1050 |
| cagggcgcc actcattgtt atgatgggta cattcatctc tcaggaggtg | 1100 |
| ggctgtccac caaaatgagc attcaggct gcgtggccca accttccagc | 1150 |
| ttcttgttga accacaccag acaaatcggg atcttctctg cgcgtgagaa | 1200 |
| gcgtgatgtg cagcctcctg cctctcagca tgagggaggt ggggctgagg | 1250 |
| gcctggagtc tctcacttgg ggggtggggc tggcactggc cccagcgctg | 1300 |
| tggtggggag tggtttgccc ttcctgctaa ctctattacc cccacgattc | 1350 |
| ttcaccgctg ctgaccaccc acactcaacc tccctctgac ctcataacct | 1400 |
| aatggccttg gacaccagat tctttcccat tctgtccatg aatcatcttc | 1450 |
| cccacacaca atcattcata tctactcacc taacagcaac actggggaga | 1500 |
| gcctggagca tccggacttg ccctatggga gagggacgc tggaggagtg | 1550 |
| gctgcatgta tctgataata cagaccctgt cctttca | 1587 |

<210> SEQ ID NO 16
<211> LENGTH: 437
<212> TYPE: PRT
<213> ORGANISM: Homo sapiens

<400> SEQUENCE: 16

Met Ser Ala Val Leu Leu Ala Leu Leu Gly Phe Ile Leu Pro
1               5                   10                  15

Leu Pro Gly Val Gln Ala Leu Leu Cys Gln Phe Gly Thr Val Gln
                20                  25                  30

His Val Trp Lys Val Ser Asp Leu Pro Arg Gln Trp Thr Pro Lys
                35                  40                  45

Asn Thr Ser Cys Asp Ser Gly Leu Gly Cys Gln Asp Thr Leu Met
                50                  55                  60

Leu Ile Glu Ser Gly Pro Gln Val Ser Leu Val Leu Ser Lys Gly

```
                    65                  70                  75
Cys Thr Glu Ala Lys Asp Gln Glu Pro Arg Val Thr Glu His Arg
                80                  85                  90
Met Gly Pro Gly Leu Ser Leu Ile Ser Tyr Thr Phe Val Cys Arg
                95                 100                 105
Gln Glu Asp Phe Cys Asn Asn Leu Val Asn Ser Leu Pro Leu Trp
               110                 115                 120
Ala Pro Gln Pro Pro Ala Asp Pro Gly Ser Leu Arg Cys Pro Val
               125                 130                 135
Cys Leu Ser Met Glu Gly Cys Leu Glu Gly Thr Thr Glu Glu Ile
               140                 145                 150
Cys Pro Lys Gly Thr Thr His Cys Tyr Asp Gly Leu Leu Arg Leu
               155                 160                 165
Arg Gly Gly Gly Ile Phe Ser Asn Leu Arg Val Gln Gly Cys Met
               170                 175                 180
Pro Gln Pro Gly Cys Asn Leu Leu Asn Gly Thr Gln Glu Ile Gly
               185                 190                 195
Pro Val Gly Met Thr Glu Asn Cys Asn Arg Lys Asp Phe Leu Thr
               200                 205                 210
Cys His Arg Gly Thr Thr Ile Met Thr His Gly Asn Leu Ala Gln
               215                 220                 225
Glu Pro Thr Asp Trp Thr Thr Ser Asn Thr Glu Met Cys Glu Val
               230                 235                 240
Gly Gln Val Cys Gln Glu Thr Leu Leu Leu Ile Asp Val Gly Leu
               245                 250                 255
Thr Ser Thr Leu Val Gly Thr Lys Gly Cys Ser Thr Val Gly Ala
               260                 265                 270
Gln Asn Ser Gln Lys Thr Thr Ile His Ser Ala Pro Pro Gly Val
               275                 280                 285
Leu Val Ala Ser Tyr Thr His Phe Cys Ser Ser Asp Leu Cys Asn
               290                 295                 300
Ser Ala Ser Ser Ser Val Leu Leu Asn Ser Leu Pro Pro Gln
               305                 310                 315
Ala Ala Pro Val Pro Gly Asp Arg Gln Cys Pro Thr Cys Val Gln
               320                 325                 330
Pro Leu Gly Thr Cys Ser Ser Gly Ser Pro Arg Met Thr Cys Pro
               335                 340                 345
Arg Gly Ala Thr His Cys Tyr Asp Gly Tyr Ile His Leu Ser Gly
               350                 355                 360
Gly Gly Leu Ser Thr Lys Met Ser Ile Gln Gly Cys Val Ala Gln
               365                 370                 375
Pro Ser Ser Phe Leu Leu Asn His Thr Arg Gln Ile Gly Ile Phe
               380                 385                 390
Ser Ala Arg Glu Lys Arg Asp Val Gln Pro Ala Ser Gln His
               395                 400                 405
Glu Gly Gly Gly Ala Glu Gly Leu Glu Ser Leu Thr Trp Gly Val
               410                 415                 420
Gly Leu Ala Leu Ala Pro Ala Leu Trp Trp Gly Val Val Cys Pro
               425                 430                 435
Ser Cys

<210> SEQ ID NO 17
<211> LENGTH: 2387
```

<212> TYPE: DNA
<213> ORGANISM: Homo sapiens

<400> SEQUENCE: 17

| | |
|---|---:|
| cgacgatgct acgcgcgccc ggctgcctcc tccggacctc cgtagcgcct | 50 |
| gccgcggccc tggctgcggc gctgctctcg tcgcttgcgc gctgctctct | 100 |
| tctagagccg agggacccgg tggcctcgtc gctcagcccc tatttcggca | 150 |
| ccaagactcg ctacgaggat gtcaaccccg tgctattgtc gggccccgag | 200 |
| gctccgtggc gggaccctga gctgctgag gggacctgca ccccggtgca | 250 |
| gctggtcgcc ctcattcgcc acggcacccg ctaccccacg gtcaaacaga | 300 |
| tccgcaagct gaggcagctg cacggggttgc tgcaggcccg cgggtccagg | 350 |
| gatggcgggg ctagtagtac cggcagccgc gacctgggtg cagcgctggc | 400 |
| cgactggcct ttgtggtacg cggactggat ggacgggcag ctagtagaga | 450 |
| agggacggca ggatatgcga cagctggcgc tgcgtctggc ctcgctcttc | 500 |
| ccggcccttt tcagccgtga gaactacggc cgcctgcggc tcatcaccag | 550 |
| ttccaagcac cgctgcatgg atagcagcgc cgccttcctg caggggctgt | 600 |
| ggcagcacta ccaccctggc ttgccgccgc cggacgtcgc agatatggag | 650 |
| tttggacctc caacagttaa tgataaacta atgagatttt ttgatcactg | 700 |
| tgagaagttt ttaactgaag tagaaaaaaa tgctacagct ctttatcacg | 750 |
| tggaagcctt caaaactgga ccagaaatgc agaacatttt aaaaaaagtt | 800 |
| gcagctactt tgcaagtgcc agtaaatgat ttaaatgcag atttaattca | 850 |
| agtagccttt tcacctgtt catttgacct ggcaattaaa ggtgttaaat | 900 |
| ctccttggtg tgatgttttt gacatagatg atgcaaaggt attagaatat | 950 |
| ttaaatgatc tgaaacaata ttggaaaaga ggatatgggt atactattaa | 1000 |
| cagtcgatcc agctgcacct tgtttcagga tatctttcag cacttggaca | 1050 |
| aagcagttga acagaaacaa aggtctcagc caatttcttc tccagtcatc | 1100 |
| ctccagtttg gtcatgcaga gactcttctt ccactgcttt ctctcatggg | 1150 |
| ctacttcaaa gacaaggaac ccctaacagc gtacaattac aaaaaaacaaa | 1200 |
| tgcatcggaa gttccgaagt ggtctcattg taccttatgc ctcgaacctg | 1250 |
| atatttgtgc tttaccactg tgaaaatgct aagactccta agaacaattt | 1300 |
| ccgagtgcag atgttattaa atgaaaaggt gttaccttg gcttactcac | 1350 |
| aagaaactgt tcattttat gaagatctga agaaccacta caaggacatc | 1400 |
| cttcagagtt gtcaaaccag tgaagaatgt gaattagcaa gggctaacag | 1450 |
| tacatctgat gaactatgag taactgaaga acatttttaa ttcttttagga | 1500 |
| atctgcaatg agtgattaca tgcttgtaat aggtaggcaa ttccttgatt | 1550 |
| acaggaagct tttatattac ttgagtattt ctgtcttttc acagaaaaac | 1600 |
| attgggtttc tctctgggtt tggacatgaa atgtaagaaa agattttca | 1650 |
| ctggagcagc tctcttaagg agaaacaaat ctatttagag aaacagctgg | 1700 |
| ccctgcaaat gtttacagaa atgaaattct tcctacttat ataagaaatc | 1750 |
| tcacactgag atagaattgt gatttcataa taacacttga aaagtgctgg | 1800 |
| agtaacaaaa tatctcagtt ggaccatcct taacttgatt gaactgtcta | 1850 |

|  |  |
|---|---|
| ggaactttac agattgttct gcagttctct cttcttttcc tcaggtagga | 1900 |
| cagctctagc attttcttaa tcaggaatat tgtggtaagc tgggagtatc | 1950 |
| actctggaag aaagtaacat ctccagatga gaatttgaaa caagaaacag | 2000 |
| agtgttgtaa aaggacacct tcactgaagc aagtcggaaa gtacaatgaa | 2050 |
| aataaatatt tttggtattt atttatgaaa tatttgaaca ttttttcaat | 2100 |
| aattccttt tacttctagg aagtctcaaa agaccatctt aaattattat | 2150 |
| atgtttggac aattagcaac aagtcagata gttagaatcg aagttttca | 2200 |
| aatccattgc ttagctaact ttttcattct gtcacttggc ttcgattttt | 2250 |
| atattttcct attatatgaa atgtatcttt tggttgtttg attttttcttt | 2300 |
| ctttctttgt aaatagttct gagttctgtc aaatgccgtg aaagtatttg | 2350 |
| ctataataaa gaaaattctt gtgactttaa aaaaaaa | 2387 |

<210> SEQ ID NO 18
<211> LENGTH: 487
<212> TYPE: PRT
<213> ORGANISM: Homo sapiens

<400> SEQUENCE: 18

Met Leu Arg Ala Pro Gly Cys Leu Leu Arg Thr Ser Val Ala Pro
 1               5                  10                  15

Ala Ala Ala Leu Ala Ala Leu Leu Ser Ser Leu Ala Arg Cys
                20                  25                  30

Ser Leu Leu Glu Pro Arg Asp Pro Val Ala Ser Ser Leu Ser Pro
                35                  40                  45

Tyr Phe Gly Thr Lys Thr Arg Tyr Glu Asp Val Asn Pro Val Leu
                50                  55                  60

Leu Ser Gly Pro Glu Ala Pro Trp Arg Asp Pro Glu Leu Leu Glu
                65                  70                  75

Gly Thr Cys Thr Pro Val Gln Leu Val Ala Leu Ile Arg His Gly
                80                  85                  90

Thr Arg Tyr Pro Thr Val Lys Gln Ile Arg Lys Leu Arg Gln Leu
                95                 100                 105

His Gly Leu Leu Gln Ala Arg Gly Ser Arg Asp Gly Gly Ala Ser
               110                 115                 120

Ser Thr Gly Ser Arg Asp Leu Gly Ala Ala Leu Ala Asp Trp Pro
               125                 130                 135

Leu Trp Tyr Ala Asp Trp Met Asp Gly Gln Leu Val Glu Lys Gly
               140                 145                 150

Arg Gln Asp Met Arg Gln Leu Ala Leu Arg Leu Ala Ser Leu Phe
               155                 160                 165

Pro Ala Leu Phe Ser Arg Glu Asn Tyr Gly Arg Leu Arg Leu Ile
               170                 175                 180

Thr Ser Ser Lys His Arg Cys Met Asp Ser Ser Ala Ala Phe Leu
               185                 190                 195

Gln Gly Leu Trp Gln His Tyr His Pro Gly Leu Pro Pro Pro Asp
               200                 205                 210

Val Ala Asp Met Glu Phe Gly Pro Pro Thr Val Asn Asp Lys Leu
               215                 220                 225

Met Arg Phe Phe Asp His Cys Glu Lys Phe Leu Thr Glu Val Glu
               230                 235                 240

Lys Asn Ala Thr Ala Leu Tyr His Val Glu Ala Phe Lys Thr Gly

-continued

```
                    245                 250                 255
Pro Glu Met Gln Asn Ile Leu Lys Lys Val Ala Ala Thr Leu Gln
                260                 265                 270
Val Pro Val Asn Asp Leu Asn Ala Asp Leu Ile Gln Val Ala Phe
            275                 280                 285
Phe Thr Cys Ser Phe Asp Leu Ala Ile Lys Gly Val Lys Ser Pro
        290                 295                 300
Trp Cys Asp Val Phe Asp Ile Asp Asp Ala Lys Val Leu Glu Tyr
    305                 310                 315
Leu Asn Asp Leu Lys Gln Tyr Trp Lys Arg Gly Tyr Gly Tyr Thr
320                 325                 330
Ile Asn Ser Arg Ser Ser Cys Thr Leu Phe Gln Asp Ile Phe Gln
            335                 340                 345
His Leu Asp Lys Ala Val Glu Gln Lys Gln Arg Ser Gln Pro Ile
        350                 355                 360
Ser Ser Pro Val Ile Leu Gln Phe Gly His Ala Glu Thr Leu Leu
    365                 370                 375
Pro Leu Leu Ser Leu Met Gly Tyr Phe Lys Asp Lys Glu Pro Leu
380                 385                 390
Thr Ala Tyr Asn Tyr Lys Lys Gln Met His Arg Lys Phe Arg Ser
            395                 400                 405
Gly Leu Ile Val Pro Tyr Ala Ser Asn Leu Ile Phe Val Leu Tyr
        410                 415                 420
His Cys Glu Asn Ala Lys Thr Pro Lys Glu Gln Phe Arg Val Gln
    425                 430                 435
Met Leu Leu Asn Glu Lys Val Leu Pro Leu Ala Tyr Ser Gln Glu
440                 445                 450
Thr Val Ser Phe Tyr Glu Asp Leu Lys Asn His Tyr Lys Asp Ile
            455                 460                 465
Leu Gln Ser Cys Gln Thr Ser Glu Glu Cys Glu Leu Ala Arg Ala
        470                 475                 480
Asn Ser Thr Ser Asp Glu Leu
                485

<210> SEQ ID NO 19
<211> LENGTH: 3554
<212> TYPE: DNA
<213> ORGANISM: Homo sapiens

<400> SEQUENCE: 19
gggactacaa gccgcgccgc gctgccgctg cccctcagc  aaccctcgac          50 atggcgctga ggcggccacc gcgactccgg ctctgcgctc ggctgcctga         100
cttcttcctg ctgctgcttt tcaggggctg cctgataggg gctgtaaatc         150
tcaaatccag caatcgaacc ccagtggtac aggaatttga agtgtggaa          200 ctgtcttgca tcattacgga ttcgcagaca agtgacccca ggatcgagtg         250
gaagaaaatt caagatgaac aaaccacata tgtgtttttt gacaacaaaa         300
ttcagggaga cttggcgggt cgtgcagaaa tactgggaa  gacatccctg         350 aagatctgga atgtgacacg gagagactca gcccttatc  gctgtgaggt         400 cgttgctcga aatgaccgca aggaaattga tgagattgtg atcgagttaa         450
ctgtgcaagt gaagccagtg acccctgtct gtagagtgcc gaaggctgta         500
ccagtaggca agatggcaac actgcactgc caggagagtg agggccaccc         550
```

-continued

| | |
|---|---|
| ccggcctcac tacagctggt atcgcaatga tgtaccactg cccacggatt | 600 |
| ccagagccaa tcccagattt cgcaattctt ctttccactt aaactctgaa | 650 |
| acaggcactt tggtgttcac tgctgttcac aaggacgact ctgggcagta | 700 |
| ctactgcatt gcttccaatg acgcaggctc agccaggtgt gaggagcagg | 750 |
| agatggaagt ctatgacctg aacattggcg gaattattgg ggggttctg | 800 |
| gttgtccttg ctgtactggc cctgatcacg ttgggcatct gctgtgcata | 850 |
| cagacgtggc tacttcatca acaataaaca ggatggagaa agttacaaga | 900 |
| acccagggaa accagatgga gttaactaca tccgcactga cgaggagggc | 950 |
| gacttcagac acaagtcatc gtttgtgatc tgagacccgc ggtgtggctg | 1000 |
| agagcgcaca gagcgcacgt gcacatacct gctagaaa ctcctgtcaa | 1050 |
| ggcagcgaga gctgatgcac tcggacagag ctagacactc attcagaagc | 1100 |
| ttttcgtttt ggccaaagtt gaccactact cttcttactc taacaagcca | 1150 |
| catgaataga agaattttcc tcaagatgga cccggtaaat ataaccacaa | 1200 |
| ggaagcgaaa ctgggtgcgt tcactgagtt gggttcctaa tctgtttctg | 1250 |
| gcctgattcc cgcatgagta ttagggtgat cttaaagagt ttgctcacgt | 1300 |
| aaacgcccgt gctgggccct gtgaagccag catgttcacc actggtcgtt | 1350 |
| cagcagccac gacagcacca tgtgagatgg cgaggtggct ggacagcacc | 1400 |
| agcagcgcat cccggcggga acccagaaaa ggcttcttac acagcagcct | 1450 |
| tacttcatcg gcccacagac accaccgcag tttcttctta aggctctgc | 1500 |
| tgatcggtgt tgcagtgtcc attgtggaga agcttttgg atcagcattt | 1550 |
| tgtaaaaaca accaaaatca ggaaggtaaa ttggttgctg gaagagggat | 1600 |
| cttgcctgag gaaccctgct tgtccaacag ggtgtcagga tttaaggaaa | 1650 |
| accttcgtct taggctaagt ctgaaatggt actgaaatat gcttttctat | 1700 |
| gggtcttgtt tatttatat aatttacat ctaaatttt gctaaggatg | 1750 |
| tattttgatt attgaaaaga aatttctat ttaaactgta aatatattgt | 1800 |
| catacaatgt taaataacct attttttaa aaaagttcaa cttaaggtag | 1850 |
| aagttccaag ctactagtgt taaattggaa aatatcaata attaagagta | 1900 |
| ttttacccaa ggaatcctct catggaagtt tactgtgatg ttcctttct | 1950 |
| cacacaagtt ttagccttt tcacaaggga actcatactg tctacacatc | 2000 |
| agaccatagt tgcttaggaa acctttaaaa attccagtta agcaatgttg | 2050 |
| aaatcagttt gcatctcttc aaaagaaacc tctcaggtta gctttgaact | 2100 |
| gcctcttcct gagatgacta ggacagtctg tacccgagg ccacccgaaa | 2150 |
| gccctcagat gtacatacac agatgccagt cagctcctgg ggttgcgcca | 2200 |
| ggcgccccg ctctagctca ctgttgcctc gctgtctgcc aggaggccct | 2250 |
| gccatccttg ggccctggca gtggctgtgt cccagtgagc tttactcacg | 2300 |
| tggcccttgc ttcatccagc acagctctca ggtgggcact gcaggacac | 2350 |
| tggtgtcttc catgtagcgt cccagctttg ggctcctgta acagacctct | 2400 |
| ttttggttat ggatggctca caaatagg ccccaatgc tatttttt | 2450 |
| ttttaagttt gtttaattat ttgttaagat tgtctaaggc caaaggcaat | 2500 |

-continued

```
tgcgaaatca agtctgtcaa gtacaataac attttaaaa gaaaatggat            2550 cccactgttc ctctttgcca cagagaaagc acccagacgc acaggctct            2600 gtcgcatttc aaaacaaacc atgatggagt ggcggccagt ccagccttt            2650 aaagaacgtc aggtggagca gccaggtgaa aggcctggcg gggaggaaag           2700
tgaaacgcct gaatcaaaag cagttttcta attttgactt taaatttttc           2750
atccgccgga gacactgctc ccatttgtgg ggggacatta gcaacatcac           2800
tcagaagcct gtgttcttca gagcaggtg ttctcagcct cacatgccct            2850
gccgtgctgg actcaggact gaagtgctgt aaagcaagga gctgctgaga           2900
aggagcactc cactgtgtgc ctggagaatg gctctcacta ctcaccttgt           2950
ctttcagctt ccagtgtctt gggtttttta actttgaca gctttttttt            3000 aattgcatac atgagactgt gttgactttt tttagttatg tgaaacactt           3050
tgccgcaggc cgcctggcag aggcaggaaa tgctccagca gtggctcagt           3100
gctccctggt gtctgctgca tggcatcctg gatgcttagc atgcaagttc           3150
cctccatcat tgccaccttg gtagagaggg atggctcccc accctcagcg           3200
ttggggattc acgctccagc ctccttcttg gttgtcatag tgatagggta           3250
gccttattgc cccctcttct tataccctaa aaccttctac actagtgcca           3300
tgggaaccag gtctgaaaaa gtagagagaa gtgaaagtag agtctgggaa           3350
gtagctgcct ataactgaga ctagacgaa aaggaatact cgtgtatttt            3400
aagatatgaa tgtgactcaa gactcgaggc cgatacgagg ctgtgattct           3450
gcctttggat ggatgttgct gtacacagat gctacagact tgtactaaca           3500
caccgtaatt tggcatttgt ttaacctcat ttataaaagc ttcaaaaaaa           3550
ccca                                                             3554
```

<210> SEQ ID NO 20
<211> LENGTH: 310
<212> TYPE: PRT
<213> ORGANISM: Homo sapiens

<400> SEQUENCE: 20

```
Met Ala Leu Arg Arg Pro Pro Arg Leu Arg Leu Cys Ala Arg Leu
  1               5                  10                  15

Pro Asp Phe Phe Leu Leu Leu Phe Arg Gly Cys Leu Ile Gly
                 20                  25                  30

Ala Val Asn Leu Lys Ser Ser Asn Arg Thr Pro Val Val Gln Glu
                 35                  40                  45

Phe Glu Ser Val Glu Leu Ser Cys Ile Ile Thr Asp Ser Gln Thr
                 50                  55                  60

Ser Asp Pro Arg Ile Glu Trp Lys Lys Ile Gln Asp Glu Gln Thr
                 65                  70                  75

Thr Tyr Val Phe Phe Asp Asn Lys Ile Gln Gly Asp Leu Ala Gly
                 80                  85                  90

Arg Ala Glu Ile Leu Gly Lys Thr Ser Leu Lys Ile Trp Asn Val
                 95                 100                 105

Thr Arg Arg Asp Ser Ala Leu Tyr Arg Cys Glu Val Val Ala Arg
                110                 115                 120

Asn Asp Arg Lys Glu Ile Asp Glu Ile Val Ile Glu Leu Thr Val
                125                 130                 135
```

-continued

```
Gln Val Lys Pro Val Thr Pro Val Cys Arg Val Pro Lys Ala Val
            140                 145                 150
Pro Val Gly Lys Met Ala Thr Leu His Cys Gln Glu Ser Glu Gly
        155                 160                 165
His Pro Arg Pro His Tyr Ser Trp Tyr Arg Asn Asp Val Pro Leu
    170                 175                 180
Pro Thr Asp Ser Arg Ala Asn Pro Arg Phe Arg Asn Ser Ser Phe
185                 190                 195
His Leu Asn Ser Glu Thr Gly Thr Leu Val Phe Thr Ala Val His
            200                 205                 210
Lys Asp Asp Ser Gly Gln Tyr Tyr Cys Ile Ala Ser Asn Asp Ala
        215                 220                 225
Gly Ser Ala Arg Cys Glu Glu Gln Glu Met Glu Val Tyr Asp Leu
    230                 235                 240
Asn Ile Gly Gly Ile Ile Gly Gly Val Leu Val Leu Ala Val
245                 250                 255
Leu Ala Leu Ile Thr Leu Gly Ile Cys Cys Ala Tyr Arg Arg Gly
            260                 265                 270
Tyr Phe Ile Asn Asn Lys Gln Asp Gly Glu Ser Tyr Lys Asn Pro
        275                 280                 285
Gly Lys Pro Asp Gly Val Asn Tyr Ile Arg Thr Asp Glu Glu Gly
    290                 295                 300
Asp Phe Arg His Lys Ser Ser Phe Val Ile
305                 310
```

<210> SEQ ID NO 21
<211> LENGTH: 3437
<212> TYPE: DNA
<213> ORGANISM: Homo sapiens

<400> SEQUENCE: 21

| | |
|---|---|
| caggaccagg tcttcctacg ctggagcagc ggggagacag ccaccatgca | 50 |
| catcctcgtg gtccatgcca tggtgatcct gctgacgctg ggcccgcctc | 100 |
| gagccgacga cagcgagttc caggcgctgc tggacatctg gtttccggag | 150 |
| gagaagccac tgcccaccgc cttcctggtg gacacatcgg aggaggcgct | 200 |
| gctgcttcct gactggctga agctgcgcat gatccgttct gaggtgctcc | 250 |
| gcctggtgga cgccgccctg caggacctgg agccgcagca gctgctgctg | 300 |
| ttcgtgcagt cgtttggcat ccccgtgtcc agcatgagca aactcctcca | 350 |
| gttcctggac caggcagtgg cccacgaccc ccagactctg gagcagaaca | 400 |
| tcatggacaa gaattacatg gcccacctgg tggaggtcca gcatgagcgc | 450 |
| ggcgcctccg gaggccagac tttccactcc ttgctcacag cctccctgcc | 500 |
| gccccgccga gacagcacag aggcacccaa accaaagagc agcccagagc | 550 |
| agcccatagg ccagggccgg attcgggtgg gacccagct ccgggtgctg | 600 |
| ggccctgagg acgacctggc tggcatgttc ctccagattt tcccgctcag | 650 |
| cccggaccct cggtggcaga gctccagtcc cgccccgtg ccctcgccc | 700 |
| tgcagcaggc cctgggccag gagctggccc gcgtcgtcca gggcagcccc | 750 |
| gaggtgccgg gcatcacggt gcgtgtcctg caggccctcg ccaccctgct | 800 |
| cagctcccca cacggcggtg ccctggtgat gtccatgcac cgtagccact | 850 |
| tcctggcctg cccgctgctg cgccagctct gccagtacca gcgctgtgtg | 900 |

-continued

| | |
|---|---|
| ccacaggaca ccggcttctc ctcgctcttc ctgaaggtgc tcctgcagat | 950 |
| gctgcagtgg ctggacagcc tggcgtgga gggcgggccc ctgcgggcac | 1000 |
| agctcaggat gcttgccagc caggcctcag ccgggcgcag gctcagtgat | 1050 |
| gtgcgagggg ggctcctgcg cctggccgag gccctggcct tccgtcagga | 1100 |
| cctggaggtg tcagctcca ccgtccgtgc cgtcatcgcc accctgaggt | 1150 |
| ctggggagca gtgcagcgtg gagccggacc tgatcagcaa agtcctccag | 1200 |
| gggctgatcg aggtgaggtc cccccacctg gaggagctgc tgactgcatt | 1250 |
| cttctctgcc actgcggatg ctgcctcccc gtttccagcc tgtaagcccg | 1300 |
| ttgtggtggt gagctccctg ctgctgcagg aggaggagcc cctggctggg | 1350 |
| gggaagccgg gtgcggacgg tggcagcctg gaggccgtgc ggctggggcc | 1400 |
| ctcgtcaggc ctcctagtgg actggctgga aatgctggac ccgaggtgg | 1450 |
| tcagcagctg ccccgacctg cagctcaggc tgctcttctc ccggaggaag | 1500 |
| ggcaaaggtc aggcccaggt gccctcgttc cgtccctacc tcctgacccct | 1550 |
| cttcacgcat cagtccagct ggcccacact gcaccagtgc atccgagtcc | 1600 |
| tgctgggcaa gagccgggaa cagaggttcg acccctctgc ctctctggac | 1650 |
| ttcctctggg cctgcatcca tgttcctcgc atctggcagg ggcgggacca | 1700 |
| gcgcaccccg cagaagcggc gggaggagct ggtgctgcgg gtccagggcc | 1750 |
| cggagctcat cagcctggtg gagctgatcc tggccgaggc ggagacgcgg | 1800 |
| agccaggacg gggacacagc cgcctgcagc ctcatccagg cccggctgcc | 1850 |
| cctgctgctc agctgctgct gtggggacga tgagagtgtc aggaaggtga | 1900 |
| cggagcacct gtcaggctgc atccagcagt ggggagacag cgtgctggga | 1950 |
| aggcgctgcc gagaccttct cctgcagctc tacctacagc ggccggagct | 2000 |
| gcgggtgccc gtgcctgagg tcctactgca cagcgaaggg gctgccagca | 2050 |
| gcagcgtctg caagctggac ggactcatcc accgcttcat cacgctcctt | 2100 |
| gcggacacca gcgactcccg ggcgttggag aaccgagggg cggatgccag | 2150 |
| catggcctgc cggaagctgg cggtggcgca cccgctgctg ctgctcaggc | 2200 |
| acctgcccat gatcgcggcg ctcctgcacg gccgcaccca cctcaacttc | 2250 |
| caggagttcc ggcagcagaa ccacctgagc tgcttcctgc acgtgctggg | 2300 |
| cctgctggag ctgctgcagc cgcacgtgtt ccgcagcgag caccaggggg | 2350 |
| cgctgtggga ctgccttctg tccttcatcc gcctgctgct gaattacagg | 2400 |
| aagtcctccc gccatctggc tgccttcatc aacaagtttg tgcagttcat | 2450 |
| ccataagtac attacctaca atgcccccagc agccatctcc ttcctgcaga | 2500 |
| agcacgccga cccgctccac gacctgtcct tcgacaacag tgacctggtg | 2550 |
| atgctgaaat ccctccttgc agggctcagc ctgcccagca gggacgacag | 2600 |
| gaccgaccga ggcctggacg aagagggcga ggaggagagc tcagccggct | 2650 |
| ccttgcccct ggtcagcgtc tccctgttca ccctctgac cgcggccgag | 2700 |
| atggcccct acatgaaacg cttttcccgg ggccaaacgg tggaggatct | 2750 |
| gctggaggtt ctgagtgaca tagacgagat gtccggcgg agacccgaga | 2800 |
| tcctgagctt cttctcgacc aacctgcagc ggctgatgag ctcggccgag | 2850 |

| | |
|---|---|
| gagtgttgcc gcaacctcgc cttcagcctg gccctgcgct ccatgcagaa | 2900 |
| cagccccagc attgcagccg ctttcctgcc cacgttcatg tactgcctgg | 2950 |
| gcagccagga cttttgaggtg gtgcagacgg ccctccggaa cctgcctgag | 3000 |
| tacgctctcc tgtgccaaga gcacgcggct gtgctgctcc accgggcctt | 3050 |
| cctggtgggc atgtacggcc agatggaccc cagcgcgcag atctccgagg | 3100 |
| ccctgaggat cctgcatatg gaggccgtga tgtgagcctg tggcagccga | 3150 |
| ccccccctcca gccccggcc cgtcccgtcc ccggggatcc tcgaggcaaa | 3200 |
| gcccaggaag cgtgggcgtt gctggtctgt ccgaggaggt gagggcgccg | 3250 |
| agccctgagg ccaggcaggc ccaggagcaa tactccgagc cctggggtgg | 3300 |
| ctccggggccg gccgctggca tcaggggccg tccagcaagc cctcattcac | 3350 |
| cttctgggcc acagccctgc cgcggagcgg cggatccccc cgggcatggc | 3400 |
| ctgggctggt tttgaatgaa acgacctgaa ctgtcaa | 3437 |

<210> SEQ ID NO 22
<211> LENGTH: 1029
<212> TYPE: PRT
<213> ORGANISM: Homo sapiens

<400> SEQUENCE: 22

```
Met His Ile Leu Val Val His Ala Met Val Ile Leu Leu Thr Leu
  1               5                  10                  15

Gly Pro Pro Arg Ala Asp Asp Ser Glu Phe Gln Ala Leu Leu Asp
                 20                  25                  30

Ile Trp Phe Pro Glu Glu Lys Pro Leu Pro Thr Ala Phe Leu Val
                 35                  40                  45

Asp Thr Ser Glu Glu Ala Leu Leu Leu Pro Asp Trp Leu Lys Leu
                 50                  55                  60

Arg Met Ile Arg Ser Glu Val Leu Arg Leu Val Asp Ala Ala Leu
                 65                  70                  75

Gln Asp Leu Glu Pro Gln Gln Leu Leu Leu Phe Val Gln Ser Phe
                 80                  85                  90

Gly Ile Pro Val Ser Ser Met Ser Lys Leu Leu Gln Phe Leu Asp
                 95                 100                 105

Gln Ala Val Ala His Asp Pro Gln Thr Leu Glu Gln Asn Ile Met
                110                 115                 120

Asp Lys Asn Tyr Met Ala His Leu Val Glu Val Gln His Glu Arg
                125                 130                 135

Gly Ala Ser Gly Gly Gln Thr Phe His Ser Leu Leu Thr Ala Ser
                140                 145                 150

Leu Pro Pro Arg Arg Asp Ser Thr Glu Ala Pro Lys Pro Lys Ser
                155                 160                 165

Ser Pro Glu Gln Pro Ile Gly Gln Gly Arg Ile Arg Val Gly Thr
                170                 175                 180

Gln Leu Arg Val Leu Gly Pro Glu Asp Leu Ala Gly Met Phe
                185                 190                 195

Leu Gln Ile Phe Pro Leu Ser Pro Asp Pro Arg Trp Gln Ser Ser
                200                 205                 210

Ser Pro Arg Pro Val Ala Leu Ala Leu Gln Gln Ala Leu Gly Gln
                215                 220                 225

Glu Leu Ala Arg Val Val Gln Gly Ser Pro Glu Val Pro Gly Ile
                230                 235                 240
```

-continued

```
Thr Val Arg Val Leu Gln Ala Leu Ala Thr Leu Leu Ser Ser Pro
            245                 250                 255

His Gly Gly Ala Leu Val Met Ser Met His Arg Ser His Phe Leu
            260                 265                 270

Ala Cys Pro Leu Leu Arg Gln Leu Cys Gln Tyr Gln Arg Cys Val
            275                 280                 285

Pro Gln Asp Thr Gly Phe Ser Ser Leu Phe Leu Lys Val Leu Leu
            290                 295                 300

Gln Met Leu Gln Trp Leu Asp Ser Pro Gly Val Glu Gly Gly Pro
            305                 310                 315

Leu Arg Ala Gln Leu Arg Met Leu Ala Ser Gln Ala Ser Ala Gly
            320                 325                 330

Arg Arg Leu Ser Asp Val Arg Gly Gly Leu Leu Arg Leu Ala Glu
            335                 340                 345

Ala Leu Ala Phe Arg Gln Asp Leu Glu Val Val Ser Ser Thr Val
            350                 355                 360

Arg Ala Val Ile Ala Thr Leu Arg Ser Gly Glu Gln Cys Ser Val
            365                 370                 375

Glu Pro Asp Leu Ile Ser Lys Val Leu Gln Gly Leu Ile Glu Val
            380                 385                 390

Arg Ser Pro His Leu Glu Glu Leu Leu Thr Ala Phe Phe Ser Ala
            395                 400                 405

Thr Ala Asp Ala Ala Ser Pro Phe Pro Ala Cys Lys Pro Val Val
            410                 415                 420

Val Val Ser Ser Leu Leu Leu Gln Glu Glu Pro Leu Ala Gly
            425                 430                 435

Gly Lys Pro Gly Ala Asp Gly Gly Ser Leu Glu Ala Val Arg Leu
            440                 445                 450

Gly Pro Ser Ser Gly Leu Leu Val Asp Trp Leu Glu Met Leu Asp
            455                 460                 465

Pro Glu Val Val Ser Ser Cys Pro Asp Leu Gln Leu Arg Leu Leu
            470                 475                 480

Phe Ser Arg Arg Lys Gly Lys Gly Gln Ala Gln Val Pro Ser Phe
            485                 490                 495

Arg Pro Tyr Leu Leu Thr Leu Phe Thr His Gln Ser Ser Trp Pro
            500                 505                 510

Thr Leu His Gln Cys Ile Arg Val Leu Leu Gly Lys Ser Arg Glu
            515                 520                 525

Gln Arg Phe Asp Pro Ser Ala Ser Leu Asp Phe Leu Trp Ala Cys
            530                 535                 540

Ile His Val Pro Arg Ile Trp Gln Gly Arg Asp Gln Arg Thr Pro
            545                 550                 555

Gln Lys Arg Arg Glu Glu Leu Val Leu Arg Val Gln Gly Pro Glu
            560                 565                 570

Leu Ile Ser Leu Val Glu Leu Ile Leu Ala Glu Ala Glu Thr Arg
            575                 580                 585

Ser Gln Asp Gly Asp Thr Ala Ala Cys Ser Leu Ile Gln Ala Arg
            590                 595                 600

Leu Pro Leu Leu Leu Ser Cys Cys Cys Gly Asp Asp Glu Ser Val
            605                 610                 615

Arg Lys Val Thr Glu His Leu Ser Gly Cys Ile Gln Gln Trp Gly
            620                 625                 630
```

-continued

```
Asp Ser Val Leu Gly Arg Arg Cys Arg Asp Leu Leu Leu Gln Leu
                635                 640                 645

Tyr Leu Gln Arg Pro Glu Leu Arg Val Pro Val Pro Glu Val Leu
                650                 655                 660

Leu His Ser Glu Gly Ala Ala Ser Ser Val Cys Lys Leu Asp
                665                 670                 675

Gly Leu Ile His Arg Phe Ile Thr Leu Leu Ala Asp Thr Ser Asp
                680                 685                 690

Ser Arg Ala Leu Glu Asn Arg Gly Ala Asp Ala Ser Met Ala Cys
                695                 700                 705

Arg Lys Leu Ala Val Ala His Pro Leu Leu Leu Arg His Leu
                710                 715                 720

Pro Met Ile Ala Ala Leu Leu His Gly Arg Thr His Leu Asn Phe
                725                 730                 735

Gln Glu Phe Arg Gln Gln Asn His Leu Ser Cys Phe Leu His Val
                740                 745                 750

Leu Gly Leu Leu Glu Leu Leu Gln Pro His Val Phe Arg Ser Glu
                755                 760                 765

His Gln Gly Ala Leu Trp Asp Cys Leu Leu Ser Phe Ile Arg Leu
                770                 775                 780

Leu Leu Asn Tyr Arg Lys Ser Ser Arg His Leu Ala Ala Phe Ile
                785                 790                 795

Asn Lys Phe Val Gln Phe Ile His Lys Tyr Ile Thr Tyr Asn Ala
                800                 805                 810

Pro Ala Ala Ile Ser Phe Leu Gln Lys His Ala Asp Pro Leu His
                815                 820                 825

Asp Leu Ser Phe Asp Asn Ser Asp Leu Val Met Leu Lys Ser Leu
                830                 835                 840

Leu Ala Gly Leu Ser Leu Pro Ser Arg Asp Arg Thr Asp Arg
                845                 850                 855

Gly Leu Asp Glu Glu Gly Glu Glu Glu Ser Ser Ala Gly Ser Leu
                860                 865                 870

Pro Leu Val Ser Val Ser Leu Phe Thr Pro Leu Thr Ala Ala Glu
                875                 880                 885

Met Ala Pro Tyr Met Lys Arg Leu Ser Arg Gly Gln Thr Val Glu
                890                 895                 900

Asp Leu Leu Glu Val Leu Ser Asp Ile Asp Glu Met Ser Arg Arg
                905                 910                 915

Arg Pro Glu Ile Leu Ser Phe Phe Ser Thr Asn Leu Gln Arg Leu
                920                 925                 930

Met Ser Ser Ala Glu Glu Cys Cys Arg Asn Leu Ala Phe Ser Leu
                935                 940                 945

Ala Leu Arg Ser Met Gln Asn Ser Pro Ser Ile Ala Ala Ala Phe
                950                 955                 960

Leu Pro Thr Phe Met Tyr Cys Leu Gly Ser Gln Asp Phe Glu Val
                965                 970                 975

Val Gln Thr Ala Leu Arg Asn Leu Pro Glu Tyr Ala Leu Leu Cys
                980                 985                 990

Gln Glu His Ala Ala Val Leu Leu His Arg Ala Phe Leu Val Gly
                995                 1000                1005

Met Tyr Gly Gln Met Asp Pro Ser Ala Gln Ile Ser Glu Ala Leu
                1010                1015                1020

Arg Ile Leu His Met Glu Ala Val Met
```

-continued

1025

<210> SEQ ID NO 23
<211> LENGTH: 2186
<212> TYPE: DNA
<213> ORGANISM: Homo sapiens

<400> SEQUENCE: 23

| | | | | |
|---|---|---|---|---|
| ccgggccatg | cagcctcggc | cccgcgggcg | cccgccgcgc | acccgaggag | 50 |
| atgaggctcc | gcaatggcac | cttcctgacg | ctgctgctct | tctgcctgtg | 100 |
| cgccttcctc | tcgctgtcct | ggtacgcgg | actcagcggc | cagaaaggcg | 150 |
| acgttgtgga | cgtttaccag | cgggagttcc | tggcgctgcg | cgatcggttg | 200 |
| cacgcagctg | agcaggagag | cctcaagcgc | tccaaggagc | tcaacctggt | 250 |
| gctggacgag | atcaagaggg | ccgtgtcaga | aaggcaggcg | ctgcgagacg | 300 |
| gagacggcaa | tcgcacctgg | ggccgcctaa | cagaggaccc | ccgattgaag | 350 |
| ccgtggaacg | gctcacaccg | gcacgtgctg | cacctgccca | ccgtcttcca | 400 |
| tcacctgcca | cacctgctgg | ccaaggagag | cagtctgcag | cccgcggtgc | 450 |
| gcgtgggcca | gggccgcacc | ggagtgtcgg | tggtgatggg | catcccgagc | 500 |
| gtgcggcgcg | aggtgcactc | gtacctgact | gacactctgc | actcgctcat | 550 |
| ctccgagctg | agcccgcagg | agaaggagga | ctcggtcatc | gtggtgctga | 600 |
| tcgccgagac | tgactcacag | tacacttcgg | cagtgacaga | gaacatcaag | 650 |
| gccttgttcc | ccacggagat | ccattctggg | ctcctggagg | tcatctcacc | 700 |
| ctcccccac | ttctaccctg | acttctcccg | cctccgagag | tcctttgggg | 750 |
| accccaagga | gagagtcagg | tggaggacca | aacagaacct | cgattactgc | 800 |
| ttcctcatga | tgtacgcgca | gtccaaaggc | atctactacg | tgcagctgga | 850 |
| ggatgacatc | gtggccaagc | ccaactacct | gagcaccatg | aagaactttg | 900 |
| cactgcagca | gccttcagag | gactggatga | tcctggagtt | ctcccagctg | 950 |
| ggcttcattg | gtaagatgtt | caagtcgctg | gacctgagcc | tgattgtaga | 1000 |
| gttcattctc | atgttctacc | gggacaagcc | catcgactgg | ctcctggacc | 1050 |
| atattctgtg | ggtgaaagtc | tgcaaccccg | agaaggatgc | gaagcactgt | 1100 |
| gaccggcaga | agccaaccct | gcggatccgc | ttcaaaccgt | ccctcttcca | 1150 |
| gcacgtgggc | actcactcct | cgctggctgg | caagatccag | aaactgaagg | 1200 |
| acaaagactt | tggaaagcag | gcgctgcgga | aggagcatgt | gaacccgcca | 1250 |
| gcagaggtga | gcacgagcct | gaagacatac | cagcacttca | ccctggagaa | 1300 |
| agcctacctg | cgcgaggact | tcttctgggc | cttcaccct | gccgcggggg | 1350 |
| acttcatccg | cttccgcttc | ttccaacctc | taagactgga | gcggttcttc | 1400 |
| ttccgcagtg | ggaacatcga | gcacccggag | gacaagctct | tcaacacgtc | 1450 |
| tgtggaggtg | ctgcccttcg | acaaccctca | gtcagacaag | gaggccctgc | 1500 |
| aggagggccg | caccgccacc | ctccggtacc | ctcggagccc | cgacggctac | 1550 |
| ctccagatcg | gctccttcta | caagggagtg | cagagggag | aggtggaccc | 1600 |
| agccttcggc | cctctggaag | cactgcgcct | ctcgatccag | acggactccc | 1650 |
| ctgtgtgggt | gattctgagc | gagatcttcc | tgaaaaaggc | cgactaagct | 1700 |
| gcgggcttct | gagggtaccc | tgtggccagc | cctgaagccc | acatttctgg | 1750 |

```
gggtgtcgtc actgccgtcc ccggagggcc agatacggcc ccgcccaaag        1800
ggttctgcct ggcgtcgggc ttgggccggc ctggggtccg ccgctggccc        1850
ggaggcccta ggagctggtg ctgccccgc  ccgccgggcc gcggaggagg        1900
caggcggccc ccacactgtg cctgaggccc ggaaccgttc gcacccggcc        1950
tgccccagtc aggccgtttt agaagagctt ttacttgggc gcccgccgtc        2000
tctggcgcga acactggaat gcatatacta ctttatgtgc tgtgtttttt        2050
attcttggat acatttgatt ttttcacgta agtccacata tacttctata        2100
agagcgtgac ttgtaataaa gggttaatga agaaaaaaaa aaaaaaaaa         2150 aaaaaaaaaa aaaaaaaaaa aaaaaaaaaa aaaaaa                       2186
```

<210> SEQ ID NO 24
<211> LENGTH: 548
<212> TYPE: PRT
<213> ORGANISM: Homo sapiens

<400> SEQUENCE: 24

```
Met Arg Leu Arg Asn Gly Thr Phe Leu Thr Leu Leu Leu Phe Cys
  1               5                  10                  15

Leu Cys Ala Phe Leu Ser Leu Ser Trp Tyr Ala Ala Leu Ser Gly
             20                  25                  30

Gln Lys Gly Asp Val Asp Val Tyr Gln Arg Glu Phe Leu Ala
         35                  40                  45

Leu Arg Asp Arg Leu His Ala Ala Glu Gln Glu Ser Leu Lys Arg
     50                  55                  60

Ser Lys Glu Leu Asn Leu Val Leu Asp Glu Ile Lys Arg Ala Val
 65                  70                  75

Ser Glu Arg Gln Ala Leu Arg Asp Gly Asp Gly Asn Arg Thr Trp
             80                  85                  90

Gly Arg Leu Thr Glu Asp Pro Arg Leu Lys Pro Trp Asn Gly Ser
             95                 100                 105

His Arg His Val Leu His Leu Pro Thr Val Phe His His Leu Pro
            110                 115                 120

His Leu Leu Ala Lys Glu Ser Ser Leu Gln Pro Ala Val Arg Val
            125                 130                 135

Gly Gln Gly Arg Thr Gly Val Ser Val Val Met Gly Ile Pro Ser
            140                 145                 150

Val Arg Arg Glu Val His Ser Tyr Leu Thr Asp Thr Leu His Ser
            155                 160                 165

Leu Ile Ser Glu Leu Ser Pro Gln Glu Lys Glu Asp Ser Val Ile
            170                 175                 180

Val Val Leu Ile Ala Glu Thr Asp Ser Gln Tyr Thr Ser Ala Val
            185                 190                 195

Thr Glu Asn Ile Lys Ala Leu Phe Pro Thr Glu Ile His Ser Gly
            200                 205                 210

Leu Leu Glu Val Ile Ser Pro Ser Pro His Phe Tyr Pro Asp Phe
            215                 220                 225

Ser Arg Leu Arg Glu Ser Phe Gly Asp Pro Lys Glu Arg Val Arg
            230                 235                 240

Trp Arg Thr Lys Gln Asn Leu Asp Tyr Cys Phe Leu Met Met Tyr
            245                 250                 255

Ala Gln Ser Lys Gly Ile Tyr Tyr Val Gln Leu Glu Asp Asp Ile
```

```
                          260                 265                 270
Val Ala Lys Pro Asn Tyr Leu Ser Thr Met Lys Asn Phe Ala Leu
                275                 280                 285
Gln Gln Pro Ser Glu Asp Trp Met Ile Leu Glu Phe Ser Gln Leu
            290                 295                 300
Gly Phe Ile Gly Lys Met Phe Lys Ser Leu Asp Leu Ser Leu Ile
        305                 310                 315
Val Glu Phe Ile Leu Met Phe Tyr Arg Asp Lys Pro Ile Asp Trp
    320                 325                 330
Leu Leu Asp His Ile Leu Trp Val Lys Val Cys Asn Pro Glu Lys
        335                 340                 345
Asp Ala Lys His Cys Asp Arg Gln Lys Ala Asn Leu Arg Ile Arg
        350                 355                 360
Phe Lys Pro Ser Leu Phe Gln His Val Gly Thr His Ser Ser Leu
        365                 370                 375
Ala Gly Lys Ile Gln Lys Leu Lys Asp Lys Asp Phe Gly Lys Gln
        380                 385                 390
Ala Leu Arg Lys Glu His Val Asn Pro Ala Glu Val Ser Thr
        395                 400                 405
Ser Leu Lys Thr Tyr Gln His Phe Thr Leu Glu Lys Ala Tyr Leu
        410                 415                 420
Arg Glu Asp Phe Phe Trp Ala Phe Thr Pro Ala Ala Gly Asp Phe
        425                 430                 435
Ile Arg Phe Arg Phe Gln Pro Leu Arg Leu Glu Arg Phe Phe
        440                 445                 450
Phe Arg Ser Gly Asn Ile Glu His Pro Glu Asp Lys Leu Phe Asn
        455                 460                 465
Thr Ser Val Glu Val Leu Pro Phe Asp Asn Pro Gln Ser Asp Lys
        470                 475                 480
Glu Ala Leu Gln Glu Gly Arg Thr Ala Thr Leu Arg Tyr Pro Arg
        485                 490                 495
Ser Pro Asp Gly Tyr Leu Gln Ile Gly Ser Phe Tyr Lys Gly Val
        500                 505                 510
Ala Glu Gly Glu Val Asp Pro Ala Phe Gly Pro Leu Glu Ala Leu
        515                 520                 525
Arg Leu Ser Ile Gln Thr Asp Ser Pro Val Trp Val Ile Leu Ser
        530                 535                 540
Glu Ile Phe Leu Lys Lys Ala Asp
        545
```

<210> SEQ ID NO 25
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 25
tgtaaaacga cggccagtta aatagacctg caattattaa tct         43

<210> SEQ ID NO 26
<211> LENGTH: 41
<212> TYPE: DNA
<213> ORGANISM: Artificial Sequence
<220> FEATURE:
<223> OTHER INFORMATION: Synthetic Oligonucleotide Probe -continued

```
<400> SEQUENCE: 26
caggaaacag ctatgaccac ctgcacacct gcaaatccat t                    41

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 27
actcgggatt cctgctgtt                                             19

<210> SEQ ID NO 28
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 28
aggcctttac ccaaggccac aac                                        23

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 29
ggcctgtcct gtgttctca                                             19

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 30
tcccaccact tacttccatg aa                                         22

<210> SEQ ID NO 31
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 31
ctgtggtacc caattgccgc cttgt                                      25

<210> SEQ ID NO 32
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 32
attgtcctga gattcgagca aga                                        23

<210> SEQ ID NO 33
<211> LENGTH: 18
```

```
<212> TYPE: DNA
<213> ORGANISM: Artificial Sequence
<220> FEATURE:
<223> OTHER INFORMATION: Synthetic Oligonucleotide Probe

<400> SEQUENCE: 33
gtccagcaag ccctcatt                                                    18

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 34
cttctgggcc acagccctgc                                                  20

<210> SEQ ID NO 35
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 35
cagttcaggt cgtttcattc a                                                21

<210> SEQ ID NO 36
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 36
ccagtcaggc cgttttaga                                                   19

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 37
cgggcgccca agtaaaagct c                                                21

<210> SEQ ID NO 38
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 38
cataaagtag tatatgcatt ccagtgtt                                         28
```